US008404681B2

(12) United States Patent
Halbrook et al.

(10) Patent No.: US 8,404,681 B2
(45) Date of Patent: Mar. 26, 2013

(54) XANTHONES, THIOXANTHONES AND ACRIDINONES AS DNA-PK INHIBITORS

(75) Inventors: James W. Halbrook, Mercer Island, WA (US); Edward A. Kesicki, Bothell, WA (US); Laurence E. Burgess, Boulder, CO (US); Stephen T. Schlachter, Boulder, CO (US); Charles T. Eary, Longmont, CO (US); Justin G. Schiro, Baudette, MN (US)

(73) Assignee: Luitpold Pharmaceuticals, Inc., Shirley, NY (US)

( * ) Notice: Subject to any disclaimer, the term of this patent is extended or adjusted under 35 U.S.C. 154(b) by 1412 days.

(21) Appl. No.: 10/550,978

(22) PCT Filed: Mar. 19, 2004

(86) PCT No.: PCT/US2004/008459
§ 371 (c)(1),
(2), (4) Date: Dec. 11, 2006

(87) PCT Pub. No.: WO2004/085418
PCT Pub. Date: Oct. 7, 2004

(65) Prior Publication Data
US 2007/0167441 A1 Jul. 19, 2007

Related U.S. Application Data

(60) Provisional application No. 60/456,999, filed on Mar. 24, 2003.

(51) Int. Cl.
*A61K 31/535* (2006.01)
*C07D 413/04* (2006.01)
(52) U.S. Cl. ..................... 514/232.8; 544/126
(58) Field of Classification Search ............... 514/232.8; 544/126
See application file for complete search history.

(56) References Cited

U.S. PATENT DOCUMENTS

| | | | | |
|---|---|---|---|---|
| 3,835,158 A * | 9/1974 | Pfister et al. ................. | 549/60 |
| 3,904,631 A | 9/1975 | Elslager et al. | |
| 4,003,699 A | 1/1977 | Rose et al. | |
| 4,404,389 A | 9/1983 | Vamvakaris et al. | |
| 4,410,708 A | 10/1983 | Yahagi et al. | |
| 4,451,462 A | 5/1984 | Wenk et al. | |
| 4,539,412 A | 9/1985 | Archer | |
| 4,558,043 A | 12/1985 | Wenk et al. | |
| 4,904,798 A | 2/1990 | Kranz et al. | |
| 5,262,549 A | 11/1993 | Telfer et al. | |
| 5,401,739 A | 3/1995 | Ohno et al. | |
| 6,174,887 B1 | 1/2001 | Haruta et al. | |
| 6,535,593 B1 | 3/2003 | Cashiola | |
| 6,747,057 B2 | 6/2004 | Ruzafa et al. | |
| 7,179,912 B2 | 2/2007 | Halbrook et al. | |
| 2001/0027210 A1 | 10/2001 | Wilson | |
| 2008/0090782 A1 | 4/2008 | Halbrook et al. | |

FOREIGN PATENT DOCUMENTS

| | | |
|---|---|---|
| DE | 29 22 488 A1 | 12/1980 |
| DE | 31 41 970 A1 | 5/1983 |
| DE | 44 24 712 A1 | 1/1996 |
| EP | 0 078 241 A2 | 5/1983 |
| EP | 0 106 800 A1 | 4/1984 |
| EP | 0 107 620 A1 | 5/1984 |
| EP | 0 342 665 A2 | 11/1989 |
| EP | 0 471 516 A1 | 2/1992 |
| FR | 8 298 M | 11/1970 |
| FR | 1 355 173 A1 | 2/2004 |
| GB | 2109373 A | 6/1983 |
| GB | 2326410 A1 | 12/1998 |
| JP | 5708845 | 6/1982 |
| JP | 04-257563 | 9/1992 |
| JP | 04-368379 | 12/1992 |
| JP | 09-316440 | 12/1997 |
| JP | 11 106371 A1 | 4/1999 |
| JP | 11-199565 | 7/1999 |
| JP | 06-506202 | 2/2006 |
| WO | WO 90/14008 A1 | 11/1990 |
| WO | WO 92/16517 A1 | 10/1992 |
| WO | WO 92/20666 A1 | 11/1992 |
| WO | WO 95/20652 A1 | 8/1995 |
| WO | WO 96/16632 A1 | 6/1996 |
| WO | WO 96/22077 A1 | 7/1996 |
| WO | WO 97/08133 A1 | 3/1997 |
| WO | WO 97/31891 A1 | 9/1997 |
| WO | WO 98/13502 A2 | 4/1998 |
| WO | WO 99/14212 A1 | 3/1999 |
| WO | WO 99/29705 A2 | 6/1999 |
| WO | WO 99/39247 A1 | 8/1999 |
| WO | WO 00/00644 A1 | 1/2000 |
| WO | WO 00/17386 A1 | 3/2000 |
| WO | WO 00/18750 A2 | 4/2000 |
| WO | WO 01/17985 A1 | 3/2001 |
| WO | WO 02/20500 A2 | 3/2002 |
| WO | WO 03/055479 A1 | 7/2003 |

OTHER PUBLICATIONS

Abadi, A.H., et al., "Synthesis, Antitumor and Antitubercular Evaluation of Certain New Xanthenone and Acridinone Analogs," *Arzneim.-Forsch./Drug Res.* 49 (I), Nr. 3, pp. 259-266 (1999).
Agasimundin, Y.S., et al., (Abstract) "Furano compounds. XX. Synthesis of angular and linear furoxanthones," *Journal fuer Praktische Chemie* (Leipzig) (1972), 314(3-4), pp. 507-514.
Araki et al., "Nonsense mutation at TYR-4046 in the DNA-dependent protein kinase catalytic subunit of severe combined immune deficiency mice", *Proc. Natl. Acad. Sci. USA*, vol. 94, pp. 2438-2443 (1997).
Biedermann et al., "*scid* mutation in mice confers hypersensitivity to ionizing radiation and a deficiency in DNA double-strand break repair", *Proc. Natl. Acad. Sci. USA*, vol. 88, pp. 1394-1397 (1991).
Blunt et al., "Defective DNA-Dependent Protein Kinase Activity is Linked to V(D)J Recombination and DNA Repair Defects Associated with the Murine *scid* Mutation", *Cell Press*, vol. 80, pp. 813-823 (1995).

(Continued)

*Primary Examiner* — Rebecca Anderson
(74) *Attorney, Agent, or Firm* — Wolf, Greenfield & Sacks, P.C.

(57) ABSTRACT

Compound that inhibit DNA-dependent protein kinase, compositions comprising the compounds, methods of inhibiting the DNA-PK biological activity, methods of sensitizing cells the agents that cause DNA lesions, and methods of potentiating cancer treatment are disclosed.

18 Claims, No Drawings

OTHER PUBLICATIONS

Blunt et al., "Identification of a nonsense mutation in the carboxyl-terminal region of DNA-dependent protein kinase catalytic subunit in the *scid* mouse", *Proc. Natl. Acad. Sci. USA*, vol. 93, pp. 10285-10290 (1996).

Brown et al., "Toxicity of Selected Organic Compounds to Insects", *Can. J. Research*, vol. 26D, pp. 177-187, (1948).

Christodoulopoulos et al., "Potentiation of Chlorambucil Cytotoxicity in B-Cell Chronic Lymphocytic Leukemia by Inhibition of DNA-dependent Protein Kinase Activity Using Wortmannin[b]", *Cancer Research*, vol. 58, pp. 1789-1792 (1998).

Cretcher et al., "Syntheses with β, β'—Dichloro-Diethyl Ether", *Journal of the American Chemical Society*, vol. 47, pp. 163-166 (1925).

Croisy-Delcey, M., et al., "Aza Analogues of Lucanthone: Synthesis and Antitumor and Bactericidal Properties," *J. Med. Chem.* 1983, 26, pp. 1329-1333.

Daniel et al., "A Role for DNA-PK in Retroviral DNA Integration", *Science*, vol. 284, pp. 644-647, (1999).

Effenberger et al. , "Aminobenzenes. VIII. Rearrangement of phenyl carbamates. Syntheses of 2, 4-dioxo-3, 4-dihydro-2H-1,3-benzoxazines and salicylamides", *Chemische Berichte* vol. 105, pp. 1926-1942 (1972).

Eiden et al., "Darstellung und Reaktionen von 2-Acetyl-3-amino-5-hydroxy-2-2cyclohexenonen; Benzol-Derivat aus pyronen", *Archiv der Pharmazie* (Weinheim, Germany), vol. 318(4), pp. 328-340 (1985).

Elslager et al., "Synthetic Schistosomicides. XVI. 5-(Mono- and Dialkylamino)-2-nitrosophenols, 2-Amino-5-(dialkylamino)phenols, and Related Compounds", *Journal of Medicinal Chemistry*, vol. 13(3), pp. 370-376 (1970).

Fonteneau, N., et al., "Synthesis of quinone and xanthone analogs of rhein," *Tetrahedron 57* (2001) pp. 9131-9135.

Fujioka, H., et al., "Activities of New Acridone Alkaloid Derivatives against Plasmodium yoelii in vitro," *Arzneim.-Forsch./Drug Res*. 40 (II), Nr. 9 (1990), pp. 1026-1029.

Fulop G.M. and Phillips, R.A., "The *scid* mutation in mice causes a general defect in DNA repair", *Nature*, vol. 347, pp. 479-482 (1990).

Ghosh, C.K., et al., "Benzopyrans. Part 30. Synthesis of Substituted Xanthones from 3-Acyl-2-methyl-1-benzopyran-4-ones", *Tetrahedron* vol. 49, No. 19, pp. 4127-4134, 1993.

Gilman et al., "Rearrangements in Amination by Alkali Amides in Liquid Ammonia and by Lithium Dialkylamides in Ether", *Journal of the American Chemical Society*, vol. 74, pp. 3027-3029, (1952).

Goud, A.N., et al., "Furan compounds. XVI," *Monatsh. Chem*. (1969), 100(1), pp. 38-41.

Harfenist, M., et al., "Selective Inhibitors of Monoamine Oxidase. 3. Structure-Activity Relationship of Tricyclics Bearing Imidazoline, Oxadiazole, or Tetrazole Groups," *J. Med. Chem.* 1996, 39, pp. 1857-1863.

Hendrickson et al., "A link between double-strand break-related repair and V(d)J recombination: The *scid* Mutation", *Proc. Natl. Acad. Sci. USA*, vol. 88. pp. 4061-4065, (1991).

International Search Report of PCT/US2004/008459, mailed Oct. 11, 2004.

Izzard et al., "Competitive and Noncompetitive Inhibition of the DNA-dependent Protein Kinase", *Cancer Research*, vol. 59, pp. 2581-2586 (1999).

Jackson, Stephen P., "DNA-dependent Protein Kinase", *Cell. Biol.*, vol. 29, No. 7, pp. 935-938 (1997).

Klopman, G., et al., "An artificial intelligence approach to the study of the structural moieties relevant to drug-receptor interactions in aldose reductase inhibitors," *Molecular Pharmacology* (1988), 34(6), pp. 852-862.

Langer et al., "Rearrangement of o-benzoquinol acetates with amines", *Monatshefie fuer Chemi*, vol. 90, pp. 623-633 (1959).

Mari, S., et al., "Flavone and xanthone derivatives related to fluoroquinolones," *Il Farmaco* 54 (1999) pp. 411-415.

Peterson et al., "Loss of the catalytic subunit of the DNA-dependent protein kinase in DNA double-strand-break-repair mutant mammalian cells", *Proc. Natl. Acad. Sci. USA*, vol. 92, pp. 3171-3174 (1995).

Powell et al., Differential Sensitivity of p53[(-)] and P53[(+)] Cells to Caffeine-induced Audiosensation and Override of $G_2$ Delay[1], *Cancer Research*, vol. 55, pp. 1643-1648 (1995).

Russell et al. "Abrogation of the $G_2$ Checkpoint Results in Differential Radiosensitization of Checkpoint-deficient and $G^1$ Checkpoint-competent Cells[1]", *Cancer Research*, vol. 55, pp. 1639-1642 (1995).

Tabarrini, O., et al., "Design and Synthesis of Modified Quinolones as Antitumoral Acridones," *J. Med. Chem.*, 1999, vol. 42, No. 12, pp. 2136-2144.

Windholz (Ed.) et al., "The Merck Index, ninth edition", p. 84, No. 658; p. 159, No. 1229; p. 187, No. 1458; p. 193, No. 1500; p. 263, No. 2050; p. 474, No. 3550; p. 680, No. 5043, p. 847, No. 6342; p. 871, No. 6521, p. 936, No. 7009; p. 939, No. 7031; p. 1069, No. 8011; p. 1080, No. 8094; p. 1275, No. 9592; (1976), Rahway, N.J.

Xuan, T., et al., "Two new O- and C-glycosylxanthones from the Gentiana tizuensis Franch," *Gaodeng Xuexiao Huaxue Xuebao* (2001), 22(10, Suppl.), pp. 148-150.

International Preliminary Report on Patentability dated Oct. 1, 2005 mailed in connection with PCT/US2004/008459.

Zhao et al., Preclinical evaluation of a potent novel DNA-dependent protein kinase inhibitor NU7441. Cancer Res. May 15, 2006;66(10):5354-62.

* cited by examiner

XANTHONES, THIOXANTHONES AND ACRIDINONES AS DNA-PK INHIBITORS

RELATED APPLICATIONS

This application is a national stage filing under 35 U.S.C. §371 of PCT International application PCT/US2004/008459, filed Mar. 19, 2004, which claims priority under 35 U.S.C. §119(e) from U.S. provisional application Ser. No. 60/456,999, filed Mar. 24, 2003.

FIELD OF THE INVENTION

The present invention relates to inhibitors of DNA-dependent protein kinase (DNA-PK), and to methods of using the inhibitors to potentiate cancer treatment.

BACKGROUND OF THE INVENTION

All cells possess mechanisms to maintain integrity of the cellular genome through detection and repair of, for example, adduct formation, cross-linking, single-strand breaks, and double-strand breaks. The mechanisms of detection and damage repair, collectively, are called DNA repair. DNA repair functions are performed oil lesions that arise from exposure to a variety of environmental chemical and physical agents, as well as from toxic agents generated intracellularly in normal cellular metabolism. Because DNA provides the information required for cell, tissue, and organism function, a large amount of cellular energy is devoted to maintaining intact structure of the genome.

The most genotoxic damages are those which induce DNA chain disruptions, particularly double-strand breaks. DNA double-strand breaks (dsbs) can be induced by chemical or physical agents, including intercalating agents, electrophilic compounds, and ionizing radiation. At least two pathways responsible for the repair of DNA dsbs exist, i.e., homologous recombination (HR) and nonhomologous end joining (NHEJ). The former reaction requires undamaged DNA from the homologous chromosome to be used as a template in the repair of the DNA discontinuity. NHEJ, in contrast, is DNA homology independent and simply requires two free DNA ends to be relegated. The exact molecular mechanisms by which both HR and NHEJ are effected remain to be elucidated.

DNA dsbs also are generated during the course of normal cellular development in some tissues. This observation first was appreciated following the discovery and characterization of the severe combined immunodeficiency (scid) mouse. The scid syndrome is a genetic disorder which manifests as an absence of B- and T-cell immunity (Bosma et al., *Nature,* 301:527-530 (1983), and reviewed in Bosma et al., *Annu. Rev. Immunol.,* 9:323-350 (1991)). The scid mouse is defective in the earliest stages of lymphoid cell development as a result of an inability to correctly rearrange T-cell receptor (TCR) and IgM μ chain DNA (Bosma et al., *Annu. Rev. Immunol.,* 9:323-350 (1991), Dorshkind et al., *J. Immunol.,* 132:1804-1808 (1984), Lauzon et al., *J. Exp. Med.,* 164:1797-1802 (1986), Schuler et al., *Cell,* 46:963-972 (1986), Tutt et al., *J. Immunol.,* 138:2338-2344 (1987), Lieber et al., *Cell,* 55:7-16 (1988)). As a result, T- and B-cells do not progress beyond the $CD25^+$, $CD4^-$, $CD8^-$, and $CD25^-$ pro-B cell stages, respectively. Site-specific V(D)J recombination is initiated in scid mice through the activity of the RAG1 and RAG2 gene products, however, resolution of recombination intermediates is disrupted (Fulop et al., *Nature,* 347:479-482 (1990), Biedermann et al., *Proc. Natl. Acad. Sci. USA,* 88:1394-1397 (1991), Hendrickson et al., *Proc. Natl. Acad. Sci. USA,* 88:4061-4065 (1991), Oettinger et al., *Science,* 248:1517-1522 (1990), Mombaerts et al., *Cell,* 68:869-877 (1992), Shinkai et al., *Cell,* 68:855-867 (1992), van Gent et al., *Cell,* 81:925-934 (1995), and reviewed in Lieber, *FASEB J.,* 5:2934-2944 (1991)). Nonproductive rearrangements in scid cells typically result in large deletions at the TCR and Ig loci, while the processing of recombination signal sequences is not affected in these cells. The scid mutation, therefore, specifically disrupts the formation of recombinant coding junctions (Lieber et al., *Cell,* 55:7-16 (1988), Malynn et al., *Cell,* 54:453-460 (1988)).

The defect in the scid mouse is caused by mutation of the gene encoding the catalytic subunit of the DNA-dependent protein kinase (DNA-PK) (Blunt et al., *Cell,* 80:813-823 (1995), Peterson et al., *Proc. Natl. Acad. Sci. USA,* 92:3171-3174 (1995)). Specifically, a nonsense mutation at tyrosine-4046 results in the deletion of the last 83 amino acid residues (Blunt et al., *Proc. Natl. Acad. Sci. USA,* 93:10285-10290 (1996), Danska et al., *Mol. Cell. Biol.,* 16:5507-5517 (1996), Araki et al., *Proc. Natl. Acad. Sci. USA,* 94:2438-2443 (1997)).

DNA-PK is a trimeric complex composed of a p460 catalytic subunit and Ku80 (86 kDa) and Ku70 regulatory proteins. Ku70 and Ku80 were initially described as human autoantigens and function as co-factors in vitro stimulating protein kinase activity through binding DNA (Mimori, *J. Clin. Invest.,* 68:611-620 (1981), Dvir et al., *Proc. Natl. Acad. Sci. USA,* 89:11920-11924 (1992), Gottlieb and Jackson, *Cell,* 72:131-142 (1993)). Ku70 and Ku80 exhibit highest affinity for DNA duplex termini and gaps (Blier et al., *J. Biol. Chem.,* 268:7594-7601 (1993), Falzon et al., *J. Biol. Chem.,* 268: 10546-10552 (1993)). Although, the precise function of DNA-PK and its natural substrates remain unknown, this enzyme phosphorylates a number of proteins in vitro, including many transcription factors and p53 (Lees-Miller et al., *Mol. Cell. Biol.,* 12:5041-5049 (1992), Anderson and Lees-Miller, *Crit. Rev. Euk. Gene Exp.,* 2:283-314 (1992)).

Cultured scid cells are sensitive to killing by agents that induce DNA double-strand breaks (dsbs), indicating a role for DNA-PK in the repair of these lesions. The scid defect, also sensitizes mice to radiation-induced lymphomagenesis (Lieberman et al., *J. Exp. Med.,* 176:399-405 (1992)). Lymphomas arise in scid mice at frequencies ranging from 50 to 100% at x-ray doses that do not affect wild-type mice. Because unirradiated scid mice are not particularly sensitive to lymphomagenesis, the background level of tumor-inducing dsbs must either be low enough to be effectively repaired or the damaged cells are effectively eliminated.

The therapeutic benefit of radiation and chemotherapy in the treatment of cancer is well documented. These physical and chemical agents act by disrupting DNA metabolism at the level of DNA structure, synthesis, transcription and chromosome transmission. Most of these agents act by inducing DNA-specific lesions. Presumably, if tumor cells are sensitive to therapies that introduce DNA specific lesions, then these therapies will be made more effective by simultaneously disrupting the cellular repair of these damages. Therefore, inhibition of cellular DNA-PK activity following treatment with agents that induces DNA dsbs will potentiate the therapeutic index of these agents.

Thus, there exists a need in the art to identify compounds that can improve the efficiency of radiation and chemotherapy in treatment of cancer. Identification of DNA-PK inhibitors can permit development of treatment regimens that include lower doses of radiation and/or chemotherapy drugs, thereby reducing the unwanted adverse side effects that often accompany the treatments.

SUMMARY OF THE INVENTION

The present invention provides compounds having a DNA-PK inhibiting activity. The present DNA-PK inhibitors can be used in diagnostic and therapeutic methods useful in the field of cancer therapy. More particularly, the DNA-PK inhibitors permit development of compositions and treatment regimens that can be used with doses of radiation and/or chemotherapy drugs lower than a standard prescribed dose. The reduced exposure to radiation and chemotherapy drugs improves a patient's prognosis with regard to unwanted adverse side effects that often accompany cancer treatments.

The DNA-PK inhibitors of the invention have a structural formula (I):

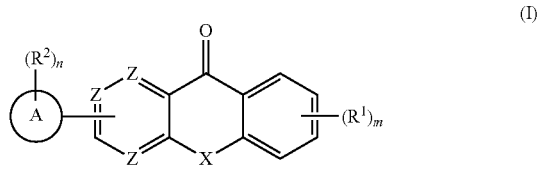

or a pharmaceutically acceptable salt or prodrug thereof,
wherein m is an integer 0 through 3;
n is an integer 0 through 4;
X is O, $S(O)_{0-2}$, or $NR^a$;
Z independently, is $CR^b$ or N;
A is a heteroaryl or four- to seven-membered aliphatic ring containing 0, 1, 2, or 3 heteroatoms independently selected from the group consisting of N, O, and S;
$R^1$, independently, is selected from the group consisting of halo, alkyl, substituted alkyl, cycloalkyl, substituted cycloalkyl, heterocycloalkyl, substituted heterocycloalkyl, $N(R^d)_2$, $OR^d$, carboxyl, carboxy, nitro, $OC_{1-3}$alkylene$N(R^b)_2$, $N(R^d)C_{1-3}$-alkylene$N(R^b)_2$, $OC_{1-3}$alkyleneC(=O)$OR^d$, $OP(=O)(OR^d)_2$, $OP(=O)(ONa)_2$, $O(C_{1-3}$alkylene)OP(=O)(OR$^d$)$_2$, $O(C_{1-3}$alkylene)OP(=O)(ONa)$_2$, cyano, aldehyde, carboxamide, thiocarboxamide, acyl, mercapto, sulfonyl, trifluoromethyl, aryl, substituted aryl, heteroaryl, and substituted heteroaryl; or two $R^1$ groups are taken together with the atoms to which each is attached to form a 5-, 6-, or 7-membered ring, wherein 1 or 2 carbon atoms of $R^1$ optionally is a heteroatom selected from the group consisting of O, N, and S, said ring optionally substituted with one or more =O, =S, =NH, $OR^d$, $N(R^d)_2$, carboxyl, carboxy, alkyl, aryl, substituted aryl, heteroaryl, or substituted heteroaryl, said heteroatom optionally substituted with a group selected from the group consisting of aryl, substituted aryl, alkyl, substituted alkyl, and acyl;

$R^2$, independently, is selected from the group consisting of $OR^d$, halo, $N(R^d)_2$, aldehyde, alkyl, substituted alkyl, acyl, aryl, substituted aryl, heteroaryl, substituted heteroaryl, $C_{1-3}$alkylene$OR^d$, $C(=O)N(R^d)_2$, $N(R^d)_2$, $(C=O)OR^d$, $NO_2$, $NR^dC(=O)R^d$, $NR^d(SO_2)R^d$, $OC_{1-3}$alkylene$OR^d$, $OC_{1-3}$alkyleneOC$_{1-3}$alkyleneR$^d$, $OC(=O)R^d$, $OC_{1-3}$alkyleneC(=O)C$_{1-3}$alkyleneR$^b$, and $O(SO_3)R^d$.

$R^a$ is selected from the group consisting of hydro, $C_{1-4}$alkyl, aryl, heteroaryl, cycloalkyl, heterocycloalkyl, $C_{1-3}$alkylenearyl, $C_{1-3}$alkyleneheteroaryl, $C_{1-3}$alkylenehet-erocycloalkyl, $C_{1-4}$alkyleneN(R$^d$)$_2$, $C_{1-4}$alkyleneOR$^d$, $C_{1-4}$alkyleneC(=O)OR$^d$, C(=O)R$^d$, C(=O)N(R$^d$)$_2$, C(=O)OR$^d$, C(=O)SR$^d$, C(=S)N(R$^d$)$_2$, SO$_2$R$^d$, SO$_2$N(R$^d$)$_2$, C(=O)NR$^d$C$_{1-4}$alkyleneOR$^d$, C(=O)NR$^d$C$_{1-4}$alkyleneheterocycloalkyl, C(=O)C$_{1-4}$alkylenearyl, C(=O)C$_{1-4}$alkyleneheteroaryl, $C_{1-4}$alkyleneC(=O)C$_{1-4}$alkylenearyl, $C_{1-4}$alkyleneC(=O)C$_{1-4}$alkyleneheteroaryl, $C_{1-4}$alkyleneC(=O)heterocycloalkyl, $C_{1-4}$alkyleneNR$^d$C(=O)R$^d$, $C_{1-4}$alkyleneOC$_{1-4}$alkyleneOR$^d$, $C_{1-4}$alkyleneOC$_{1-4}$alkylenreC(=O)OR$^d$, and $C_{1-4}$alkyleneC(=O)N(R$^d$)$_2$;

$R^b$, independently, is selected from the group consisting of hydro, alkyl, halo, aldehyde, $OR^d$, $O(C_{1-3}$alkylene)OP(=O)(OR$^d$)$_2$, $O(C_{1-3}$alkylene)OP(=O)(ONa)$_2$, OP(=O)(OR$^d$)$_2$, OP(=O)(ONa)$_2$, nitro, $N(R^d)_2$, carboxyl, carboxy, sulfonamido, sulfamyl, and sulfo or a halide derivative thereof; and $R^d$, independently, is selected from the group consisting of hydro, alkyl, substituted alkyl, cycloalkyl, substituted cycloalkyl, heterocycloalkyl, substituted heterocycloalkyl, aryl, $C_{1-3}$alkylenearyl, substituted aryl, heteroaryl, and substituted heteroaryl.

Additional compounds useful as DNA-PK inhibitors have a structural formula (II):

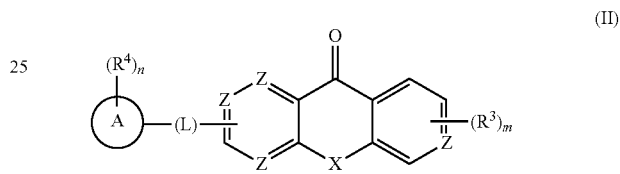

or a pharmaceutically acceptable salt or prodrug thereof,
wherein m, n, X, Z, $R^1$, $R^2$, $R^a$, $R^b$ and $R^d$ are defined above;
L is selected from the group consisting of alkylene, substituted alkylene, carbonyl, carbamoyl, $-NR^d-$, $-N(R^d)_2$, $-O(SO_2)R^d$, oxy, thio, thionyl, and sulfonyl; and
A is absent, or A is heteroaryl or a four- to seven-membered aliphatic ring containing 0, 1, 2, or 3 heteroatoms independently selected from the group consisting of N, O, and S.

The invention further provides a pharmaceutical composition comprising (a) one or more DNA-PK inhibitors of formula (I) or (II) and (b) a pharmaceutically acceptable carrier. The pharmaceutical composition optionally comprises an antineoplastic agent.

The invention also provides pharmaceutical compositions comprising (a) one or more DNA-PK inhibitors of formula (I) or (II) and (b) a radiotherapeutic (or antineoplastic agent). Radiotherapeutic agents include compounds that can be targeted to neoplastic cell types and include one or more attached radioisotopes.

The invention also provides methods of inhibiting DNA-PK activity. The method comprises the step of contacting a DNA-PK with one- or more compounds of formula (I) or (II).

The invention further provides methods of sensitizing a cell to an agent that induces a DNA lesion comprising the step of contacting the cell with one or more DNA-PK inhibitors of formula (I) or (II). In one aspect, the agent that induces a DNA lesion is selected from the group consisting of radiation, exogenous chemicals, metabolite by-products, and combinations thereof.

The invention further provides methods of potentiating a therapeutic regimen for treatment of cancer comprising the step of administering an effective amount of a DNA-PK inhibitor of formula (I) or (II) to an individual in need thereof. In one aspect, methods include those wherein the therapeutic regimen for treatment of cancer is selected from the group consisting of chemotherapy, radiation therapy, and a combination chemotherapy and radiation therapy. In methods wherein the therapeutic regimen includes chemotherapy, the DNA-PK inhibitor is administered before, concurrently with, and/or after administration of the chemotherapeutic agent. The therapeutic regimen also further can include any other conventional or experimental therapy, including, for example, nutritional and/or surgical techniques.

The invention also provides methods of characterizing the potency of a test compound as an inhibitor of a DNA-PK polypeptide, said method comprising the steps of: (a) measuring activity of a DNA-PK polypeptide in the presence of a test compound; (b) comparing the activity of the DNA-PK polypeptide in the presence of the test compound to the activity of the DNA-PK enzyme in the presence of an equivalent amount of a reference compound of formula (I) or (II), wherein a lower activity of the DNA-PK polypeptide in the presence of the test compound than in the presence of the reference compound indicates that the test compound is a more potent inhibitor than the reference compound, and a higher activity of the DNA-PK polypeptide in the presence of the test compound than in the presence of the reference compound indicates that the test compound is a less potent inhibitor than the reference compound.

The invention further provides methods of characterizing the potency of a test compound as an inhibitor of a DNA-PK polypeptide, said method comprising the steps of: (a) determining an amount of a control compound of formula (I) or (II) that inhibits an activity of a DNA-PK polypeptide by a reference percentage of inhibition, thereby defining a reference inhibitory amount for the control compound; (b) determining an amount of a test compound that inhibits an activity of a DNA-PK polypeptide by a reference percentage of inhibition, thereby defining a reference inhibitory amount for the test compound; (c) comparing the reference inhibitory amount for the test compound to the reference inhibitory amount determined according to step (a) for the control compound of formula (I) or (II), wherein a lower reference inhibitory amount for the test compound than for the control compound indicates that the test compound is a more potent inhibitor than the control compound, and a higher reference inhibitory amount for the test compound than for the control compound indicates that the test compound is a less potent inhibitor than the control compound. The method utilizes a reference inhibitory amount, which is the amount of the compound that inhibits the activity of the DNA-PK polypeptide by 50%, by 60%, by 70%, or by 80%. In another aspect, the method employs a reference inhibitory amount that is the amount of the compound that inhibits the activity of the DNA-PK polypeptide by 90%, by 95%, or by 99%. Methods of the invention can comprise determining the reference inhibitory amount of the test compound in an in vitro biochemical assay, determining the reference inhibitory amount of the test compound in an in vitro cell-based assay, or determining the reference inhibitory amount of the test compound in an in vivo assay.

The invention also provides an article of manufacture comprising: (a) a packaged anticancer compound that induces double-strand DNA breakage in cells, and (b) a package insert describing coordinated administration to a patient of said anticancer compound and a DNA-PK inhibitor compound of formula (I) or (II). The article of manufacture comprises an anticancer compound, preferably a chemotherapeutic compound, preferably selected from the group consisting of bleomycin, etoposide, and chlorambucil.

The invention further provides an article of manufacture, comprising: (a) a packaged compound selected from the group consisting of a cytokine, a lymphokine, a growth factor, and a hematopoietic factor, and (b) a package insert describing coordinated administration to a patient of said compound and a DNA-PK inhibitor compound of formula (I) or (II).

The above articles of manufacture optionally can include a packaged DNA-PK inhibitor compound of formula (I) or (II).

DETAILED DESCRIPTION OF THE INVENTION

Definitions

An "$IC_{50}$ value" of a compound is defined as the concentration of the compound required to produce 50% inhibition of DNA-PK biological or enzymatic activity. Inhibitors of DNA-PK activity are defined to have an $IC_{50}$ of less than about 200 µM, preferably less than about 100 µM, less than about 50 µM, and from about 0.005 µM to 40 µM. Most preferably, a present inhibitor has an $IC_{50}$ of less than 1 µM.

The term "pharmaceutically acceptable carrier" as used herein refers to compounds suitable for use in contact with recipient animals, preferably mammals, and more preferably humans, and having a toxicity, irritation, or allergic response commensurate with a reasonable benefit/risk ratio, and effective for their intended use.

The term "prodrug" as used herein refers to compounds that transform rapidly in vivo to a compound of the invention, for example, by hydrolysis. Prodrugs of the invention also can be active in the prodrug form. A thorough discussion is provided in Higuchi et al., *Prodrugs as Novel Delivery Systems*, Vol. 14, of the A.C.S.D. Symposium Series, and in Roche (ed), *Bioreversible Carriers in Drug Design*, American Pharmaceutical Association and Pergamon Press, 1987.

The term "alkyl" and "alkylene" as used herein refer to straight- and branched-chain hydrocarbon groups, preferably containing one to sixteen carbon atoms. Examples of alkyl groups are $C_{1-4}$alkyl groups. As used herein the designation $C_{x-y}$, wherein x and y are integers, denotes a group having from x to y carbons, e.g., a $C_{1-4}$alkyl group is an alkyl group having one to four carbon atoms. Nonlimiting examples of alkyl groups include, but are not limited to, methyl, ethyl, n-propyl, isopropyl, n-butyl, sec-butyl (2-methylpropyl), t-butyl (1,1-dimethylethyl), and the like. Nonlimiting examples of alkylene groups include methylene (—$CH_2$—) and ethylene (—$CH_2CH_2$—).

The term "cycloalkyl" as used herein refers to an aliphatic cyclic hydrocarbon group, preferably containing three to eight carbon atoms. Nonlimiting examples of cycloalkyl groups include cyclopropyl, cyclobutyl, cyclopentyl, cyclohexyl, and the like.

The terms "substituted alkyl," "substituted cycloalkyl," and "substituted alkylene" as used herein refer to an alkyl, cycloalkyl, or alkylene group having one or more substituents. The substituents include, but are not limited to, cycloalkyl, aryl, heteroaryl, heterocycloalkyl, substituted aryl, substituted heteroaryl, substituted heterocycloalkyl, $N(R^d)_2$, $OR^d$, $SR^d$, sulfoxide, sulfonyl, halo, carboxyl, acyl, carboxy, hydrazino, hydrazono, and hydroxyamino. The preferred substituted alkyl groups have one to four carbon atoms, not including carbon atoms of the substituent group. Preferably, a substituted alkyl group is mono- or di-substituted at one, two, or three carbon atoms. The substituents can be bound to the same carbon or different carbon atoms.

The term "alkoxy" as used herein refers to a straight- or branched-chain alkyl, optionally substituted, group attached to the parent molecule through an oxygen atom, typically by a carbon to oxygen bond, i.e., —OR, wherein R is an alkyl group. The hydrocarbon group of the alkoxy group preferably contains one to four carbon atoms. Typical alkoxy groups include, but are not limited to, methoxy, ethoxy, n-propoxy, isopropoxy, n-butoxy, sec-butoxy, t-butoxy, and the like. The term "thioalkoxy" is similarly defined, except sulfur replaces oxygen.

The term "acyl" as used herein refers to an $R^eC(=O)$ group attached to the parent molecule through a carbonyl (C=O) group. $R^e$ is selected from the group consisting of alkyl, substituted alkyl, cycloalkyl, substituted cycloalkyl, aryl, substituted aryl, heteroaryl, substituted heteroaryl, heterocycloalkyl, and substituted heterocycloalkyl groups.

The term, "aryl" as used herein refers to monocyclic, fused bicyclic, and fused tricyclic carbocyclic aromatic ring systems including, but not limited to, phenyl, naphthyl, tetrahydronaphthyl, phenanthrenyl, biphenylenyl, indanyl, indenyl, anthracenyl, fluorenyl, and the like.

The term "heteroaryl" as used herein refers to monocyclic, fused bicyclic, and fused tricyclic aromatic ring systems, wherein one to four-ring atoms are selected from the group consisting of oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, thiophenyl, furanyl, quinolinyl, isoquinolinyl, benzoxazolyl, benzimidazolyl, benzothiazolyl, and the like.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl groups ring systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuryl, and the like.

The terms "substituted aryl," "substituted heteroaryl," and "substituted heterocycloalkyl" as used herein refer to an aryl, heteroaryl, or heterocycloalkyl group substituted by a replacement of one, two, or three of the hydrogen atoms thereon with a substitute selected from the group consisting of halo, $OR^d$, $N(R^d)_2$, $C(=O)N(R^d)_2$, CN, alkyl, substituted alkyl, mercapto, nitro, aldehyde, carboxy, carboxyl, carboxamide, aryl, substituted aryl, heteroaryl, substituted heteroaryl, cycloalkyl, substituted cycloalkyl, heterocycloalkyl, substituted heterocycloalkyl, $O(CH_2)_{1-3}N(R^d)_2$, $O(CH_2)_{1-3}CO_2H$, and trifluoromethyl.

The term "aldehyde" as used herein refers to a —CHO group.

The term "amino" as used herein refers an —$NH_2$ or —NH— group, wherein each hydrogen in each formula can be replaced with an alkyl, cycloalkyl, aryl, heteroaryl, heterocycloalkyl, substituted alkyl, substituted cycloalkyl, substituted aryl, substituted heteroaryl, or substituted heterocycloalkyl group, i.e., $N(R^e)_2$. In the case of —$NH_2$, the hydrogen atoms also can be replaced with substituents taken together to form a 5- or 6-membered aromatic or nonaromatic ring, wherein one or two carbons of the ring optionally are replaced with a heteroatom selected from the group consisting of sulfur, oxygen, and nitrogen. The ring also optionally can be substituted with an alkyl group. Examples of rings formed by substituents taken together with the nitrogen atom include, but are not limited to, morpholinyl, phenylpiperazinyl, imidazolyl, pyrrolidinyl, (N-methyl)piperazinyl, piperidinyl, and the like.

The term "carbamoyl" as used herein refers to a group of the formula —$NR^dC(=O)R^d$, —$OC(=O)N(R^d)_2$, and —$NR^dC(=O)$—, wherein $R^d$ is defined above.

The term "carbonyl" as used herein refers to a CO, C(O), or C(=O) group.

The term "carboxyl" as used herein refers to —$CO_2H$.

The term "carboxy" as used herein refers to a —$COOR^d$, wherein $R^d$ is defined above.

The term "carboxamide" as used herein refers to —$C(=O)N(R^g)_2$, wherein $R^g$ is defined as hydro, alkyl, substituted alkyl, aryl, substituted aryl, heteroaryl, substituted heteroaryl, heterocycloalkyl, substituted heterocycloalkyl, cycloalkyl, substituted cycloalkyl, or $OR^d$, or the $R^g$ groups are taken together with the nitrogen to which they are attached to form a five- or six-membered optionally substituted aromatic or nonaromatic ring, wherein one or two carbons of the ring optionally are replaced with a heteroatom selected from the group consisting of sulfur, oxygen, and nitrogen.

The term "thiocarboxamide" as used herein, refers to —$C(=S)N(R^g)_2$, wherein $R^g$ is defined above.

The term "mercapto" as used herein refers to —$SR^d$, wherein $R^d$ is defined above.

The term "sulfonamido" as used herein refers to —$NHSO_2R^g$, wherein $R^g$ is defined above.

The term "cyano" as used herein refers to a —C≡N group, also designated —CN.

The term "hydroxyamino" acs used herein refers to a —NHOH group.

The term "hydrazono" as used herein refers to a =N—$NH_2$ group, wherein one or both hydrogen atoms can be replaced with an alkyl or substituted alkyl group.

The terms "trifluoromethyl" and "trifluoromethoxy" as used herein refer to —$CF_3$ and —$OCF_3$, respectively.

The term "halo" as used herein refers to bromo, chloro, iodo, and fluoro.

The term "sulfonyl" as used herein refers to group represented by —$SO_2$— or —$SO_2R^d$, wherein $R^d$ is defined above.

The term "sulfamyl" as used herein refers to —$SO_2N(R^g)_2$, wherein $R^g$ is defined above.

The term "sulfo" as used herein refers to —$SO_3H$.

The term "nitro" as used herein refers to —$NO_2$.

In the structures herein, for a bond lacking a substituent, the substituent is methyl, for example,

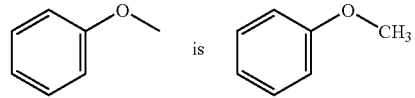

is

When no substituent is indicated as attached to a carbon atom on a ring, it is understood that the carbon atom contains the appropriate number of hydrogen atoms. In addition, when no substituent is indicated as attached to a carbonyl group or a nitrogen atom, for example, the substituent is understood to be hydrogen, e.g.,

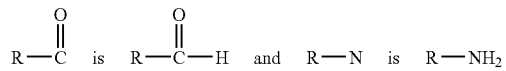

The abbreviation "Me" is methyl and Bn is benzyl.

The notation N(R$^x$)$_2$, wherein x represents an alpha or numeric character, such as, for example, R$^d$ is used to denote two R$^x$ groups attached to a common nitrogen atom. When used in such notation, the R$^x$ group can be the same or different, and is selected from the group as defined by the R$^x$ group.

DNA-PK Inhibitors

The present invention is directed to compounds that inhibit DNA-PK biological activity and having a formula (I) or (II). Preferred compounds are those of formula (I) and (II) wherein A is a morpholinyl, thiomorpholinyl, piperidinyl, piperazinyl, or tetrahydropyranyl group and L is absent. Other preferred DNA-PK inhibitors of formula (I) and (II), are those wherein:

m is 0, 1, or 2;

n is 0 or 1;

X is O, S(O)$_{0-2}$, or NR$^a$;

Z, independently, is CR$^b$ or N;

L is absent, or L is selected from the group consisting of —(CHR$^h$)$_p$—, —NR$^h$(CHR$^h$)$_p$—, —(CHR$^h$)—NR$^h$—NR$^h$, —C(=O)—, —O—, —NR$^h$(CO)—, —(CO)NR$^h$—, —S—, —SO—, —SO$_2$—, and —NR$^h$R$^q$, or —O(SO$_2$)CF$_3$ (provided A is absent), wherein p is an integer 1 to 5;

R$^h$ is selected from the group consisting of alkyl, aryl, and hydro;

R$^q$ is alkyl, optionally substituted with oxo, hydroxy, methoxy, benzyloxy, halo, aryl, or heteroaryl;

A is absent, or is heteroaryl or selected from the group consisting of a four- to seven-membered heterocyclic ring containing 1 or 2 heteroatoms independently selected from the group consisting of N and O;

m is 0, or R$^1$ is selected from the group consisting of halo, CF$_3$, OR$^d$, OC$_{1-3}$alkyleneN(R$^d$)$_2$, heterocycloalkyl, N(R$^d$)C$_{1-3}$alkyleneN(R$^d$)$_2$, OP(=O)—(OR$^d$)$_2$, OP(=O)(ONa)$_2$, substituted heterocycloalkyl, and OC$_{1-3}$alkyleneC(=O)OR$^d$;

n is 0, or R$^2$ is selected from the group consisting of OH, halo, CH$_2$OH, C(=O)NH$_2$, NH$_2$, OCH$_3$, NHC(=O)CH$_3$, NHCH$_3$, NO$_2$, O(CH$_2$)$_{1-3}$OH, O(C=O)heteroaryl, O(C=O)aryl, and O(C=O)alkyl;

R$^a$ is selected from the group consisting of hydro, C$_{1-4}$alkyl, aryl, heteroaryl, C(=O)R$^d$, C(=O)—N(R$^d$)$_2$, SO$_2$R$^d$, SO$_2$N(R$^d$)$_2$, and C$_{1-4}$alkyleneOR$^d$;

R$^b$, independently, is selected from the group consisting of hydro, OH, OR$^d$, O(C$_{1-3}$alkylene)(=O)(OR$^d$)$_2$, O(C$_{1-3}$alkylene)(=O)(ONa)$_2$, OP(=O)—(OR$^d$)$_2$, OP(=O)(ONa)$_2$, NO$_2$, NH$_2$, NHR$^d$, and halo.

Preferred compounds of the present invention have the following structures (III) and (IV), and prodrugs thereof:

(III)

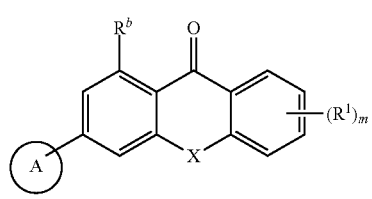

-continued (IV)

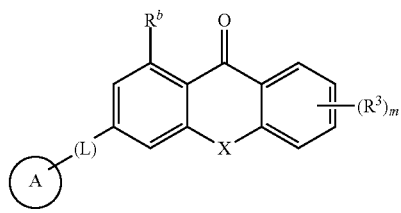

wherein X is O, NH, NC(=O)aryl, NC(=O)alkyl, NC$_{1-3}$alkylenearyl, or NC(=O)heteroaryl; m is 0, 1, or 2; and R$^1$ is halo, OR$^d$, heterocycloalkyl, substituted heterocycloalkyl, OC$_{1-3}$alkyleneO(=O)OR$^d$, N(R$^d$)C$_{1-3}$alkyleneN(R$^d$)$_2$, O(C$_{1-3}$alkylene)OP(=O)(OR$^d$)$_2$, O(C$_{1-3}$alkylene)OP(=O)(ONa)$_2$, OP(=O)(OR$^d$)$_2$, or OP(=O)—(ONa)$_2$. In especially preferred embodiments, A is selected from the group consisting of morpholinyl; L is absent or selected from the group consisting of —SO$_2$CF$_3$ and —OSO$_2$CF$_3$; X is selected from the group consisting of O, NH, NHC$_6$H$_5$, NC(=O)C$_{1-4}$alkyl,

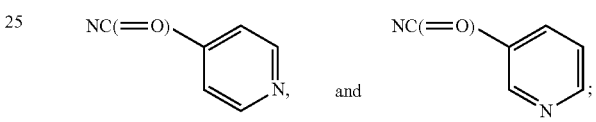

R$^1$ is selected from the group consisting of OH, OCH$_3$ OCH$_2$C(=O)OR$^d$, F, substituted

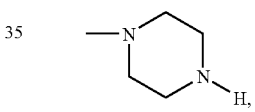

N(C$_{1-3}$alkyl)C$_{1-3}$alkylene(C$_{1-3}$alkyl)$_2$, OCH$_2$CH$_2$OP(=O)(OCH$_2$C$_6$H$_5$)$_2$, OCH$_2$CH$_2$OP(=O)(ONa)$_2$, OP(=O)(OCH$_2$C$_6$H$_5$)$_2$, and OP(=O)(ONa)$_2$; and R$^b$ is selected from the group consisting of H, OH, OCH$_2$CH$_2$OP(=O)(OCH$_2$C$_6$H$_5$)$_2$, OCH$_2$CH$_2$OP(=O)(ONa)$_2$, OP(=O)(OCH$_2$C$_6$H$_5$)$_2$, and OP(=O)(ONa)$_2$.

DNA-PK inhibitor compounds of the present invention can exist as stereoisomers having asymmetric or chiral centers. Stereoisomers are designated by either "S" or "R" depending on arrangement of substituents around a chiral carbon atom. Mixtures of stereoisomers are contemplated. Stereoisomers include enantiomers, diastereomers, and mixtures thereof. Individual stereoisomers can be prepared synthetically from commercially available starting materials that contain asymmetric or chiral centers, or by preparation of racemic mixtures followed by separation or resolution techniques well known in the art. Methods of resolution include (1) attachment of a mixture of enantiomers to a chiral auxiliary, separation of the resulting mixture by recrystallization or chromatography, and liberation of the optically pure product from the auxiliary, (2) salt formation employing an optically active resolving agent, and (3) direct separation of the mixture of optical enantiomers on chiral chromatographic columns.

The invention also provides prodrug forms of DNA-PK inhibitors of the invention. Prodrug design is discussed generally in Hardma et al., (Eds), *Goodman & Gilman's The Pharmacological Basis of Therapeutics*, Ninth Edition, New York, N.Y. (19966), pp. 11-16. Briefly, administration of a drug is followed by elimination from the body or some biotransformation whereby biological activity of the drug is reduced or eliminated. Alternatively, a biotransformation process can lead to a metabolic by-product which is more active or equally active compared to the drug initially administered. Increased understanding of these biotransformation processes permits the design of so-called "prodrugs" which, following a biotransformation, become more physiologically active in an altered state. Prodrugs are pharmacologically inactive or active compounds which are converted to biologically active or more active metabolites. In some forms, prodrugs are rendered pharmacologically active through hydrolysis, for example, of an ester or amide linkage, often introducing or exposing a functional group on the prodrug. The thus modified drug also can react with an endogenous compound to form a water soluble conjugate which further increases pharmacological properties of the compound, for example, an increased circulatory half-life.

As another alternative, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into circulation, thereby effectively increasing the biological half-life of the originally administered compound. Prodrugs are particularly useful for delivering a compound to a predetermined site of action, and modifications can be effected to facilitate targeting in this manner.

Pharmaceutical Compositions

The present invention also provides pharmaceutical compositions comprising one or more DNA-PK inhibitors of formula (I) or (II). The pharmaceutical compositions comprise a DNA-PK inhibitor of formula (I) or (II) in a pharmaceutically acceptable carrier or diluent, including, but not limited to, preferred compounds of formula (I) or (II). The invention also provides pharmaceutical compositions containing a compound of formula (I) or (II) in combination with an antineoplastic agent.

In a preferred embodiment, the pharmaceutical compositions comprise one or more DNA-PK inhibitor compounds including, but not limited to, compounds set forth below in the examples.

In one aspect, the pharmaceutical compositions comprise a compound of formula (I) or (II) and one or more antineoplastic agents. In a preferred embodiment, the composition comprises a chemotherapeutic agent, a radiotherapeutic agent, or a combination thereof in a pharmaceutically acceptable carrier or diluent. Examples of antineoplastic agents, including chemotherapeutic and radiotherapeutic agents, suitable for use with a DNA-PK inhibitor of the present invention include, but are not limited to, compounds included in the following table.

| CHEMOTHERAPEUTIC AGENTS |
|---|
| Alkylating agents |
| Nitrogen mustards |
| mechlorethamine |
| cyclophosphamide |
| ifosfamide |
| melphalan |
| chlorambucil |

| CHEMOTHERAPEUTIC AGENTS |
|---|
| Nitrosoureas |
| carmustine (BCNU) |
| lomustine (CCNU) |
| semustine (methyl-CCNU) |
| Ethylenimine/Methylmelamine |
| triethylenemelamine (TEM) |
| triethylene thiophosphoramide (thiotepa) |
| hexamethylmelamine (HMM, altretamine) |
| Alkly sulfonates |
| busulfan |
| Triazines |
| dacarbazine (DTIC) |
| Antimetabolites |
| Folic Acid analogs |
| methotrexate |
| trimetrexate |
| Pyrimidine analogs |
| 5-fluorouracil |
| fluorodeoxyuridine |
| gemcitabine |
| cytosine arabinoside (AraC, cytarabine) |
| 5-azacytidine |
| 2,2'-difluorodeoxycytidine |
| Purine analogs |
| 6-mercaptopurine |
| 6-thioguanine |
| azathioprine |
| 2'-deoxycoformycin (pentostatin) |
| erythrohydroxynonyladenine (EHNA) |
| fludarabine phosphate |
| 2-chlorodeoxyadenosine (cladribine, 2-cdA) |
| Type I Topoisomerase Inhibitors |
| camptothecin |
| topotecan |
| irinotecan |
| Natural products |
| Antimitotic drugs |
| paclitaxel |
| Vinca alkalids |
| vinblastine (VLB) |
| vincristine |
| vinorelbine |
| TAXOTERE ® (docetaxel) |
| estramustine |
| estramustine phosphate |
| Epipodophylotoxins |
| etoposide |
| teniposide |
| Antibiotics |
| actimomycin D |
| daunomycin (rubidomycin) |
| doxorubicin (adriamycin) |
| mitoxantrone |
| idarubicin |
| bleomycins |
| plicamycin (mithramycin) |

| CHEMOTHERAPEUTIC AGENTS |
| --- |
| mitomycin C |
| dactinomycin |
| Enzymes |
| |
| L-asparaginase |
| Biological response |
| modifiers |
| |
| interferon-alph |
| IL-2 |
| G-CSF |
| GM-CSF |
| Differentiation Agents |
| |
| retinoic acid |
| derivatives |
| Radiosensitizers |
| |
| metronidazole |
| misonidazole |
| desmethylmisonidazole |
| pimonidazole |
| etanidazole |
| nimorazole |
| RSU 1069 |
| EO9 |
| RB6145 |
| SR4233 |
| nicotinamide |
| 5-bromodeoxyuridine |
| 5-iododeoxyuridine |
| bromodeoxycytidine |
| Miscellaneous agents |
| Platinum coordination |
| complexes |
| |
| cisplatin |
| carboplatin |
| Anthracenedione |
| |
| mitoxantrone |
| Substituted urea |
| |
| hydroxyurea |
| Methylhydrazine |
| deriavtives |
| |
| N-methylhydrazine (MIH) |
| procarbazine |
| Adrenocortical |
| suppressant |
| |
| mitotane (o,p'-DDD) |
| aminoglutethimide |
| Cytokines |
| |
| interferon (α, β, γ) |
| interleukin-2 |
| Hormones and |
| antagonists |
| Adrenocorticosteroids/ |
| antagonists |
| |
| prednisone and |
| equivalents |
| dexamethasone |
| aminoglutethimide |
| Progestins |
| |
| hydroxyprogesterone |
| caproate |
| medroxyprogesterone |
| acetate |
| megestrol acetate |

| CHEMOTHERAPEUTIC AGENTS |
| --- |
| Estrogens |
| |
| diethylstilbestrol |
| ethynyl |
| estradiol/equivalents |
| Antiestrogen |
| |
| tamoxifen |
| Androgens |
| |
| testosterone propionate |
| fluoxymesterone/equivalents |
| Antiandrogens |
| |
| flutamide |
| gonadotropin-releasing |
| hormone analogs |
| leuprolide |
| Nonsteroidal |
| antiandrogens |
| |
| flutamide |
| Photosensitizers |
| |
| hematoporphyrin |
| derivatives |
| PHOTOFRIN ® |
| benzoporphyrin |
| derivatives |
| Npe6 |
| tin etioporphyrin |
| (SnET2) |
| pheoboride-a |
| bacteriochlorophyll-a |
| naphthalocyanines |

Depending on the neoplastic condition, pharmaceutical compositions of the invention can be formulated to include one or more cytokines, lymphokines, growth factors, or other hematopoietic factors which can lessen the adverse side effects that arise from, or are associated with, administration of the pharmaceutical composition alone. Cytokines, lymphokines, growth factors, or other hematopoietic factors particularly useful in pharmaceutical compositions of the present invention include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF, G-CSF, Meg-CSF, GM-CSF, thrombopoietin, stem cell factor, erythropoietin, angiopoietins, including Ang-1, Ang-2, Ang-4, Ang-Y, and/or the human angiopoietin-like polypeptide, vascular endothelial growth factor, (VEGF), angio-genin, bone morphogenic protein-1 (BMP-1), BMP-2, BMP-3, BMP-4, BMP-5, BMP-6, BMP-7, BMP-8, BMP-9, BMP-10, BMP-11, BMP-12, BMP-13, BMP-14, BMP-15, BMP receptor IA, BMP receptor IB, brain derived neurotrophic factor, ciliary neutrophic factor, ciliary neutrophic factor receptor a cytokine-induced neutrophil chemotactic factor 1, cytokine-induced neutrophil chemotactic factor 2 α, cytokine-induced neutrophil chemotactic factor 2 β, β endothelial cell growth factor, endothelin 1, epidermal growth factor, epithelial-derived neutrophil attractant, fibroblast growth factor (FGF) 4, FGF 5, FGF 6, FGF 7, FGF 8, FGF 8b, FGF 8c, FGF 9, FGF 10, FGF acidic, FGF basic, glial cell line-derived neutrophic factor receptor α 1, glial cell line-derived neutrophic factor receptor α 2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor, stem cell factor receptor, transforming growth factor (TGF) α, TGF β, TGF β1, TGF β1.2, TGF β2, TGF β3, TGF β5, latent TGF β1, TGF β, binding protein I, TGF β binding protein II, TGF β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

The therapeutic index of compositions comprising a compound of the invention can be enhanced by conjugation of the compound with antitumor antibodies as previously described (for example, Pietersz et al., *Immunol. Rev.*, 129:57 (1992); Trail et al., *Science* 261:212 (1993); Rowlinson-Busza et al., *Curr. Opin. Oncol.*, 4:1142 (1992)). Tumor directed delivery of compounds of the present invention enhances a therapeutic benefit by minimizing potential nonspecific toxicities that can result from radiation treatment or chemotherapy. In another aspect, DNA-PK inhibitor compounds and radioisotopes or chemotherapeutic agents can be conjugated to the same antibody molecule. Alternatively, DNA-PK inhibitor-conjugated-tumor specific antibodies can be administered before, during, or after administration of chemotherapeutic-conjugated antitumor antibody or radioimmunotherapy.

Methods of Inhibiting DNA-PK

The invention further provides methods of inhibiting DNA-PK activity comprising the step of contacting DNA-PK or a biologically active fragment thereof, with one or more compounds of structural formula (I) or (II). Nonlimiting examples of compounds useful in the method include, but are not limited to, compounds set forth in the examples. Methods of the present invention include in vivo, in vitro, and ex vivo applications. Cells useful in the methods include those that express endogenous DNA-PK enzymes, "endogenous" indicating that the cells express DNA-PK absent recombinant introduction into the cells of one or more polynucleotides encoding a DNA-PK enzyme or a biologically active fragment thereof. The methods also contemplate use of cells that express exogenous DNA-PK, wherein one or more polynucleotides encoding a DNA-PK enzyme or biologically active fragment thereof have been introduced into the cell using recombinant procedures. In another aspect; the methods include use of cancer cells. In a preferred embodiment, the methods include use of mammalian cancer cells, and in a most preferred method, the mammalian cancer cells are human cancer cells.

In vitro methods comprising a step of contacting DNA-PK with an inhibitor of the invention also are contemplated. The DNA-PK enzyme of an in vitro method can include a purified and isolated enzyme, wherein the enzyme is isolated from natural sources (i.e., cells or tissues that normally express a DNA-PK enzyme absent modification by recombinant technology) or isolated from cells modified by recombinant techniques to express an exogenous enzyme.

Methods of Identifying DNA-PK Inhibitors

The invention also provides methods of identifying DNA-PK inhibitors comprising the steps of a) measuring DNA-PK enzyme activity in the presence and absence of a test compound, and b) identifying the test compound as a DNA-PK inhibitor when DNA-PK enzyme activity is decreased in the presence of the test compound. The invention contemplates in vivo and in vitro methods. In one aspect, purified and isolated DNA-PK is utilized in the method. The enzyme can be obtained from cells that naturally express the enzyme, or, alternatively, the enzyme can be obtained from cells transformed or transfected with exogenous DNA that encodes the DNA-PK enzyme. As another alternative, the enzyme can be purchased from commercial sources. In in vivo assays cells that naturally express the DNA-PK enzyme are utilized.

Compounds that inhibit DNA-PK activity can be identified by incubating a test compound with a DNA-PK polypeptide and determining the effect of the test compound on DNA-PK activity. The selectivity of a compound that inhibits the enzyme activity can be evaluated by comparing its effects on DNA-PK to its effect on other kinase enzymes.

Selective modulators include, for example, antibodies and other proteins or peptides which specifically bind to a DNA-PK polypeptide, oligonucleotides which specifically bind to a DNA-PK polypeptide or a DNA-PK gene sequence, and other nonpeptide compounds (e.g., isolated or synthetic organic and inorganic molecules) which specifically react with a DNA-PK polypeptide or a nucleic acid encoding the polypeptide. Presently preferred targets for the development of selective inhibitors include, for example: (1) regions of the DNA-PK polypeptide that contact other proteins, (2) regions that localize the DNA-PK polypeptide within a cell wherein localization is required for specific kinase activity, (3) regions of the DNA-PK polypeptide that bind substrate, (4) regions of the polypeptide that bind DNA and result in activation of kinase activity. Inhibitors of DNA-PK activity are therapeutically useful in treatment of a wide range of diseases and physiological conditions as described herein.

Methods of identifying DNA-PK inhibitors include variations of any of the methods known in the art to identify binding partner compounds, including techniques wherein a binding partner compound (e.g., a substrate molecule or a DNA sequence that activates the kinase) has been identified and a binding assay is carried out in the presence and absence of a test inhibitor compound. An inhibitor can be identified in those instances where the level of binding between the DNA-PK polypeptide and the binding partner compound changes in the presence of the test compound compared to the level of binding in the absence of the candidate modulator compound.

In addition to the assays described above, other methods that specifically identify DNA-PK inhibitors are contemplated. In one aspect, the methods utilize the split hybrid assay, as generally described in WO 98/13502. The invention also embraces variations on this method, as described in WO 95/20652.

The present invention also contemplates high throughput screening (HTS) assays to identify compounds that inhibit DNA-PK biological activity (e.g., inhibit enzymatic activity, binding activity etc.). HTS assays permit screening of large numbers of compounds in an efficient manner. Cell-based HTS systems are contemplated, including melanophore assays to investigate receptor-ligand interaction, yeast-based assay systems, and mammalian cell expression systems (Jayawickreme et al., *Curr. Opin. Biotechnol.*, 8:629-634 (1997)). Automated and miniaturized HTS assays are also embraced (Houston et al., *Curr. Opin. Biotechnol.*, 8:734-740 (1997)). HTS assays are designed to identify "hits" or "lead compounds" having the desired property, from which modifications can be designed to improve the desired property. Chemical modification of the "hit" or "lead compound" often is based on an identifiable structure/activity relationship between the "hit" and the DNA-PK polypeptide.

There are a number of different libraries used for the identification of compounds, and in particular small molecules, that modulate (i.e., increase or decrease) biological activity of a polypeptide of the invention, including, (1) organic and inorganic chemical libraries, (2) natural product libraries, and (3) combinatorial libraries comprised of random peptides, oligonucleotides or organic molecules.

Chemical libraries can, be synthesized readily, or purchased from commercial sources, and consist of structural analogs of known compounds or compounds that are identified as "hits" or "leads" via natural product screening. The sources for natural product libraries are collections from microorganisms (including bacteria and fungi), animals, plants and other vegetation, or marine organisms which are used to create mixtures for screening by: (1) fermentation and extraction of broths from soil, plant or marine microorganisms or (2) extraction of plants or marine organisms. Natural product libraries include polyketides, nonribosomal peptides, and variants (nonnaturally occurring) variants thereof. For a review, see *Science,* 282:63-68 (1998). Combinatorial libraries are composed of large numbers of peptides, oligonucleotides, peptide nucleic acids, or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.,* 8:701-707 (1997).

Identification of modulators through use of the various libraries described herein permits modification of the candidate "hit" (or "lead") to optimize the capacity of the "hit" to modulate activity. Compounds identified in the binding assays then are tested for antagonist or agonist activity in in vivo tissue culture or animal models that are well known in the art.

The present invention also provides methods of characterizing the potency of a test compound as an inhibitor of a DNA-PK polypeptide, said method comprising the steps of: (a) measuring activity of a DNA-PK polypeptide in the presence of a test compound; (b) comparing the activity of the DNA-PK polypeptide in the presence of the test compound to the activity of the DNA-PK enzyme in the presence of an equivalent amount of a reference compound of formula (I) or (II), wherein a lower activity of the DNA-PK polypeptide in the presence of the test compound than in the presence of the reference compound indicates that the test compound is a more potent inhibitor than the reference compound, and a higher activity of the DNA-PK polypeptide in the presence of the test compound than in the presence of the reference compound indicates that the test compound is a less potent inhibitor than the reference compound.

The present invention further provides methods of characterizing the potency of a test compound as an inhibitor of a DNA-PK polypeptide, said method comprising the steps of: (a) determining an amount of a control compound of formula (I) or (II) that inhibits an activity of a DNA-PK polypeptide by a reference percentage of inhibition, thereby defining a reference inhibitory amount for the control compound; (b) determining an amount of a test compound that inhibits an activity of a DNA-PK polypeptide by a reference percentage of inhibition, thereby defining a reference inhibitory amount for the test compound; (c) comparing the reference inhibitory amount for the test compound to a reference inhibitory amount determined according to step (a) for the control compound of formula (I) or (II), wherein a lower reference inhibitory amount for the test compound than for the control compound indicates that the test compound is a more potent inhibitor than the control compound, and a higher reference inhibitory amount for the test compound than for the control compound indicates that the test compound is a less potent inhibitor than the control compound. In one aspect, the method utilizes a reference inhibitory amount which is the amount of the compound that inhibits the activity of the DNA-PK polypeptide by 50%, by 60%, by 70%, or by 80%. In another aspect, the method employs a reference inhibitory amount that is the amount of the compound that inhibits the activity of the DNA-PK polypeptide by 90%, by 95%, or by 99%. A method of the present invention comprise determining the reference inhibitory amount of the test compound in an in vitro biochemical assay, determining the reference inhibitory amount of the test compound in an in vitro cell-based assay, or determining the reference inhibitory amount of the test compound in an in vivo assay.

Therapeutic Methods

The present invention further provides methods of sensitizing a cell to an agent that induces a DNA lesion comprising a step of contacting the cell with one or more DNA-PK inhibitors of formula (I) or (II). Some nonlimiting preferred compounds are set forth in the examples. In presently preferred methods, an agent that induces a DNA lesion is selected from the group consisting of radiation, exogenous chemicals, metabolite by-products, and combinations thereof. Particularly preferred methods include use of one or more chemotherapeutic/antineoplastic agents as set out in the above table that induce DNA lesions.

The invention further provides methods of potentiating a therapeutic regimen for treatment of cancer comprising the step of administering to an individual in need thereof an effective amount of a DNA-PK inhibitor of formula (I) or (II). In one aspect, methods include those wherein the therapeutic regimen for treatment of cancer is selected from the group consisting of chemotherapy, radiation therapy, and a combination chemotherapy and radiation therapy. In methods wherein the therapeutic regimen includes chemotherapy, the DINA-PK inhibitor is administered before, concurrently with, and/or after administration of the chemotherapeutic/antineoplastic agent. In one aspect, methods include use of one or more chemotherapeutic/antineoplastic agents selected from the group consisting of those compounds set out in the table above. In another aspect of the invention, the DNA-PK inhibitor is administered before, concurrently with, or after administration of a cytokine, lymphokine, growth factor, or hematopoietic factor as described herein.

Compounds of the invention are useful when radiation and chemotherapy are indicated in order to enhance the therapeutic benefit of these treatments, including induction chemotherapy, primary (neoadjuvant) chemotherapy, and both adjuvant radiation therapy and adjuvant chemotherapy. In addition, radiation and chemotherapy frequently are indicated as adjuvants to surgery in the treatment of cancer. The goal of radiation and chemotherapy in the adjuvant setting is to reduce the risk of recurrence and enhance disease-free survival when the primary tumor has been controlled. Chemotherapy is utilized as a treatment adjuvant for colon, lung, and breast cancer, frequently when the disease is metastatic. Adjuvant radiation therapy is indicated in several diseases including colon, lung, and breast cancers as described above. For example, radiation frequently is used both pre- and post-surgery as components of the treatment strategy for rectal carcinoma. Compounds of the invention therefore are particularly useful following surgery in the treatment of cancer in combination with radio- and/or chemotherapy.

The present invention further relates to radiosensitizing tumor cells utilizing a compound of formula (I) or (II). Non-limiting examples of the compounds suitable for use in the method include, but are not limited to, compounds disclosed in the examples. A compound that can "radiosensitize" a cell, as used herein, is defined as a molecule, preferably a low molecular weight molecule, administered to animals in a therapeutically effective amount to increase the sensitivity of cells to electromagnetic radiation and/or to promote the treatment of diseases that are treatable with electromagnetic radiation. Diseases that are treatable with electromagnetic radiation include neoplastic diseases, benign and malignant tumors, and cancerous cells.

Electromagnetic radiation treatment of other diseases not listed herein is also contemplated by the present invention. The terms "electromagnetic radiation" and "radiation" as used herein include, but are not limited to, radiation having the wavelength of $10^{-20}$ to 1 meter. Preferred embodiments of the present invention employ the electromagnetic radiation of: gamma radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Several mechanisms for the mode of action of radiosensitizers have been suggested. Hypoxic cell radiosensitizers (e.g., 2-nitroimidazole compounds and benzotriazine dioxide compounds) promote reoxygenation of hypoxic tissue and/or catalyze generation of damaging oxygen radicals. Nonhypoxic cell radiosensitizers (e.g., halogenated pyrimidines) can be analogs of DNA bases, preferentially that incorporate into the DNA of cancer cells and thereby promote the radiation ion-induced breaking of DNA molecules and/or prevent the normal DNA repair mechanisms. Various other potential mechanisms of action have been hypothesized for radiosensitizers in the treatment of disease.

Many cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives thereof.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more other compounds, including but not limited to, compounds that promote the incorporation of radiosensitizers to the target cells; compounds that control the flow of therapeutics, nutrients, and/or oxygen to the target cells; chemotherapeutic agents that act on the tumor with or without additional radiation; or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO. Examples of chemotherapeutic agents that can be used in conjunction with radiosensitizers include, but are not limited to, adriamycin, camptothecin, carboplatin, cisplatin, daunorubicin, doxorubicin, interferon (alpha, beta, gamma), interleukin 2, irinotecan, docetaxel, paclitaxel, topotecan, and therapeutically effective analogs and derivatives thereof.

The invention also can be practiced by including another anticancer chemotherapeutic agent with a compound of the invention, such as any conventional chemotherapeutic agent. The combination of the inhibitor compound with such other agents can potentiate the chemotherapeutic protocol. Numerous chemotherapeutic protocols known to the skilled practitioner as being capable of incorporation into the method of the invention. Any chemotherapeutic agent can be used, including alkylating agents, antimetabolites, hormones and antagonists, radioisotopes, as well as natural products. For example, the inhibitor compound of the invention can be administered with antibiotics, such as doxorubicin and other anthracycline analogs, nitrogen mustards, such as cyclophosphamide, pyrimidine analogs, such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery, radiation, also referred to herein as "adjunct antineoplastic modalities." Thus, the method of the invention can be employed with such conventional regimens with the benefit of reducing side effects and enhancing efficacy.

The present invention also provides methods of treating cancer in an animal, comprising administering to the animal an effective amount of a compound that inhibits DNA-PK activity, such as a compound of formula (I) or (II) the present invention also is directed to methods of inhibiting cancer cell growth, including processes of cellular proliferation, invasiveness, and metastasis in biological systems. Methods include use of a compound of formula (I) or (II) as an inhibitor of cancer cell growth. Preferably, the methods are employed to inhibit or reduce cancer cell growth, invasiveness, metastasis, or tumor incidence in living animals, such as mammals. Methods of the invention also are readily adaptable for use in assay systems, e.g., assaying cancer cell growth and properties thereof, as well as identifying compounds that affect cancer cell growth.

Compounds of the present invention possess one or more desirable, but unexpected, combinations of properties, including increased activity and/or solubility, and reduction of adverse side effects. These compounds have been found to inhibit cancer growth, including proliferation, invasiveness, and metastasis, thereby rendering them particularly desirable for the treatment of cancer. In particular, compounds of the invention exhibit cancer-inhibitory properties at concentrations that appear to be substantially free of side effects. These compounds therefore are useful for extended treatment protocols, where the use of conventional chemotherapeutic compounds can exhibit undesirable side effects. For example, the coadministration of a compound of the invention with another, more toxic, chemotherapeutic agent can achieve beneficial inhibition of a cancer, while effectively reducing the toxic side effects in the patient.

In addition, the properties of hydrophilicity and hydrophobicity of the compounds of the invention are well balanced, thereby enhancing their utility for both in vitro and especially in vivo uses, while other compounds lacking such balance are of substantially less utility. Specifically, compounds of the invention have an appropriate degree of solubility in aqueous media which permits absorption and bioavailability in the body, while also having a degree of solubility in lipids which permits the compounds to traverse the cell membranes, including the nuclear membrane, to a putative site of action. Thus, compounds of the invention are maximally effective when delivered to the site of the tumor and they enter the tumor cells.

The cancers treatable by methods of the present invention typically occur in mammals. Mammals include, for example, humans and other primates, as well as pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that, they show a greater loss of differentiation (greater "dedifferentiation") and their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells which infiltrate (invade) the surrounding tissues and give rise to metastases. Adenocarcinomas are carcinomas derived from glandular tissue, or from tissues which form recognizable glandular structures. Another broad category of cancers includes sarcomas, which are tumors whose cells are embedded in a fibrillar or homogeneous substance like embryonic connective tissue. The invention also enables treatment of cancers of the myeloid or lymphoid systems, including leukemias, lymphomas, and other cancers that typically are not present as a tumor mass, but are distributed in the vascular or lymphoreticular systems.

DNA-PK activity can be associated with various forms of cancer in, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the headland neck, esophageal squamous cell carcinoma, oral carcinoma, blood cell malignancies, including multiple myeloma, leukemias, including acute lymphocytic leukemia, acute nonlymphocytic leukemia, chronic kymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastro-intestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital, tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, Wilms' tumors, gall bladder cancer, trophoblastic neoplasms, hemangiopericytoma, and Kaposi's sarcoma. Methods to potentiate treatment of these and other forms of cancer are embraced blithe invention.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it should be understood that the method of the invention is not limited to the treatment of these tumor types, but extends to any tumor derived from any organ system. Cancers whose invasiveness or metastasis is associated with DNA-PK expression or activity are especially susceptible to being inhibited or even induced to regress by means of the invention.

In addition to the neoplastic conditions described above, DNA-PK activity can be correlated with other pathologies including aberrant apoptotic mechanisms, such as abnormal caspase activity; aberrant enzyme activity associated with cell cycle progression, include for example cyclins A, B, D and E; alterations in viral (e.g., Epstein-Barr virus, papilloma virus) replication in latently infected cells; chromosome structure abnormalities, including genomic stability in general, unrepaired chromosome damage, telomere erosion (and telomerase activity), breakage syndromes including for example, Sjögren's syndrome, Bloom's syndrome, and Nijmegen breakage syndrome; embryonic stem cell lethality; abnormal embryonic development; sensitivity to ionizing radiation; acute immune complex alveolitis; and Fanconi anemia. Treatment of these pathological conditions, and others that arise from enhanced DNA-PK activity, also is embraced by the invention.

The present invention also includes methods to inhibit retroviral infection utilizing a compound of the invention. DNA-PK participates in nonhomologous end joining (NHEJ) of chromosomal DNA and retroviral DNA integration into the host genome in accomplished through this type of NHEJ reaction (Daniel et al., *Science*, 284:644-647 (1999)). Inhibition of DNA-PK therefore can prevent retroviral DNA from integrating into the host genome in infected cells. Because retroviral genomic integration occurs after infections, it is unlikely that inhibition of DNA-PK affects early stages of infection. Instead, inhibiting DNA-PK prevents repair of chromosomal breakage associated with integration and therefore signal apoptosis for the infected cell. Assays to assess the ability of DNA-PK inhibitors to act in this manner can be carried out by measuring apoptosis with virally infected cells in the presence and absence of a DNA-PK inhibitor.

Because many anticancer drugs are also immunosuppressive, the DNA-PK inhibitors also can be used to potentiate the efficacy of drugs in the treatment of inflammatory diseases. In particular, the method of the invention can be employed to treat humans therapeutically or prophylactically who are or may subject to an inflammatory disorder. "Inflammatory disorder" as used herein can refer to any disease, disorder, or syndrome in which an excessive or unregulated inflammatory response leads to excessive inflammatory symptoms, host tissue damage, or loss of tissue function. "Inflammatory disorders" can also refer to pathological states mediated by influx of leukocytes and or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and or neutrophil chemotaxis. Inflammation can result from infection with pathogenic organisms and viruses and from noninfectious means, such as trauma or reperfusion following myocardial infarction or stroke, immune response to foreign antigen, and autoimmune responses. Accordingly, inflammatory disorders amenable to the invention encompass disorders associated with reactions of the specific defense system as well as with reactions of the nonspecific defense system.

As used herein, the term "specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD) are further examples of inflammatory reactions of the specific defense system.

The term "nonspecific defense system" as used herein refers to inflammatory disorders that are mediated by leukocytes that are incapable of immunological memory (e.g., granulocytes, macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents. "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue (including organs or cells, e.g., bone marrow), characterized by a loss of function of the grafted and surrounding tissues, pain, swelling, leukocytosis, and thrombocytopenia.

The therapeutic methods of the present invention include methods for the amelioration of disorders associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The present invention enables methods of treating various diseases associated with or characterized by inflammation, for example, arthritic diseases, such as rheumatoid arthritis, osteoarthritis, gouty arthritis, spondylitis; Behcet's disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders, such as allergic conjunctivitis, vernal conjunctivitis, uveitis, and thyroid-associated ophthalmopathy; eosinophilic granuloma; pulmonary or respiratory disorders, such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, pneumonia, bronchiectasis, and pulmonary oxygen toxicity; reperfusion injury of the myocardium, brain, or extremities; fibrosis, such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; transplant rejection disorders, such as GVHD and allograft rejection; chronic glomerulonephritis; inflammatory bowel diseases, such as Crohn's disease, ulcerative colitis and necrotizing enterocolitis; inflammatory dermatoses, such as contact dermatitis, atopic dermatitis, psoriasis, or urticaria; fever and myalgias due to infection; central or peripheral nervous system inflammatory disorders, such as meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion associated syndromes; and cytokine-induced toxicity.

Methods of the invention can be used with animal models in order to assess the efficacy of compounds of the invention. For example, animal models used in the study of inflammatory bowel disease (IBD) are generally elicited by intrarectal administration of noxious irritants (e.g., acetic acid or trinitrobenzene sulfonic acid/ethanol). Colonic inflammation induced by these agents is the result of chemical or metabolic injury and lacks the chronic and spontaneously relapsing inflammation associated with human IBD. However, a recently described model using subserosal injections of purified peptidoglycan-polysaccharide (PG-PS) polymers from either group A or group D streptococci appears to be a more physiologically relevant model for human IBD (Yamada et al., *Gastroenterology*, 104:759-771 (1993)).

In this model, PG-PS is injected into the subserosal layer of the distal colon. The resulting inflammatory response is biphasic with an initial acute episode three days after injection, which is followed by a spontaneous chronic phase three to four weeks later. The late phase response is granulomatous in nature, and results in colonic thickening, adhesions, colonic nodules and mucosal lesions. In general, granulomatous lesions are the result of chronic inflammation which leads to the recruitment and subsequent activation of cells of the monocyte/macrophage lineage. In addition to mucosal injury, PG-PS colitis frequently leads to arthritis, anemia, and granulomatous hepatitis. The extraintestinal manifestations of the disease make the model attractive for studying Crohn's colitis in that a significant number of patients with active Crohn's disease suffer from arthritic joint disease and hepatobiliary inflammation.

Methods of the invention have particular utility in treating humans who are or may be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of DNA-PK expression or activity will result in reduced amounts of reperfusion injury in such situations.

With respect to the nervous system, global ischemia occurs when blood flow to the entire brain ceases for a period. Global ischemia can result from cardiac arrest. Focal ischemia occurs when a portion of the brain is deprived of its normal blood supply. Focal ischemia can result from thromboembolic occlusion of a cerebral vessel, traumatic head injury, edema, or brain tumor. Even if transient, both global and focal ischemia can cause widespread neuronal damage. Although nerve tissue damage occurs over hours or even days following the onset of ischemia, some permanent nerve tissue damage ray develop in the initial minutes following the cessation of blood flow to the brain. Much of this damage has been attributed to glutamate toxicity and to the secondary consequences of tissue reperfusion, such as the release of vasoactive products by damaged endothelium and the release of cytotoxic products, such as free radicals and leukotrienes, by the damaged tissue.

Ischemia also can occur in the heart in myocardial infarction and other cardiovascular disorders in which the coronary arteries have been obstructed as a result of atherosclerosis, thrombus, or spasm. For example, the method of the invention can be useful for treating cardiac tissue damage, particularly damage resulting from cardiac ischemia or caused by reperfusion injury in mammals.

Administration

The compounds and pharmaceutical compositions of the invention can be administered to humans and other animals by any suitable route. For example, the compositions can be administered orally, including sublingually, rectally, parenterally, intracisternally, intravaginally, intraperitoneally topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention under the splenic capsule, brain, or in the cornea.

Compounds of the present invention also can be administered in the form of liposomes. As is known in the art, liposomes generally are derived from phospholipids or other lipid substances. Liposomes are formed by mono- or multilamellar hydrated liquid crystals that are dispersed in an aqueous medium. Any nontoxic, physiologically acceptable, and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology, Volume XIV*, Academic Press, New York, N.Y. (1976), p. 33, et seq.

The compounds of the present invention can be used in the form of pharmaceutically acceptable salts derived from inorganic or organic acids. By "pharmaceutically acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 66:1 (1977). The salts can be prepared in situ during the final isolation and purification of the compounds of the invention or separately by reacting a free base function with a suitable acid.

Representative acid addition salts include, but are not limited to acetate, adipate, alginate, citrate, aspartate, benzoate, benzenesulfonate, bisulfate, butyrate, camphorate, camphorolsulfonate, digluconate, glycerophosphate, hemisulfate, heptanoate, hexanoatey fumarate hydrochloride, hydrobromide, hydroiodide, 2-hydroxyethanesulfonate (isothienate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Examples of acids that can be employed to form pharmaceutically acceptable acid addition salts include inorganic acids, such as hydrochloric acid, hydrobromic acid, sulfuric acid, and phosphoric acid, and organic acids, such as oxalic acid, maleic acid, succinic acid, and citric acid.

Basic nitrogen-containing groups can be quaternized with such agents as lower alkyl halides such as methyl, ethyl, propyl, and butyl chlorides, bromides, and iodides; dialkyl sulfates like dimethyl, diethyl, dibutyl and diamyl sulfates; long chain halides such as decyl, lauryl, myristyl, and stearyl chlorides, bromides, and iodides; and arylalkyl halides, like benzyl and phenethyl bromides and others. Water or oil-soluble or dispersible products thereby are obtained.

Basic addition salts can be prepared in situ during the final isolation and purification of compounds of this invention by reacting a carboxylic acid-containing moiety with a suitable base, such as a hydroxide, carbonate, or bicarbonate of a pharmaceutically acceptable metal cation or with ammonia or organic primary, secondary, or tertiary amine. Pharmaceutically acceptable basic addition salts include, but are not limited to, cations based on alkali metals or alkaline earth metals, such as lithium, sodium, potassium, calcium, magnesium, and aluminum, and the like, and nontoxic quaternary ammonia and amine cations including ammonium, tetramethylammonium, tetraethylammonium, methylamine, dimethylamine, trimethylamine, ethylamine, diethylamine, triethylamine, and the like. Other representative organic amines useful for the formation of base addition salts include ethylenediamine, ethanolamine, diethanolamine, piperidine, piperazine, and the like.

Dosage forms for topical administration of a compound of this invention include powders, sprays, ointments, and inhalants as described herein. The active compound is mixed under sterile conditions with a pharmaceutically acceptable carrier and any needed preservatives, buffers, or propellants which may be required. Ophthalmic formulations, eye ointments, powders, and solutions also are contemplated as being within the scope of this invention.

Parenteral Administration

Pharmaceutical compositions of the invention for parenteral injection comprise pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters, such as ethyl oleate. Proper fluidity can be maintained, for example, by the use of coating materials such as lecithin, by the maintenance of the required particle size in the case of dispersions, and by the use of surfactants.

These compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol, sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the drug, it is desirable to slow absorption of the drug from subcutaneous or intramuscular injection. This result can be accomplished by the use of a liquid suspension of crystalline or amorphous materials with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the drug in biodegradeable polymers, such a polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

Oral Administration

The invention provides methods for oral administration of a pharmaceutical composition of the invention. Oral solid dosage forms are described generally in *Remington's Pharmaceutical Sciences*, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation can include liposomes that are derivatized with various polymers (e.g., U.S. Pat. No. 5,013,556). In general, the formulation includes a compound of the invention and inert ingredients which protect against degradation in the stomach and which permit release of the biologically active material in the intestine.

In such solid dosage forms, the active compound is mixed with, or chemically modified to include, a least one inert, pharmaceutically acceptable excipient or carrier. The excipient or carrier preferably permits (a) inhibition of proteolysis, and (b) uptake into the blood stream from the stomach or intestine. In a most preferred embodiment, the excipient or carrier increases uptake of the compound, overall stability of the compound and/or circulation time of the compound in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO™, EMDEX™, STA-RX 1500™, EMCOMPRESS™ and AVICEL™; (b) binders such as, for example, methylcellulose ethylcellulose, hydroxypropyl-methyl cellulose, carboxymethylcellulose, gums (e.g., alginates, acacia), gelatin, polyvinylpyrrolidone, and sucrose, (c) humectants, such as glycerol, (d) disintegrating agents, such as agar-agar, calcium carbonate, potato or tapioca starch, alginic acid, certain silicates sodium carbonate, starch including the commercial disintegrant based on starch, EXPLOTAB™, sodium starch glycolate, AMBERLITE™, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such as paraffin; (f) absorption accelerators, such as quaternary ammonium compounds and fatty acids including oleic acid, linoleic acid, and linolenic acid; (g) wetting agents, such as, for example, cetyl alcohol and glycerol monostearate, anionic detergent surfactants including sodium lauryl sulfate, dioctyl sodium sulfosuccinate, and dioctyl sodium sulfonate, cationic detergents including benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay; (i) lubricants, such as talc, calcium stearate, magnesium stearate, solid polyethylene glycols, sodium lauryl sulfate, polytetrafluoroethylene (PTFE), liquid paraffin, vegetable oils, waxes, CARBOWAX™ 4000, CARBOWAX™ 6000, magnesium lauryl sulfate, and mixtures thereof; and (j)

glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT®. Examples of embedding compositions which can be used include polymeric substances and waxes.

The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms can contain inert diluents commonly used in the art, such as, for example, water or other solvents, solubilizing agents and emulsifiers, such as ethyl alcohol, isopropyl alcohol, ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring flavoring, and perfuming agents. Oral compositions can be formulated and further contain an edible product, such as a beverage.

Suspensions, in addition to the active compounds, can contain suspending agents such as, for example ethoxylated isostearyl alcohols, polyoxyethylene sorbitol and sorbitan esters, microcrystalline cellulose, aluminum metahydroxide; bentonite, agar-agar, tragacanth, and mixtures thereof.

Pulmonary Administration

Also contemplated herein is pulmonary delivery of a DNA-PK inhibitor (or derivatives thereof). The inhibitor is delivered to the lungs of a mammal while inhaling, thereby promoting traversal of the lung epithelial lining to the blood stream. See, Adjei et al., *Pharmaceutical Research*, 7:565-569 (1990); Adjei et al., *International Journal of Pharmaceutics,* 63:135-144 (1990) (leuprolide acetate); Braquet et al., *Journal of Cardiovascular Pharmacology,* 13 (Suppl. 5): s. 143-146 (1989) (endothelin-1); Hubbard et al., *Annals of Internal Medicine,* 3:206-212 (1989) (α1-antitrypsin); Smith et al., *J. Clin. Invest.,* 84:1145-1146 (1989) (α1-proteinase); Oswein et al., "Aerosolization of Proteins," Proceedings of Symposium on Respiratory, Drug Delivery II, Keystone, Colo., March, 1990 (recombinant human growth hormone); Debs et al., *The Journal of Immunology,* 140:3482-3488 (1988) (interferon-γ and tumor necrosis factor α) and Platz et al., U.S. Pat. No. 5,284,656 (granulocyte colony stimulating factor).

A wide range of mechanical devices designed for pulmonary delivery of therapeutic products, including, but not limited to, nebulizers, metered dose inhalers, and powder inhalers, all of which are familiar to those'skilled in the art, are contemplated for use in the practice of this invention.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOLIN® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of a compound of the invention. Typically, each formulation is specific to the type of device employed and can involve the use of an appropriate propellant material, in addition to diluents, adjuvants, and/or carriers useful in therapy.

The inhibitor composition is prepared in particulate form, preferably with an average particle size of less than 10 μm, and most preferably 5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC, and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise a compound of the invention dissolved in water at a concentration of about 0.1 to 25 mg of biologically active protein per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the inhibitor compound suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be used as a surfactant.

Formulations for dispensing from a powder inhaler device comprise a finely divided dry powder containing the inhibitor and also can include a bulking agent, such as lactose, sorbitol, sucrose, mannitol, trehalose, or xylitol, in amounts which facilitate dispersal of the powder from the device, e.g., 50 to 90% by weight of the formulation.

Other Routes of Administration

Nasal delivery of the inhibitor also is contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration preferably are suppositories that can be prepared by mixing the compounds of the invention with suitable nonirritating excipients or carriers, such as cocoa butter, polyethylene glycol, or suppository wax, which are solid at room temperature, but liquid at body temperature, and therefore melt in the rectum or vaginal cavity and release the active compound.

In order to facilitate delivery of compounds across cell and/or nuclear membranes, compositions of relatively high hydrophobicity are preferred. Compounds can be modified in a manner which increases hydrophobicity, or the compounds can be encapsulated in hydrophobic carriers or solutions which result in increased hydrophobicity.

Dosages

Actual dosage levels of active ingredients in the pharmaceutical compositions of the invention can be varied to obtain an amount of the active ingredients that is effective to achieve the desired therapeutic response for a particular patient, composition, and mode of administration. The selected dosage level depends upon the activity of the particular compound, the route of administration, the severity of the condition being treated, and the condition and prior medical history of the patient being treated. However, it is within the skill of the art to start doses of the compound at levels lower than required to achieve the desired therapeutic effort and to gradually increase the dosage until the desired effect is achieved.

Generally dosage levels of about 0.1 to about 1000 mg, about 0.5 to about 500 mg, about 1 to about 250 mg, about 1.5 to about 100, and preferably of about 5 to about 20 mg of active compound per kilogram of body weight per day are administered orally or intravenously. If desired, the effective daily dose can be divided into multiple doses for purposes of administration, e.g., two to four separate doses per day.

The invention is exemplified by the following examples. Example 1 describes DNA-PK enzyme purification. Example 2 sets forth the standard DNA-PK enzyme assay. Example 3 addresses determination of selectivity of the DNA-PK inhibitors. Example 4 relates to assessing cellular toxicity of the DNA-PK inhibitors. Example 5 describes a DNA double-strand break repair assay. Example 6 addresses the ability of DNA-PK inhibitors to enhance radiation treatment. Example 7 addresses use of DNA-PK inhibitors in the treatment of human diseases. Examples 8-40 provide a synthesis and physical properties of nonlimiting examples of DNA-PK inhibitors of the present invention.

In the examples, the following abbreviations are used: $CO_2$ (carbon dioxide), U (units), mL (milliliter), µg (micrograms), L (liter), min (minutes), rpm (revolutions per minute), PBS (phosphate buffered saline), LSB (low salt buffer), mM (millimolar), HEPES (N-[2-hydroxyethyl]piperazine-N'-[2-ethenesulfonic acid]), KOH (potassium hydroxide), KCl (potassium chloride), NaCl (sodium chloride), $MgCl_2$ (magnesium chloride), EDTA (ethylenediaminetetraacetic acid), DTT (dithiothreitol), PMSF (phenylmethylsulfonyl fluoride), g (grams), h (hours), M (molar), ATP (adenosine triphosphate), µM (micromolar), mCi (millicurie), nM (nanomolar), DMSO (dimethyl sulfoxide), RT (room temperature), NP-40 (PEG (9)octylphenyl ether), PA (phosphoric acid), $MnCl_2$ (manganese chloride), BSA (bovine serum albumin), EGTA (ethylene glycol-bis(β-aminoethylether)N,N,N',N'-tetraacetic acid), Tris-HCl (tris(hydroxymethyl)aminomethane hydrochloride), MOPS (3-[N-morpholino]propane sulfonic acid), FBS (fetal bovine serum), $^3$H (tritium), D-PBS (phosphate buffered saline), Gy (gray), PK (protein kinase), Tris (tris(hydroxymethyl)aminomethane), rad (unit, measurement of radiation), $CH_2Cl_2$ (methylene chloride), $Na_2SO_4$ (sodium sulfate), EtOAc (ethyl acetate), $MgSO_4$ (magnesium sulfate), NaOH (sodium hydroxide), DMF (dimethylformamide), NaH (sodium hydride), LiOH (lithium hydroxide), MeOH (methanol), HCl (hydrochloric acid), THF (tetrahydrofuran), $NH_4Cl$ (ammonium chloride), TSOH (p-toluene sulfonic acid), $K_2CO_3$ (potassium carbonate), NMP (N-methylpyrrolidone), and $NaHCO_3$ (sodium carbonate).

EXAMPLE 1

DNA-PK Enzyme Purification

In order to develop an assay to screen for enzyme inhibitors, a method for large scale purification of human DNA-PK was performed (Lees-Miller et al., *Mol. Cell. Biol.*, 10:6472-6481 (1990)).

HeLa S3 cells (ATCC CCL-2.2; Batch F12594) were raised in MEM-Joklik media (Gibco) supplemented with 10% FBS, 100 U/mL penicillin and 100 µg/mL streptomycin at 37° C. in a humidified chamber under 5% $CO_2$. For enzyme purification, cells were grown to a density of approximately $1 \times 10^6$ cells/mL in two spinner flasks each containing 6 L media. Cells were collected by centrifugation for 10 min at 1,000 rpm in a GS-6R Beckman centrifuge. Cell pellets were washed one time in ice cold PBS and collected by centrifugation. Cells were resuspended in ice cold LSB buffer, containing 10 mM HEPES-KOH, pH 7.2, 25 mM KCl, 10 mM NaCl, 1 mM $MgCl_2$, 0.1 mM EDTA, and 0.1 mM DTT, and collected by centrifugation for 10 min at 2,000 rpm. Cell pellets were resuspended in an equal volume of buffer, allowed to stand on ice for 5 min, and then frozen in liquid nitrogen.

The frozen HeLa cell pellet was thawed at 37° C. and immediately centrifuged at 10,000×g in a Beckman JA10 rotor for 20 min at 4° C. The resulting supernatant (S10 faction, fraction I) was collected, solid PMSF was added to 0.5 mM final concentration, and the resulting mixture was centrifuged at 100,000×g in a Beckman Type 45Ti rotor for 3 h at 4° C. The pelleted material was resuspended in H buffer (containing 25 mM HEPES-KOH, pH 7.5, 0.2 mM EDTA, 0.5 mM DTT, 0.5 M KCl, and 10 mM $MgCl_2$) and centrifuged at 100,000×g for 1 h at 4° C. H Buffer was added to the supernatant until the ionic strength was equal to that of H buffer containing 0.1 M KCl (S100-2 fraction, also fraction II).

The S100-2 fraction was applied to a 28 mL Q-SEPHAROSE® FF column (1.5×16 cm) equilibrated in H buffer with 0.1 M KCl. The resin was washed with 5 column volumes and developed with a 140 mL linear gradient (0.1 to 0.5 M KCl in H buffer) at a flow rate of 1.5 mL/min. A broad peak of activity was eluted, pooled, and dialyzed into H buffer with 0.1 M KCl (fraction III).

Fraction III was applied to an 8 mL SP-SEPHAROSE® FF column (1×10 cm) equilibrated in H buffer with 0.1 M KCl. The resin was washed with 5 column volumes and developed with a 30 mL linear gradient (0.1 to 0.5 M KCl in H buffer) at a flow rate of 1.5 mL/min. Active fractions were pooled (fraction IV) and stored at −70° C.

EXAMPLE 2

Standard DNA-PK Assay

Standard kinase reactions used to measure phosphorylation of a p53 peptide substrate (SEQ ID NO: 1) contained, in 20 µL, 25 mM HEPES-KOH, pH 7.5, 10 mM $MgCl_2$, 0.5 mM DTT, 50 µM ATP, 0.01 mCi/mL [γ-$^{32}$P]ATP; 10 µg/mL replicative form III (RFIII) DNA, 200 µM p53 peptide and 0.2 µg purified DNA-PK (as described in Example 1).
Glu-Pro-Pro-Leu-Ser-Gln-Glu-Ala-Phe-Ala-Asp-Leu-Trp-Lys-Lys-Arg SEQ ID NO: 1

Reactions were carried out at room temperature. Reactions were started by addition of ATP and stopped by application to phosphocellulose paper. Reaction products spotted onto phosphocellulose paper were washed five times with a total volume of at least 250 mL 10% acetic acid or 150 mM phosphoric acid. The paper was air dried and radioactivity was determined in a Beckman LS6000IC scintillation counter.

The DNA-PK activity was found to be stimulated 17-fold in the presence of linear duplex RFIII DNA and activity was dependent upon addition of polypeptide substrate. The $K_m$ and $V_{max}$ for ATP consumption were found to be 6.6 µM ATP and 1.2 pmol ATP/min, respectively. Enzyme activity was inhibited by wortmannin with an $IC_{50}$=100 to 250 nM and by demethoxyviridin at an $IC_{50}$=5 nM.

One example of an active compound is 10-benzyl-1-hydroxy-3-morpholin-4-yl-10H-acridin-9-one, having an $IC_{50}$ of 20 nM. Compounds of the present invention were tested, and have an $IC_{50}$ of less than 1 µM to about 100 µM, and typically about 1 to about 100 µM.

EXAMPLE 3

Selectivity Determination

Some of the most potent inhibitors of DNA-PK were tested for the ability to inhibit phosphorylation catalyzed by other kinase enzymes. In order to distinguish the DNA-PK specific inhibitors from general protein kinase inhibitors, the inhibitors identified Example 2 were used in assays with distantly related (from a phylogenic standpoint) protein kinases (Hunter et al., *Trends. Biochem. Sci.*, 22:18-22 (1997)) casein kinase I, protein kinase Cθ and the calcium/calmodulin dependent kinase II. To identify which inhibitors preferentially bound to DNA-PK from a set of more closely related kinases, the compounds were assayed for inhibitory activity against the ataxia-telangiectasia related (ATR) protein kinase, the FK506-rapamycin associated protein kinase, and the phosphatidylinositol-3 kinase p110δ. Compounds that selectively inhibited phosphorylation catalyzed by DNA-PK were defined as specific inhibitors of DNA-PK. Selectivity of inhibition can be defined as follows:

($IC_{50}$(test enzyme))/($IC_{50}$(DNA-PK))>10

All assays were carried out at room temperature in polypropylene microfuge tubes or polystyrene microtiter plates.

PI3Kβ Assay

Kinase assays contained, in 60 µL, DNA-PK inhibitor in 2% DMSO, 20 µM ATP, 40 µM HEPES-KOH, pH 7.4, 1 µM phosphatidylinositol (4, 5) $P_2$, 0.0088 mCi/mL [γ-$^{32}$P]ATP, 8 mM $MgCL_2$, 1 mM DTT, 0.05 mg/mL horse IgG, and 1 nM PI3K β purified enzyme. Reactions were started by addition of enzyme and stopped after 10 min RT incubation with 160 µL 1M potassium phosphate, pH 8.0, 30 mM EDTA. Terminated reaction mixtures were transferred to PVDP plates (prewet with methanol), washed three times with 1M potassium phosphate, air dried, and radioactivity measured using a liquid scintillation counter (Wallace 1450 microbeta plus).

Chk1 Assay

Kinase assays contained, in 60 µL, DNA-PK inhibitor in 1.2% DMSO, 4 µM ATP, 20 mM HEPES-KOH, pH 7.4, 20 µM Cdc25C peptide SEQ ID NO:2, (N-leu-tyr-arg-ser-pro-ser-met-pro-glu-asn-leu-asn-arg-arg-arg-arg-OH), 0.002 mCi/mL [γ-$^{32}$p]ATP, 5⁻ mM $MgCl_2$, 0.1% NP-40, 1 mM DTT, and 210 ng Chk1 purified enzyme. Reactions were started by addition of radionucleotide and stopped after 10 min RT incubation with 20 µL 600 mM PA. Terminated reaction mixtures were transferred to P81 plates (prewet with 150 mM PA), washed five times 150 mM PA, and radioactivity measured using a liquid scintillation counter (Wallace 1450 microbeta plus).

FK506-Rapamycin Associated Protein Kinase (FRAP) Assay

Kinase assays contained, in 60 µL, DNA-PK inhibitor in 3% DMSO, 10 mM HEPES-KOH, pH 7.4, 10 mM $MnCl_2$, 50 mM NaCl, 0.3 mg/mL BSA, 10 µM ATP, 0.08 mCi/mL [γ-$^{32}$P]ATP, 0.2 mg/mL pH-acid stable protein (PHAS) substrate, purified recombinant FRAP kinase (Brown et al., *Nature*, 369:756-758, 1994). Reactions were started by addition of ATP and stopped after 45 min RT incubation with 20 µL 0.9 M PA. Terminated reaction mixtures were transferred to P81 plates (prewet with 150 mM PA), washed five times with 15 mM PA, and radioactivity measured using a liquid scintillation counter (Wallace 1450 microbeta plus).

Src Kinase Assay

Src kinase and substrate peptide were purchased from Upstate Biotech. Reaction cocktails contained: 100 mM Tris-HCl, pH 7.5, 125 mM $MgCl_2$, 25 mM $MnCl_2$, 2 mM EGTA, 2 mM DTT, 100 µM peptide substrate, 10 µM ATP, 2.5 µCi γ32P-ATP per reaction, 6 units of Src kinase per reaction. DNA-PK inhibitor compounds were added to the reactions in pure DMSO at a 1:10 dilution (10% DMSO final). Commercially available inhibitors PP1 or PP2 were used as controls. Reactions (60 µL) were incubated 30 min at RT and stopped by adding 150 µL of 150 mM PA. Reaction mixtures (200 of 210 µL) then were pipetted onto millipore 96-well p81 plates, and the wells washed 3×200 µL with 150 mM Eco-Scint (60 µL) was added to the washed, dried wells, and the plate was counted on a Wallace counter.

cdc2 Kinase Assay cdc2 Kinase and histone H1 substrate were purchased from Upstate Biotech. Reaction cocktails contained: 50 mM Tris-HCl, pH 7.55, 10 mM $MgCl_2$, 1 mM EGTA, 2 mM DTT, 0.01% BRIJ® 35, 5 µg histone H1, 10 µM ATP, 3.5 µCi γ32P-ATP per reaction, 1 µL of Src kinase per reaction. DNA-PK inhibitor compounds were added to the reactions in pare DMSO at a 1:10 dilution (10% DMSO final). Reactions (60 µL) were incubated 10 min at RT and stopped by adding 150 µL of 150 mM PA. Reaction mixtures (200 of 210 µL) then were pipetted onto millipore 96-well p81 plates and the wells washed 3×200 µL with 150 mM PA. Eco-Scint (60 µL) was added to the washed, dried wells, and the plate was counted on a Wallace counter.

PKA Kinase Assay

PKA kinase and substrate were purchased from Upstate Biotech. Reaction cocktails (50 µL) contained 20 mM, MOPS, pH 7.2, 25 mM β-glycerol phosphate, 5 mM EGTA, 1 mM sodium orthovanadate, 1 mM DTT, 11.25 mM $MgCl_2$, 10 µM ATP, PKA 0.06 µL enzyme, 10 µL substrate cocktail, 4 µCi [γ32P]ATP, and 10 µL inhibitor cocktail were used in each 50 µL assay. Compounds were added to the reactions in pure DMSO at a 1:10 dilution (10% DMSO final). Reactions were incubated 10 min at RT and quenched by adding 150 µL of 150 mM PA. Reaction mixtures (200 of 210 µL) then were pipetted onto millipore 96-well p81 plates and the wells washed 3×200 µL with 150 mM PA. Eco-Scint (60 µL) was added to the washed, dried wells, and the plate was counted on a Wallace counter.

EXAMPLE 4

Cellular Toxicity Determination

Short-term (10 hours) and long-term (5 days) cellular toxicity of various DNA-PK inhibitors were measured. The human colorectal carcinoma cell line, HCT-116, was incubated with inhibitor compounds at concentrations up to 50 µM. Cells were maintained in RPMI 1640 (Gibco) containing 10% FBS, 1 mM sodium pyruvate, 2 mM L-glutamine, 100 U/mL penicillin, and 100 µg/mL streptomycin at 37° C. with 5% $CO_2$ in a humidified incubator. Cultured cells were trypsinized, counted, and seeded into 96-well plates at a concentration of 1000 cells/well. Cells were incubated with varying concentrations of the inhibitor compounds from 1.8 µM to 50 µM for 10 hr or 5 days, and the media-containing compounds were removed and replaced with fresh media without drug. After five days, $^3$H thymidine (1 µCi/well) was added to each well and incubated for an additional 20 hr. The plates were frozen at −70° C. for at least 2 hr, then thawed at 37° C. to lyse the cells. DNA was harvested onto glass fiber filters and counted for $^3$H thymidine incorporation on a Packard Matrix 96 direct beta counter.

EXAMPLE 5

DNA Double-strand Break Repair Assay

To further determine the cellular effect of DNA-PK inhibitors, an assay to measure chromosomal discontinuities was employed. Ionizing radiation induces chromosomal DNA double-strand breaks. Following high dose radiation, chromosomes can be extracted from cells and fractionated by pulse field electrophoresis to distinguish chromosomal fragments from intact larger chromosomes. Using this technique, the activity of DNA-PK inhibitors was measured.

MDA-MB231 (human breast carcinoma) cells were seeded onto T25 flasks with RPMI1640+10% FBS, 2 mM L-glutamine, penicillin G 100 U/ml-streptomycin sulfate 10 µg/ml, 1 mM Na pyruvate. When confluent, media was removed and replaced with media containing DNA-PK inhibitor or vehicle. Cells were incubated at 37° C. for 1 hr in a humidified chamber with 5% $CO_2$. Media then was removed and flasks were filled with ice-cold D-PBS and either: (a) processed immediately; (b) irradiated (25 Gy in a $^{137}$Cs Mark I irradiator at a flux of 335 rad/min) and processed immediately; (c) irradiated and incubated for 2 hr in complete RPMI1640+vehicle at 37° C. (in humidified 5% $CO_2$ atmosphere to allow for DNA repair), or (d) irradiated and incubated for 2 hr in complete RPMI1640+DNA-PK inhibitor compound. To process cells, D-PBS or media was replaced with 5 ml ice-cold D-PBS and cells were removed from flasks, concentrated with cell resuspension buffer (10 mM Tris pH 7.2, 50 m EDTA) and added to warm 2% clean cut agarose (Bio-Rad #170-3594). Cell slurries were embedded in agarose, then incubated in PK buffer (10 mM Tris pH 8.0, 100 mM EDTA, 1% lauryl sarcosine, 0.2% sodium deoxycolate, 100 µg/ml Proteinase K (Bio-Rad #732-6348)) at 4° C. for 2 min, followed by incubation at 50° C. overnight. Cells embedded in agarose plugs were washed with buffer containing 10 mM Tris pH 8.0, 50 mM EDTA three times for 15 min. An agarose gel (1% low melt agarose; Bio-Rad #162-0017) then was cast around plugs in 0.5×TBE and chromosomal DNA was fractionated by pulse field gel electrophoresis at 99V (2V/cm), 45 sec pulse time, 48 hr with 14° C. recirculating 0.5×TBE in a CHEF-DR II cell apparatus (Bio-Rad). Chromosomal DNA was visualized with SYBR-Gold (Molecular probes #S-11494) and the fluorescent image quantified on the STORM 860 (Molecular Dynamics).

Using this technique, it was found that concentrations of 10-benzyl-1-hydroxy-3-morpholin-4-yl-10H-acridine-9-one which enhanced radiation induced cell killing (measured by the DNA synthesis assay) also inhibited DNA double-strand break repair. These data demonstrate that DNA-PK inhibitors perturb chromosomal DNA double-strand break repair, and suggests that inhibition of this DNA repair reaction is responsible for the potentiation of radiation toxicity. Furthermore, these data suggest that DNA-PK inhibitors bind the target in the nucleus ultimately inducing sensitivity to chemical and physical agents that yield DNA dsbs.

EXAMPLE 6

Radiation Enhancement

Cellular Proliferation Assay

To measure the ability of present DNA-PK inhibitor compounds to enhance the toxic effect of radiation treatment, the human colorectal carcinoma cell line, HCT-116, was incubated with inhibitor compounds at concentrations up to 50 µM and treated with γ-radiation at doses up to 800 rads. Cells were maintained in RPMI 1640 (Gibco) containing 10% PBS, 1 mM sodium pyruvate, 2 mM L-glutamine, 100 U/mL penicillin, and 100 µg/mL streptomycin at 37° C. with 5% $CO_2$ in a humidified incubator. Cultured cells were trypsinized, counted, and seeded into 96 well plates at a concentration of 1000 cells/well. Cells were incubated with varying concentrations of the inhibitor compounds from 1.8 µM to 50 µM for 10 hr or 5 days, then the media-containing compounds were removed and replaced With fresh media without drug. After five days, $^3$H thymidine (1 µCi/well) was added to each well and incubated for an additional 20 hr. The plates were frozen at −70° C. for at least 2 hr and thawed at 37° C. to lyse the cells. DNA was harvested onto glass fiber filters and $^3$H thymidine incorporation determined with a Packard Matrix 96 direct beta counter. Compound dependent potentiation of radiation induced cell killing was determined by comparing the effect of radiation alone and radiation plus inhibitor compound.

For example, 10-benzyl-1-hydroxy-3-morpholin-4-yl-10H-acridin-9-one was tested and enhanced radiation induced cell killing 2-fold at 17.5 µM. Several of the present DNA-PK inhibitors enhanced radiation induced cell killing 2-fold at less than 100 µM.

EXAMPLE 7

Use of DNA-PK-Inhibitors in the Treatment of Human Disease

The observations described herein indicate that the DNA-PK inhibitors have broad applications in the treatment of proliferative disorders, including cancer. In particular, the inhibitors potentiate the therapeutic effects of radiation during the treatment of human cancers and can be used in combination with chemotherapy and several forms of radiation treatments including, teletherapy (i.e., radiation therapy administered from a source at a distance from the body), radioimmunotherapy, and brachytherapy (i.e., radiation therapy wherein the irradiation source is close to or within the body). The radiation can be administered by stereotactic radiosurgery or fractionated microbeam teletherapy.

During teletherapy, drug administration prior to radiation treatment, as performed in the animal experiments described above, is most effective in reducing tumor mass. In this method, the drug is administered systemically and radiation is focused locally to the tumor site. Circumstances also can exist wherein it is advantageous to administer the DNA-PK inhibitor following radiation treatment. In either treatment, the drug can be delivered by any of a number of routes described herein. Potentiation of the efficacy of teletherapy can be applied to radiocurative tumors as well as radiorefractory tumors. Seminoma, a carcinoma of the cervix, larynx, breast and prostate, Hodgkin's disease, and acute lymphocytic leukemia are examples of radiocurative tumors for which this class of DNA-PK inhibitors improve treatment by achieving greater therapeutic effect and reducing collateral tissue toxicity. Combination therapy using the drug with teletherapy also has the effect of enhancing, the radioresponsiveness of radioresistant tumors; some examples include as glioblastomas, osteogenic sarcomas, retinoblastomas, astrocytomas, and some head and neck cancers. It is anticipated that inhibition of DNA-PK activity can be of therapeutic benefit in all instances where radiation is used with curative intent.

Radiation therapy also is indicated for pain management during cancer treatment. Palliation of pain is an important component of some treatment strategies. It is contemplated that the procedure of radiation with palliative intent also is enhanced by inhibition of DNA-PK in tumor and possible normal tissue, e.g., administration of bone-localizing isotopes, such as Sn-117, for the treatment of bone pain associated with bone cancer.

The DNA-PK inhibitors of the invention also are effective in combination with radioimmunotherapy and brachytherapy. The goal in these therapies is to deliver radiation internally to tumor sites in an attempt to minimize damage to surrounding normal tissue, radioactive seed implants for prostate cancer. The DNA-PK inhibitors can be used to enhance the therapeutic index of these radiation, treatments also.

DNA-PK inhibitors of the invention also can be used to potentate the benefits of chemotherapy. Combination treatment with chemotherapeutic agents that induce DNA damage and a DNA-PK inhibitor induces a synergistic effect on tumor tissue as observed in experiments using etoposide, bleomycin, and chlorambucil with cultured human tumor cells. These data indicate that treatment regimens employing topoisomerase inhibitors, alkylating agents, and/or bleomycin are enhanced by this class of DNA-PK inhibitor. Other chemical agents used in the treatment of cancer also can be made more effective by inhibition of DNA-PK.

Therapeutic benefit also can be obtained through the administration of a DNA-PK inhibitor conjugated to an antibody. Drug delivery can be targeted to specific sites within the body as a function of the determinants of antibody recognition. This method of administration can be combined with radiation or chemotherapy. It is envisioned that DNA-PK inhibitor drugs can be coadministered with chemotherapeutic drugs which themselves are linked to tumor-specific antibodies.

It also is envisioned that DNA-PK inhibitors can be used in combination with nongenotoxic modulators of the cell division cycle with or without genotoxic treatments, such as radiation and chemotherapy described above. Such nongenotoxic treatments are anticipated to perturb cell cycle metabolism, affecting the temporal order and kinetics of cell cycle events such as initiation or the cell cycle, DNA replication, centrosome duplication, chromosome segregation, and cytokinesis. The execution of these cell cycle events is integrated with events related to DNA damage repair. Therefore, the combined effect of disrupting the coordinated repair of DNA damage with cell cycle progression is expected to reduce the fidelity of the cell division cycle with lethal consequences.

Because many anticancer drugs are also immunosuppressive, the DNA-PK inhibitors also can be used to potentiate the efficacy of drugs in the treatment of inflammatory diseases. Examples of some diseases that can benefit from combination therapy with the inhibitors are rheumatoid arthritis, psoriasis, vitiligo, Wegener's granulomatosis, and systemic lupus erythematosus (SLE). A common theme in the treatment of arthritis, Wegener's granulomatosis, and SLE is the use of immunosuppressive therapies such as ionizing radiation, methotrexate, and cyclophosphamide. As these treatments induce DNA damage, either directly or indirectly, inhibition of DNA-PK activity within offending immune cells will render the cells more sensitive to control by these standard treatments. Psoriasis and vitiligo are commonly treated with ultraviolet radiation (UV) in combination with psoralens. These two DNA damaging agents induce T cell killing thought to be responsible for this disease. Inhibition of DNA-PK enhances the killing effect of UV radiation and psoralens, and increases the therapeutic index of the treatment regimen. In general, the DNA-PK inhibitors can potentiate the control of inflammatory disease cells in combination with currently used immunosuppressive drugs.

Recently, it has been demonstrated that cells cultured from scid mice are refractory to retrovirus infection (Daniel et al., *Science*, 284: 644-647 (19,99)) due to the deficiency in DNA-PK. This class of DNA-PK inhibitors therefore can be used to protect cells from retroviral infection. These inhibitors can have therapeutic benefit in the treatment of acquired immune deficiency syndrome (AIDS) by blocking HIV infection of T-cells. In this example, this class of inhibitors can have significant activity as a single agent or coadministered with other antiviral agents, such as protease inhibitors, transcriptase inhibitors, nucleoside analogs, and the like.

To the degree that DNA-PK participates in retroviral infection, inhibitors of the invention can be used in therapeutic intervention. The RNA genome of retroviruses is copied into DNA which integrates into the genome of an infected cell. Integration necessarily requires introduction of dsbs in the host cell genome, and observations suggest a role for DNA-PK is repairing the break (Daniel et al., *Science*, 284:644-647 (1999)). Inhibition of DNA-PK therefore arrests cell growth and signal apoptosis of the infected cell.

Preliminary results using retrovirus-infected Jurkat J77 cells indicated that apoptosis increased 1.5- to 2-fold in cells treated with a DNA-PK inhibitor compared to cells that were not treated.

The inhibitors of the invention also can be effective during marrow ablation prior to bone marrow transplantation. Bone marrow conditioning is go currently performed by treatment with cytotoxic agents such as ionizing radiation, cyclophosphamide, and/or busulfan. The goal of the procedure is to remove existing marrow cells and provide space for transplanted stem cells to take residence. The inhibitors therefore can potentiate the cytotoxic effect of current treatments by allowing more effective bone marrow conditioning with less toxic side effects.

EXAMPLES 8-51

Examples of DNA-PK Inhibitors and Synthetic Methods Therefor

The synthesis of nonlimiting examples of the present DNA-PK inhibitors is set forth below.

EXAMPLE 8

Trifluoromethanesulfonic acid 1-hydroxy-9-oxo-9H-xanthen-3-yl ester

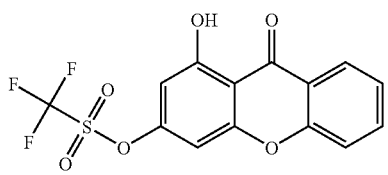

Trifluoromethanesulfonic anhydride (0.54 mL, 3.21 mmol) was added slowly to a solution of, 1,3-dihydroxyxanthen-9-one (689 mg, 3.02 mmol) and pyridine (7.3 mL) in $CH_2Cl_2$ (30 mL) at 0° C. The reaction then was allowed to slowly warm to RT and stirred for 16 h. The orange mixture then was dissolved in $CH_2Cl_2$ (100 mL), and washed with 10% citric acid (2×25 mL) and brine (1×25 mL). The organics were dried ($Na_2SO_4$), concentrated, and purified by Biotage chromatography using 10% EtOAc/hexanes as eluent to yield 702 mg (65%) of trifluoromethanesulfonic acid 1-hydroxy-9-oxo-9H-xanthen-3-yl ester as a light yellow solid. $R_f$=0.65 (50% EtOAc/hexanes). See R. Pillai et al., *J. Org. Chem.*, 51, pages 717-723 (1986). $^1$H NMR (DMSO-$d_6$, 400 MHz) δ: 12.90 (s, 1H), 8.20 (d, 1H), 7.96 (dd, 1H), 7.70 (d, 1H), 7.56 (dd, 1H), 7.37 (m, 1H), 7.05 (m, 1H).

EXAMPLE 9

1-Hydroxy-3-morpholin-4-yl-xanthen-9-one

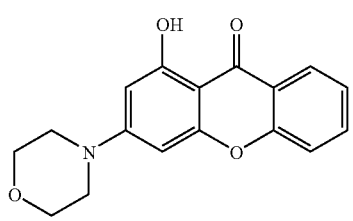 [SMILES: O=c1c2ccccc2oc2cc(N3CCOCC3)cc(O)c12]

A suspension of Example 8 (605 mg, 167.9 mmol), potassium phosphate (505 mg, 2.379 mmol), tris(dibenzylideneacetone)dipalladium(0) (157 mg, 0.171 mmol), biphenyl-2-yl-di-tert-butyl-phosphane (105, mg, 0.352 mmol), and morpholine (0.176 mL, 2.012 mmol) in toluene (4 mL) was heated at 80° C. for 4 hours, then stirred 16 hours at room temperature. The reaction was dissolved in EtOAc (250 mL), and washed with saturated ammonium chloride ($NH_4Cl$) (2×50 mL) and brine (1×50 mL). The organics were dried ($MgSO_4$), concentrated, and purified via Biotage chromatography using 10% EtOAc/hexanes as eluent to yield 148 mg (30%) of 1-hydroxy-3-morpholin-4-yl-xanthen-9-one. $R_f$=0.45 (50% EtOAc/hexanes). $^1$H NMR (DMSO-$d_6$, 400 MHz) δ: 12.75 (s, 1H), 8.11 (d, 1H), 7.83 (dd, 1H), 7.54 (d, 1H), 7.45 (dd, 1H), 6.54 (s, 1H), 6.36 (s, 1H), 3.72 (m, 4H), 3.43 (m, 4H). LRMS (APCI, positive): 298.3 (m+1).

EXAMPLE 10

1-Hydroxy-6-methoxy-3-trifluoromethanesulfonyl-xanthen-9-one ester

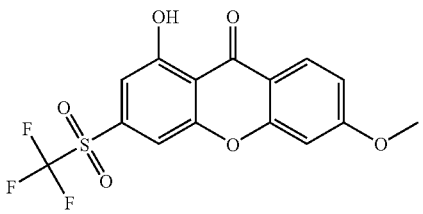 [SMILES: COc1ccc2c(=O)c3c(O)cc(S(=O)(=O)C(F)(F)F)cc3oc2c1]

Trifluoromethanesulfonic anhydride (0.326 mL, 1.94 mmol) was added slowly to a solution of 1,3-dihydroxy-6-methoxy-xanthen-9-one (501 mg, 1.94 mmol) and triethylamine (0.54 mL) in $CH_2Cl_2$ (30 mL) at 0° C. The reaction then was allowed to slowly warm to room temperature and stirred for 16 h. The orange colored reaction then was purified by Biotage chromatography using 10% EtOAc/hexanes as eluent to yield 60 mg (8%) of 1-hydroxy-6-methoxy-3-trifluoro-methanesulfonyl-xanthen-9-one ester as a white solid. $R_f$=0.70 (50% EtOAc/hexanes). $^1$H NMR (DMSO-$d_6$, 400 MHz) δ: 13.14 (s, 1H), 8.13 (d, 1H), 7.70 (m, 1H), 7.30 (s, 1H), 7.20 (m, 1H), 7.03 (s, 1H), 3.97 (s, 3H).

EXAMPLE 11

1-Hydroxy-6-methoxy-3-morpholin-4-yl-xanthen-9-one

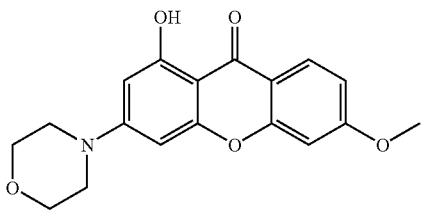 [SMILES: COc1ccc2c(=O)c3c(O)cc(N4CCOCC4)cc3oc2c1]

A suspension of Example 10 (60 mg, 0.154 mmol), potassium phosphate (56 mg, 0.264 mmol), tris(dibenzylideneacetone)dipalladium(0) (16 mg, 0.017 mmol), biphenyl-2-yl-di-tert-butyl-phosphane (11 mg, 0.037 mmol), and morpholine (0.016 mL, 0.183 mmol) in toluene (3 mL) was heated to 75° C. for 16 h. The reaction mixture was dissolved in EtOAc (150 mL), then washed with water (4×20 mL) and brine (1×10 mL The organics were dried ($MgSO_4$), concentrated, and purified via Biotage chromatography using 10% EtOAc/hexanes as eluent. The desired fractions were concentrated and recrystallized from EtOAc/hexanes to yield 1.2 mg (2%) of 1-hydroxy-6-methoxy-3-morpholin-4-yl-xanthen-9-one. $R_f$=0.40 (50% EtOAc/hexanes). $^1$H NMR (CDCl3, 400 MHz) δ: 12.87 (s, 1H), 8.13 (d, 1H), 6.91 (d, 1H), 6.80 (s, 1H), 6.28 (s, 1H), 6.24 (s, 1H), 3.93 (s, 3H), 3.85 (m, 4H), 3.36 (m, 4H). LRMS (Electrospray, positive): 328.4 (m+1).

EXAMPLE 12

1,6-Dihydroxy-3-morpholin-4-yl-xanthen-9-one

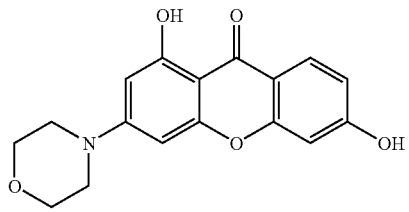 [SMILES: O=c1c2ccc(O)cc2oc2cc(N3CCOCC3)cc(O)c12]

To a 2.0 mL solution of 1:1 acetic acid and hydrobromic acid (48%) was added the compound of Example 11 (91 mg, 0.278 mmol). The resulting mixture was refluxed for 18 h. The reaction was allowed to cool to RT, then adjusted to pH 6 with 50% NaOH (1.1 mL). The aqueous layer was extracted with EtOAc (6×50 mL), and the organic layers were combined and washed with water (1×10 mL) and brine (1×25 mL). After drying (MgSO$_4$), the mixture was concentrated to a light brown solid to afford 170 mg of crude material, which then was purified via Biotage chromatography using 20% EtOAc/hexanes as eluent to yield 50 mg (58%) of 1,6-dihydroxy-3-morpholin-4-yl-xanthen-9-one. R$_f$=0.30 (50% EtOAc/hexanes): $^1$H NMR (DMSO-d$_6$, 400 MHz) δ: 12.91 (s, 1H), 7.95 (d, 1H), 6.86 (d, 1H), 6.80 (s, 1H), 6.49 (s, 1H), 6.30 (s, 1H), 3.80 (m, 4H), 3.36 (m, 4H). LRMS (APCI, negative): Da/e 312.4 (m−1).

EXAMPLE 13

8-Hydroxy-6-morpholin-4-yl-9-oxo-9H-xanthen-3-yloxy)acetic acid methyl ester

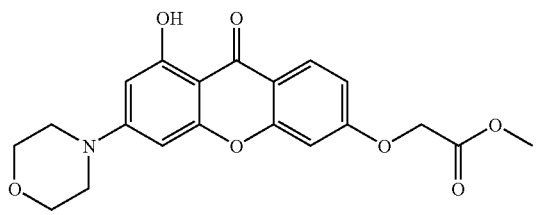 [SMILES: COC(=O)COc1ccc2c(=O)c3c(O)cc(N4CCOCC4)cc3oc2c1]

To a solution of the compound of Example 12 (54.3 mg, 0.156 mmol) in DMF (1.0 mL) was added NaH (10.0 mg, 0.203 mmol). After a majority of the hydrogen gas evolved, the solution was heated at 50° C. for 1 h. Then methyl bromoacetate (0.018 mL, 0.172 mmol) was; added dropwise, and heating was continued for 2 h. The reaction was cooled to RT, dissolved in EtOAc (100 mL), and washed with water (5×20 mL) and brine (1×20 mL). After drying (MgSO$_4$), the solution was concentrated to a yellow solid. The solid then was purified via Biotage chromatography using a gradient of 10%-40% EtOAc/hexanes as eluent to yield 21 mg (35%) of (8-hydroxy-6-morpholin-4-yl-9-oxo-9H-xanthen-3-yl-oxy) acetic acid methyl ester. $^1$H NMR (CDCl$_3$, 400 MHz) δ: 12.80 (s, 1H), 8.15 (d, 1H), 6.92 (d, 1H), 6.78 (s, 1H), 6.26 (s, 1H), 6.22. (s, 1H), 4.78 (s, 2H), 3.84 (s, 3H), 3.83 (m, 4H), 3.38 (m, 4H). LRMS (APCI, positive): Da/e 386.2 (m+1).

EXAMPLE 14

(8-Hydroxy-6-morpholin-4-yl-9-oxo-9H-xanthen-3-yloxy)acetic acid

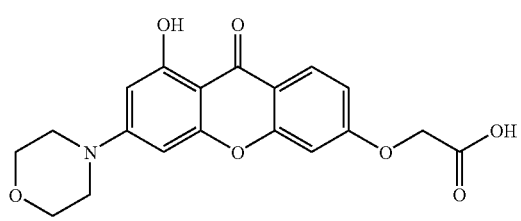 [SMILES: O=C(O)COc1ccc2c(=O)c3c(O)cc(N4CCOCC4)cc3oc2c1]

A solution of the compound of Example 13 (18.0 mg, 0.047 mmol) and LiOH (10.0 mg, 0.238 mmol) in a 2:1:1 mixture of THF/MeOH/water (1.0 mL) was heated for 1 h at 45° C. The reaction was cooled to RT and extracted with EtOAc (50 mL). The aqueous layer was acidified with 2M HCl (4 drops), then extracted with EtOAc (3×50 mL). The organics then were dried (MgSO$_4$) and concentrated to provide 8.0 mg (46%) of (8-hydroxy-6-morpholin-4-yl-9-oxo-9H-xanthen-3-yloxy) acetic acid as a white solid. $^1$H NMR (DMSO-d$_6$, 400 MHz) δ: 12.80 (s, 1H), 88.01 (d, 1H), 7.03 (m, 1H), 6.98 (s, 1H), 6.50 (s, 1H), 6.32 (s, 1H), 4.90 (s, 2H), 3.70 (m, 4H), 3.38 (m, 4H). LRMS (APCI, positive): Da/e 372.3 (m+1).

EXAMPLE 15

Trifluoromethanesulfonic acid, 1-hydroxy-5-methoxy-9-oxo-9H-xanthen-3-yl ester

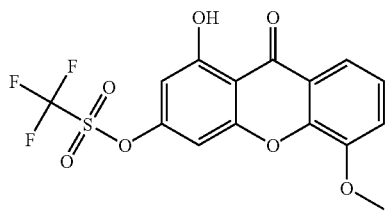 [SMILES: COc1cccc2c(=O)c3c(O)cc(OS(=O)(=O)C(F)(F)F)cc3oc12]

Trifluoromethanesulfonic anhydride (3.1 mL, 18.43 mmol) was slowly added to a solution of 1,3-dihydroxy-5-methoxy-xanthen-9-one (3.32 g, 12.85 mmol) and pyridine (32.0 mL) in CH$_2$Cl$_2$ (130 mL) at 0° C. See, D. K. Ho et al., J. Org. Chem., 52, pp. 342-347 (1987). The reaction mixture then was allowed to slowly warm to RT and stirred for 16 h. The resulting orange mixture was concentrated to a brown oil, then dissolved in EtOAc (750 mL) and washed with 5% citric acid (3×100 mL), water (1×100 mL), and brine (1×100 mL). The organics were dried (MgSO$_4$) and concentrated to yield 3.0 g (60%) of trifluoromethanesulfonic acid, 1-hydroxy-5-methoxy-9-oxo-9H-xanthen-3-yl ester as a light brown solid. R$_f$=0.65 (50% EtOAc/hexanes). $^1$H NMR (DMSO-d$_6$, 400 MHz) δ: 12.89 (s, 1H), 7.74 (d, 1H), 7.60 (m, 1H), 7.50 (m, 1H), 7.42 (s, 1H), 7.04 (s, 1H), 3.97 (s, 3H).

EXAMPLE 16

1-Hydroxy-5-methoxy-3-morpholin-4-yl-xanthen-9-one

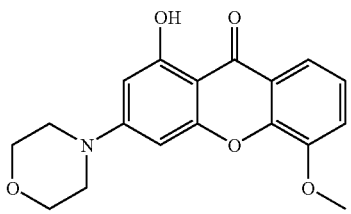 [SMILES: COc1cccc2c(=O)c3c(O)cc(N4CCOCC4)cc3oc12]

A suspension of the compound of Example 15 (2.79 g, 7.14 mmol), potassium phosphate (3.042 g, 14.33 mmol), tris(dibenzylideneacetone)dipalladium (0) (329 mg, 0.359 mmol), biphenyl-2-yl-di-tertbutyl-phosphine (428 mg, 1.43 mmol), and morpholine (0.8 mL, 9.15 mmol) in THF (20 mL) was heated to 75° C. for 16 h. The reaction mixture was concentrated, then dissolved in EtOAc (300 mL) and washed with water (1×100 mL)), saturated NH$_4$Cl (3×50 mL), and brine (1×10 mL). The organics were dried (MgSO$_4$) and concentrated. The crude solids were triturated in hot EtOAc (50 mL), cooled to RT, then filtered. The solid, were washed with EtOAc (10 mL), then dried to yield 1.31 g (56%) of 1-hydroxy-5-methoxy-3-morpholin-4-yl-xanthen-9-one. R$_f$=0.35 (50% EtOAc/hexanes). $^1$H NMR (DMSO-d$_6$, 400 MHz) δ: 12.74 (s, 1H), 7.64 (d, 1H), 7.48 (d, 1H), 7.34 (m, 1H), 6.55 (s, 1H), 6.35 (s, 1H), 3.93 (s, 3H), 3.80 (m, 4H), 3.42 (m, 4H). LRMS (APCI, positive): 328.3 (m+1).

EXAMPLE 17

1,5-Dihydroxy-3-morpholin-4-yl-xanthen-9-one

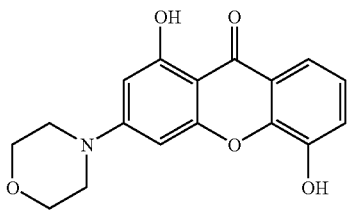 [SMILES: O=c1c2cccc(O)c2oc2cc(N3CCOCC3)cc(O)c12]

To a 32.0 mL solution of 1:1 acetic acid and hydrobromic acid (48%) was added the compound of Example 16 (1.11 g, 3.39 mmol), then the resulting mixture was refluxed for 6 h. The reaction was allowed to cool to 22° C. and then adjusted to pH 6 with 50% NaOH (23.0 mL). The aqueous layer was extracted with EtOAc (3×100 mL), and the organics were combined and washed with water (1×50 mL) and brine (1×50 mL). After drying (MgSO$_4$), the mixture was concentrated to a light brown solid, which then was purified via trituration in CH$_2$Cl$_2$ to yield 670 mg (63%) of 1,5-dihydroxy-3-morpholin-4-yl-xanthen-9-one. R$_f$=0.30 (50% EtOAc/hexanes). $^1$H NMR (DMSO-d$_6$, 400 MHz) δ: 12.81 (s, 1H), 10.42 (s, 1H), 7.52 (d, 1H), 7.29 (m, 1H), 7.22 (m, 1H), 6.50 (s, 1H), 6.38 (s, 1H), 3.72 (m, 4H), 3.42 (m, 4H). LRMS (APCI, negative): Da/e 312.4 (m−1).

EXAMPLE 18 (INTERMEDIATE)

4-(3,5-Dimethoxyphenyl)morpholine

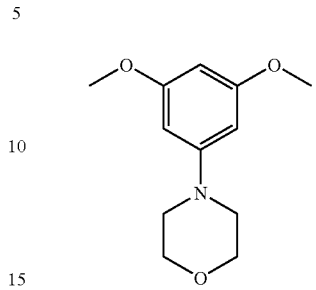

A solution of 2,5-dihydrofuran (29.74 g, 424.3 mmol) in methanol (650 mL) was cooled to −78° C. and treated with ozone until a blue color persisted. The vessel then was purged with oxygen and treated with sodium cyanoborohydride (652.8 mL, 1.0 M in THF). After stirring the reaction mixture for 15 minutes, 3,5-dimethoxyaniline (50.0 g, 326.4 mmol) was added, and the reaction mixture was allowed to worm to room temperature slowly and stored overnight. The reaction mixture was adjusted to pH 4 with acetic acid (100 mL) and concentrated to an orange colored semisolid. The residue was dissolved in EtOAc (2 L) and washed with saturated NaHCO$_3$ (3×100 mL) and brine. The organics were dried (MgSO$_4$), then concentrated to produce an oil. The oil then was purified via chromatography using 10% EtOAc/hexanes to yield 51.2 g (70%) of 4-(3-5-dimethoxyphenylmorpholine as a white (solid). R$_f$=0.55 (50% EtOAc/hexanes). $^1$H NMR (CDCl3, 400 MHz) δ: 6.10 (s, 2H), 6.05 (s, 1H), 3.85 (m, 4H), 3.78 (s, 6H), 3.15 (m, 4H). $^{13}$C (CDCl$_3$, 100 MHz) δ: 161.9, 153.1, 95.1, 92.4, 66.9, 55.4, 49.5.

EXAMPLE 19 (INTERMEDIATE)

5-Morpholin-4-yl-benzene-1,3-diol

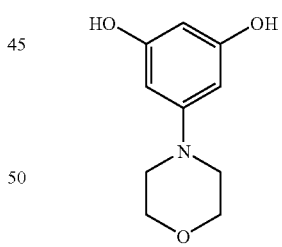

To a 330 mL mixture of 1:1 acetic acid and hydrobromic acid (48%) was added the compound of Example 18 (9.4 g, 42.1 mmol). The resulting mixture was refluxed for 2.5 h. The reaction then was allowed to cool to RT, and adjusted to pH 6 with 50% NaOH (240 mL). The aqueous layer was extracted with EtOAc (6×100 mL), and the organic layers were combined and washed with water (1×100 mL) and brine (1×100 mL). After drying (Na$_2$SO$_4$), the mixture then was filtered through a silica gel (60 Å) plug and washed with EtOAc (600 mL). The filtrate was concentrated to a light brown solid to provide 7.6 g (93%) of 5-morpholin-4-yl-benzene-1,3-diol. R$_f$=0.25 (50% EtOAc/hexanes). $^1$H NMR (DMSO-d$_6$, 400 MHz) δ: 8.95 (s, 2H), 5.77 (s, 2H), 5.73 (m, 1H), 3.68 (m, 4H), 2.96 (m, 4H). ¹³C NMR (DMSO-d₆, 400 MHz) δ: 159.4, 153.8, 95.1, 94.5, 66.9, 49.0. LRMS (Electrospray, positive): Da/e 196.3 (m+1).

EXAMPLE 20

6-Fluoro-1-hydroxy-3-morpholin-4-yl-xanthen-9-one

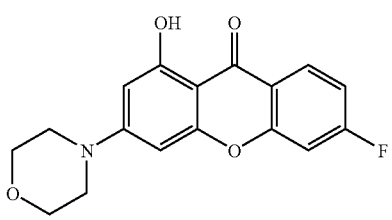 [SMILES: O=c1c2ccc(F)cc2oc2cc(N3CCOCC3)cc(O)c12]

A mixture of the compound of Example 19 (500 mg, 2.56 mmol) and 4-fluoro-2-hydroxy-benzoic acid (800 mg, 5.12 mmol) in diphenyl ether was refluxed for 1 h. The resulting solution was purified via Biotage chromatography using 10% EtOAc/hexanes as eluent to yield 60 mg (7%) of 6-fluoro-1-hydroxy-3-morpholin-4-yl-xanthen-9-one as a yellow solid. R_f=0.50 (50% EtOAc/hexanes). ¹H NMR (DMSO-d₆, 400 MHz) δ: 12.63 (s, 1H), 8.17 (dd, 1H), 7.49 (d, 1H), 7.32 (dd, 1H), 6.53 (s, 1H), 6.37 (s, 1H), 3.72 (m, 4H), 3.43 (m, 4H). LRMS (APCI, positive): Da/e 316.3 (m+1).

GENERAL PROCEDURE FOR ARYL FLUORIDE DISPLACEMENTS FOR EXAMPLES 21-23

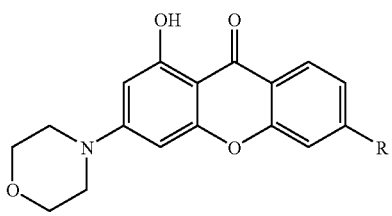

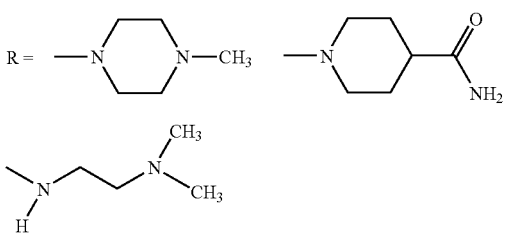

The desired amine (0.288 mmol) and the compound of Example 20 (30 mg, 0.095 mmol) in DMSO (1.5 mL) were heated at 80° C. for 16 h. The reaction then was diluted with EtOAc (150 mL), washed with water (6×5 mL) and brine (1×20 mL), dried MgSO₄, and concentrated to provide the crude product.

EXAMPLE 21

1-Hydroxy-6-(4-methylpiperazin-1-yl)-3-morpholin-4-yl-xanthen-9-one

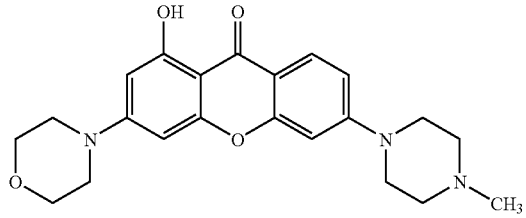 [SMILES: CN1CCN(c2ccc3c(=O)c4c(O)cc(N5CCOCC5)cc4oc3c2)CC1]

The crude reaction residue then was purified via Biotage chromatography using 10% MeOH/EtOAc as eluent to yield 23 mg (61%) of 1-hydroxy-6-(4-methylpiperazin-1-yl)-3-morpholin-4-yl-xanthen-9-one as a light brown solid. R_f=0.30 (100% EtOAc). ¹H NMR (CDCl₃, 400 MHz) δ: 13.02 (s, 1H), 8.03 (d, 1H), 6.87 (d, 1H), 6.64 (s, 1H), 6.23 (s, 1H), 6.21 (s, 1H), 3.85 (m, 4H), 3.42 (m, 4H), 3.34 (m, 4H), 2.58 (m, 4H), 2.37 (s, 3H). LRMS (APCI, positive): 396.3 (m+1).

EXAMPLE 22

1-(8-Hydroxy-6-morpholin-4-yl-9-oxo-9H-xanthen-3-yl)-piperidine-4-carboxylic acid amide

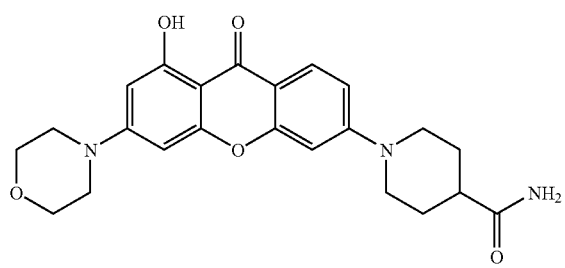 [SMILES: NC(=O)C1CCN(c2ccc3c(=O)c4c(O)cc(N5CCOCC5)cc4oc3c2)CC1]

The crude reaction residue then was purified via Biotage chromatography using 15% MeOH/EtOAc as eluent to yield 6 mg (15%) of 1-(8-hydroxy-6-morpholin-4-yl-9-oxo-9H-xanthen-3-yl)-piperidine-4-carboxylic acid amide as a light brown solid. R_f=0.20 (100% EtOAc). ¹H NMR (DMSO-d₆, 400 MHz) δ: 13.09 (s, 1H), 7.85 (d, 1H), 7.31 (s, 1H), 7.05 (d, 1H), 6.80 (s, 2H), 6.39 (s, 1H), 6.29 (s, 1H), 4.04 (m, 2H), 3.73 (m, 4H), 3.36 (m, 4H), 3.00 (t, 2H), 2.40 (m, 1H), 1.79 (m, 2H), 1.59 (m, 2H). LRMS (APCI, positive): 424.3 (m+1).

EXAMPLE 23

6-[(2-Dimethylaminoethyl)methylamino]-1-hydroxy-3-morpholin-4-yl-xanthen-9-one

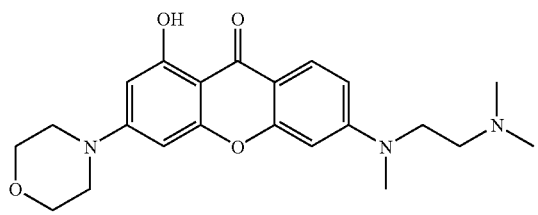 [SMILES: CN(C)CCN(C)c1ccc2c(=O)c3c(O)cc(N4CCOCC4)cc3oc2c1]

The crude reaction residue then was purified via Biotage chromatography using 100% hexanes to 100% EtOAc as eluent to yield 45 mg (87%) of 6-[(2-dimethylaminoethyl)methylamino]-1-hydroxy-3-morpholin-4-yl-xanthen-9-one as a brown solid. $R_f$=0.29 (50% EtOAc/hexanes). ¹H NMR (CDCl₃, 400 MHz) δ: 13.10 (s, 1H), 8.00 (d, 1H), 6.65 (s, 1H), 6.41 (d, 1H), 6.22 (s, 1H), 6.20 (s, 1H), 3.84-3.83 (m, 4H), 3.55 (t, 2H), 3.33-3.20 (m, 4H), 3.08 (s, 3H), 2.54 (s, 2H), 2.32 (s, 6H). LRMS (APCI, negative): 396.3 (m−1).

EXAMPLE 24 (INTERMEDIATE)

(2,3-Difluorophenyl)-(2,6-dihydroxy-4-morpholin-4-yl-phenyl)methanone

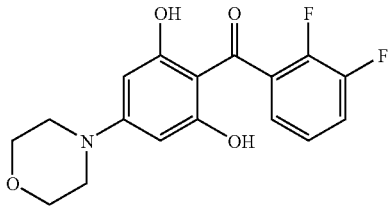 [SMILES: O=C(c1cccc(F)c1F)c1c(O)cc(N2CCOCC2)cc1O]

Aluminum chloride (905 mg, 6.79 mmol) was added to a solution of 5-morpholin-4-yl-benzene-1,3-diol in nitrobenzene (8 mL), and the mixture was heated to 110° C. A solution of 2,3-difluorobenzoyl chloride in nitrobenzene was added slowly, and the mixture was heated at 100° C. for 12 h. The majority of the nitrobenzene was removed via short-path vacuum distillation. The black residue was dissolved in water/EtOAc (1:1, 20 mL). The aqueous component was extracted with EtOAc (3×40 mL), and the combined extracts were dried (MgSO₄) and filtered through a ¾-inch silica gel plug. The filtrate was concentrated and purified via Biotage chromatography (100% hexanes to 30% EtOAc/hexanes) to yield 196 mg (22%) of (2,3-difluorophenyl)-(2,6-dihydroxy-4-morpholin-4-yl-phenyl)methanone. ¹H NMR (CDCl₃, 400 MHz) δ: 7.30-7.10 (comp., 3H), 5.85 (s, 2H), 3.85-3.75 (m, 4H), 3.42-3.38 (m, 4H).

EXAMPLE 25

5-Fluoro-1-hydroxy-3-morpholin-4-yl-xanthen-9-one

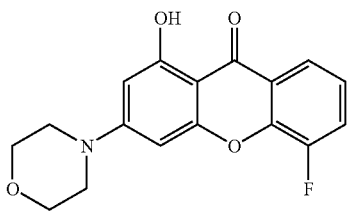 [SMILES: O=c1c2cccc(F)c2oc2cc(N3CCOCC3)cc(O)c12]

Sodium hydride (24 mg, 1.0 mmol, 60%) was added to a solution of a compound of Example 24 (168 Mg, 0.50 mmol) in DMF (2 mL), then the mixture was heated at 75° C. for 4 h. The reaction was cooled to 22° C., and EtOAc (70 mL) was added to produce a yellow precipitate. The precipitate was filtered and dried to yield 10 mg (7%) of 5-fluoro-1-hydroxy-3-morpholin-4-yl-xanthen-9-one. ¹H NMR (CDCl₃, 400 MHz) δ: 12.59 (s, 1H), 7.95 (d, 1H), 7.75 (m, 1H), 7.40 (m, 1H), 6.60 (s, 1H), 6.38 (s, 1H), 3.65-3.63 (m, 4H), 3.40-3.38 (m, 4H). LRMS (APCI, positive): 316.3 (m+1).

EXAMPLE 26

Trifluoromethanesulfonic acid 1-hydroxy-9-oxo-9,10-dihydro-acridin-3-yl ester

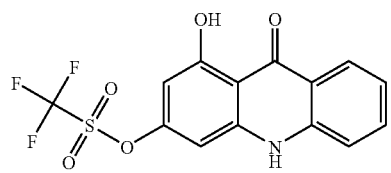 [SMILES: O=c1c2ccccc2[nH]c2cc(OS(=O)(=O)C(F)(F)F)cc(O)c12]

Trifluoromethanesulfonic anhydride (3.1 mL, 18.4 mmol) was slowly added to a solution of 1,3-dihydroxy-10H-acridin-9-one (4.0 g, 17.6 mmol), and 2,6-lutidine (65 mL) in CH₂Cl₂ (180 mL) at 0° C. See J. Reisch et al., *Liebigs Ann. Chem.*, pp. 685-689 (1991). The reaction then was allowed to slowly warm to room temperature. After 16 h, the reaction was concentrated, redissolved in EtOAc (250 mL), and washed with 10% citric acid (5×50 mL) water (2×25 mL), and brine (2×25 mL). The organics then were dried (Na₂SO₄), filtered, and concentrated. The crude material then was purified via Biotage chromatography using 5% EtOAc/hexanes as eluent to yield 1.77 g (28%) of trifluoromethanesulfonic acid 1-hydroxy-9-oxo-9,10-dihydro-acridin-3-yl ester as an orange solid. $R_f$=0.50 (50% EtOAc/hexanes). ¹H NMR (DMSO-d₆, 400 MHz) δ: 12.45 (s, 1H), 8.25 (d, 1H), 7.87 (dd, 1H), 7.59 (d, 1H), 7.40 (dd, 1H), 6.99 (s, 1H), 6.67 (s, 1H).

EXAMPLE 27

1-Hydroxy-3-morpholin-4-yl-10H-acridin-9-one

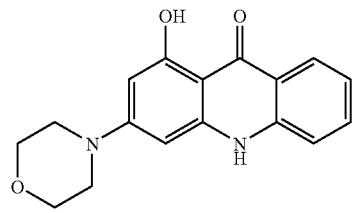 [SMILES: O=c1c2ccccc2[nH]c2cc(N3CCOCC3)cc(O)c12]

A suspension of the compound of Example 26 (1.015 g, 2.83 mmol), potassium phosphate (1.19 g, 5.61 mmol), tris(dibenzylideneacetone)dipalladium(0) (0.130 g, 0.142 mmol), biphenyl-2-yl-di-tert-butylphosphane (0.173 g, 0.580 mmol), and morpholine (0.292 mL, 3.34 mmol) in THF (2.5 mL) was heated at 75° C. for 4 h. The reaction was filtered through a silica gel (60 Å) plug and washed with EtOAc (3×50 mL). The filtrate was concentrated and recrystallized using EtOAc/hexanes to yield 48 mg (6%) of 1-hydroxy-3-morpholin-4-yl-10H-acridin-9-one. $R_f$=0.40 (50% EtOAc/hexanes). ¹H NMR (DMSO-d₆, 400 MHz) δ: 11.66 (s, 1H), 8.12 (d, 1H), 7.69 (dd, 1H), 7.45 (d, 1H), 7.23 (dd, 1H), 6.20 (s, 2H), 3.75 (m, 4H), 3.30 (m, 4H). LRMS (Electrospray, positive): 297.3 (m+₁).

EXAMPLE 28

10-Benzyl-1-hydroxy-3-morpholin-4-yl-10H-acridin-9-one

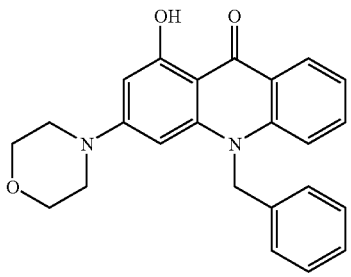 [SMILES: O=c1c2ccccc2n(Cc2ccccc2)c2cc(N3CCOCC3)cc(O)c12]

Benzyl bromide (0.020 mL, 0.15 mmol) was added to a suspension of the compound of Example 27 (45 mg, 0.152 mmol) and $K_2CO_3$ (42 mg. 0.304 g) in NMP (2 mL). After 15 h, additional benzyl bromide (0.02 mL, 0.152 mmol) was added, and after an additional 5 h, the reaction was heated to 80° C. After 20 h; water was added and the aqueous layer was extracted with EtOAc (3×20 mL). The combined organics were dried ($MgSO_4$) then concentrated to yield an oil, which was purified via Biotage chromatography (100% hexanes to 30% EtOAc/hexanes) to, yield 11 mg (20%) of 10-benzyl-1-hydroxy-3-morpholin-4-yl-10H-acridin-9-one. $^1$H NMR ($CDCl_3$, 400 MHz) δ: 8.49 (d, 1H), 7.60 (dd, 1H), 7.40-7.21 (m, 7H), 6.24 (s, 1H), 5.98 (s, 1H), 5.48 (s, 2H), 3.77 (m, 4H), 3.22 (m, 4H). LRMS (APCI, positive): 387.3 (m+1).

EXAMPLE 29

10-Benzoyl-1-hydroxy-3-morpholin-4-yl-10H-acridin-9-one

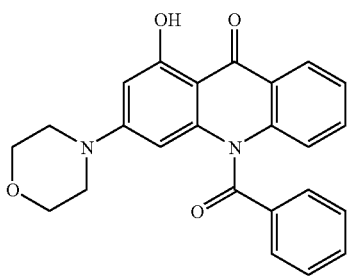 [SMILES: O=C(c1ccccc1)n1c2ccccc2c(=O)c2c(O)cc(N3CCOCC3)cc21]

1-Hydroxy-3-morpholin-4-yl-10H-acridin-9-one (50 mg, 0.17 mmol) was slurried in DMF (00.5 mL), then benzoyl chloride (21.6 μL, 0.19 mmol) and NaH (8.0 mg, 60% by weight, 0.20 mmol) were added. The reaction was stirred at 22° C. for 24 h. The reaction was quenched with saturated $NH_4Cl$, then EtOAc was added. The layers were separated, and the organics were washed with saturated $NaHCO_3$, water, and saturated NaCl, then dried over $Na_2SO_4$ and concentrated to an orange residue (70 mg). This material was chromatographed on $SiO_2$ using EtOAc/hexanes (1:1) to recover the desired lower fraction ($R_f$=0.17, EtOAc/hexanes (2:1), 10-benzoyl-1-hydroxy-3-morpholin-4-yl-10H-acridin-9-one (20.7 mg, 30%) as a yellow solid. $^1$H NMR ($CDCl_3$, 400 MHz) δ: 9.07 (1H), 8.37 (d, 2H), 8.17 (d, 1H), 7.66 (dd, 1H), 7.55 (dd, 2H), 7.41 (dd, 1H), 7.10 (dd, 1H), 6.98 (dd, 1H), 6.17 (s, 1H), 5.88 (1H), 3.64-3.60 (m, 4H), 2.87-2.83 (m, 4H). LRMS (APCI, negative): Da/e 399.3 (m−1).

The following examples were prepared in a similar manner to 10-benzoyl-1-hydroxy-3-morpholin-4-yl-10H-acridin-9-one, using an appropriate acid chloride.

EXAMPLE 30

1-Hydroxy-10-isobutyryl-3-morpholin-4-yl-10H-acridin-9-one

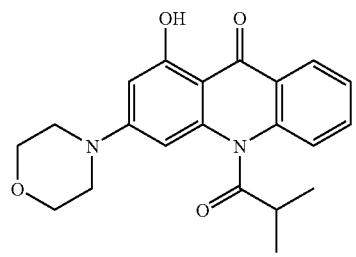 [SMILES: CC(C)C(=O)n1c2ccccc2c(=O)c2c(O)cc(N3CCOCC3)cc21]

This compound ($R_f$ 0.07 in EtOAc/hexanes) was purified by chromatography on $SiO_2$ using EtOAc/hexanes (1:1) as eluent, (4 mg, 7%). $^1$H NMR ($CDCl_3$, 400 MHz) δ: 8.68 (s, 1H), 8.20 (d, 1H), 7.45 (dd, 1H), 7.12 (dd, 1H), 6.94 (d, 1H), 6.04 (s, 1H), 5.82 (s, 1H), 3.67 (s, 4H), 3.20 (m, 1H), 2.90 (s, 4H), 1.50 (d, 6H).

EXAMPLE 31

1-Hydroxy-3-morpholin-4-yl-10-(pyridine-4-carbonyl)-10H-acridin-9-one

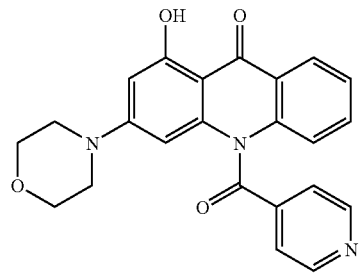 [SMILES: O=C(c1ccncc1)n1c2ccccc2c(=O)c2c(O)cc(N3CCOCC3)cc21]

This compound was purified by filtration of the reaction mixture after quenching with saturated $NH_4Cl$, and dilution with EtOAc. The solids were washed with EtOAc and dried (7 mg, 10%). $^1$H NMR ($CDCl_3$, 400 MHz) δ: 1.81 (s, 1H), 8.91 (d, 2H), 8.04 (d, 2H), 7.95 (d, 1H), 7.62 (m, 1H), 7.47 (m, 1H), 7.12 (m, 1H), 6.83 (d, 1H), 6.76 (d, 1H), 3.77-3.73 (m, 4H), 3.44-3.37 (m, 4H). LRMS (APCI, negative) Da/e 400.4 (m−1).

EXAMPLE 32

1-Hydroxy-3-morpholin-4-yl-10-(pyridine-3-carbonyl)-10H-acridin-9-one

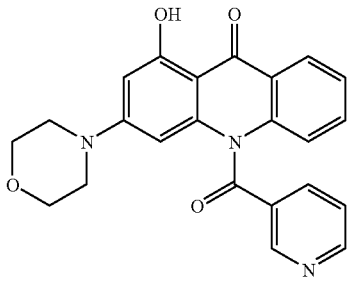 [SMILES: O=C(c1cccnc1)n1c2ccccc2c(=O)c2c(O)cc(N3CCOCC3)cc21]

This compound was purified by chromatography on SiO$_2$ using ethyl acetate (1:1) as eluent (14.2 mg. 20%). $^1$H NMR (CDCl$_3$, 400 MHz) δ: 9.54 (s, 1H), 8.97 (s, 1H), 8.87 (m, 1H), 8.61 (m, 1H), 8.17 (d, 1H), 7.52-7.43 (m, 2H), 7.12 (dd, 1H), 7.03 (d, 1H), 6.24 (s, 1H), 5.95 (s, 1H), 3.68-3.63 (m, 4H), 2.96-2.92 (m, 4H). LRMS (APCI, negative): Da/e 400.2 (m−1).

PRODRUG EXAMPLES

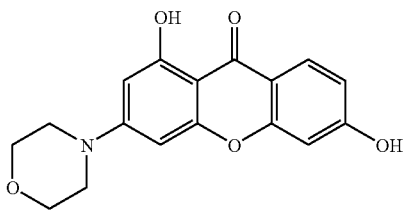 [SMILES: O=c1c2ccc(O)cc2oc2cc(N3CCOCC3)cc(O)c12]

EXAMPLE 11

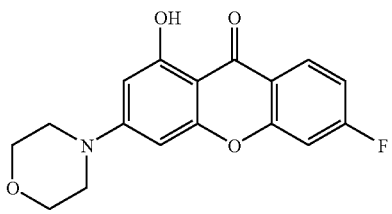 [SMILES: O=c1c2ccc(F)cc2oc2cc(N3CCOCC3)cc(O)c12]

EXAMPLE 19

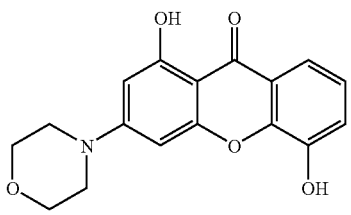 [SMILES: O=c1c2cccc(O)c2oc2cc(N3CCOCC3)cc(O)c12]

EXAMPLE 16

General Procedure for Phosphorylation:

To a cooled (−78° C.) solution of the appropriate phenol (0.223 mmol) in THF (15 mL) was added lithium bis(trimethylsilyl)amide (1.0 M in THF, 0.245 mmol). The resulting mixture was stirred for 15 min, then tetrabenzylpyrophosphate (0.334 mmol), dissolved in THF (1.5 mL), was slowly added. The resulting mixture was allowed to slowly reach 22° C. overnight. The reaction mixture was filtered, and the filtrate concentrated. The resulting solid was dissolved in EtOAc (150 mL), and washed with saturated (NaHCO$_3$ (1×25 mL), water (1×25 mL), and brine (1×25 mL). The organics were dried (MgSO$_4$) and concentrated to yield the crude product.

EXAMPLE 33

Phosphoric acid dibenzyl ester 8-hydroxy-6-morpholin-4-yl-9-oxo-9H-xanthen-3-yl ester

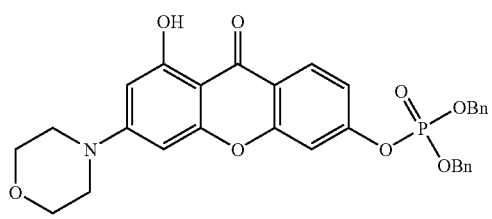

The crude residue then was purified via Biotage chromatography using 50% EtOAc/hexanes as eluent to yield 70 mg (32%) of phosphoric acid dibenzyl ester 8-hydroxy-6-morpholin-4-yl-9-oxo-9H-xanthen-3-yl ester as a yellow solid. $^1$H NMR (CDCl$_3$, 400 MHz) δ: 2.65 (s, 1H), 8.12 (d, 1H), 7.35 (m, 8H), 7.25 (m, 2H), 7.16 (m, 1H), 7.04 (d, 1H), 6.23 (s, 1H), 6.21 (s, 1H), 5.18 (s, 2H), 5.17 (s, 2H), 3.83 (m, 4H), 3.38 (m, 4H). LRMS (APCI, positive): Da/e 574.1 (m+1).

EXAMPLE 34

Phosphoric acid dibenzyl ester 6-fluoro-3-morpholin-4-yl-9-oxo-9H-xanthen-1-yl ester

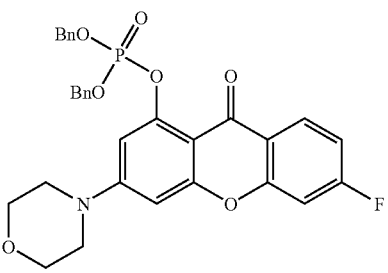

The crude product (yellow oil) then was purified via Biotage chromatography using 15% EtOAc/hexanes as eluent to yield 99 mg (77%) of phosphoric acid dibenzyl ester 6-fluoro-3-morpholin-4-yl-9-oxo-9H-xanthen-1-yl ester as a yellow solid. $^1$H NMR (CDCl$_3$, 400 MHz) δ: 8.25 (m, 1H), 7.38 (m, 5H), 7.30 (m, 5H), 7.02 (m, 2H), 6.73 (s, 1H), 6.50 (s, 1H), 5.35 (m, 4H), 3.88 (m, 4H), 3.19 (m, 4H). LRMS (APCI, positive): Da/e 575.9 (m+1).

EXAMPLE 35

Phosphoric acid dibenzyl ester 8-hydroxy-6-morpholin-4-yl-9-oxo-9H-xanthen-4-yl ester

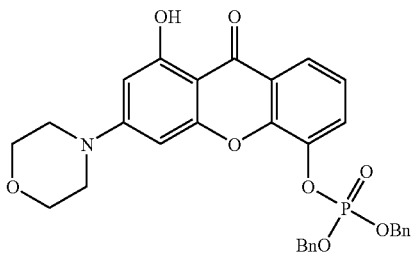 [SMILES: O=c1c2cccc(OP(=O)(OCc3ccccc3)OCc3ccccc3)c2oc2cc(N3CCOCC3)cc(O)c12]

The crude residue then was purified via Biotage chromatography using 5%-50% EtOAc/hexanes as eluent to yield 163 mg (44%) of phosphoric acid dibenzyl ester 8-hydroxy-6-morpholin-4-yl-9-oxo-9H-xanthen-4-yl ester as a yellow solid. $^1$H NMR (DMSO-d$_6$, 400 MHz) δ: 12.58 (s, 1H), 7.91 (d, 1H), 7.70 (d, 1H), 7.35 (m, 1H), 6.36 (s, 1H), 6.28 (s, 1H), 5.30 (s, 2H), 5.28 (s, 2H), 3.68 (m, 4H), 3.31 (m, 4H). LRMS (APCI, positive): Da/e 574.1 (m+1).

EXAMPLE 36

Phosphoric acid dibenzyl ester 3-morpholin-4-yl-9-oxo-9,10-dihydro-acridin-1-yl ester

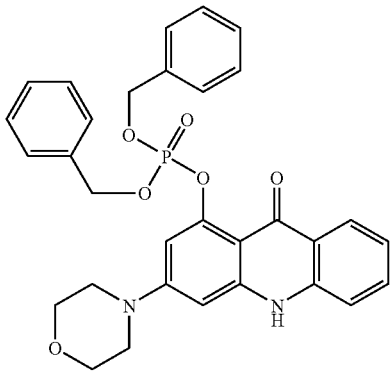 [SMILES: O=c1c2ccccc2[nH]c2cc(N3CCOCC3)cc(OP(=O)(OCc3ccccc3)OCc3ccccc3)c12]

The compound was prepared following the general procedure for phosphate formation utilizing 1-hydroxy-3-morpholin-4-yl-10H-acriding-9-one as starting material. The product was isolated from the reaction mixture by filtration of the insoluble solids formed after quenching with saturated NH$_4$Cl and EtOAc. $^1$H NMR (DMSO-d$_6$, 400 MHz) δ: 11.39 (s, 1H), 8.15 (d, 1H), 7.65-7.61 (m, 1H), 7.43-7.34 (m, 11H), 7.17 (dd, 1H), 6.54 (s, 1H), 6.52 (s, 1H), 5.34 (d, 4H), 3.71 (m, 4H), 3.10 (m, 4H). LRMS (APCI, positive); Da/e 557.3 (m+1).

General Procedure for Debenzylation:

A mixture of the dibenzylphosphate (0.128 mmol), NaHCO$_3$ (0.256 mmol), and 10% Pd/C (0.098 mmol) in a 1:1:1 solution of EtOAc/MeOH/water was stirred under a hydrogen gas atmosphere (balloon) for 3 h. The mixture then was filtered through a nylon filter. The filter cake was washed with water (1×5 mL). The volatile solvents were evaporated and the water was lyophilized.

EXAMPLE 37

Phosphoric acid disodium salt 8-hydroxy-6-morpholin-4-yl-9-oxo-9H-xanthen-3-yl ester

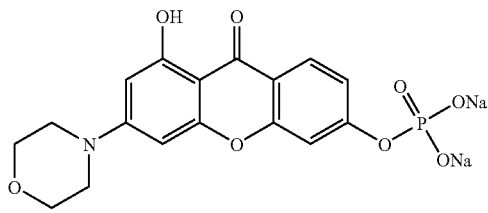

The reaction yielded 46 mg (87%) of phosphoric acid disodium salt ester 8-hydroxy-6-morpholin-4-yl-9-oxo-9H-xanthen-3-yl ester as a light yellow solid. $^1$H NMR (DMSO-d$_6$, 400 MHz) δ: 12.93 (s, 1H), 7.90 (d, 1H), 7.38 (s, 1H), 7.13 (d, 1H), 6.45 (s, 1H), 6.30 (s, 1H), 3.75 (m, 4H); 3.38 (m, 4H).

EXAMPLE 38

Phosphoric acid disodium salt 6-fluoro-3-morpholin-4-yl-9-oxo-9H-xanthen-1-yl ester

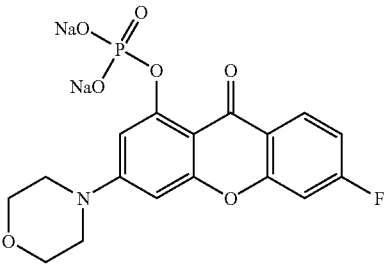

The reaction yielded 61 mg (81%) of phosphoric acid disodium salt ester 6-fluoro-3-morpholin-4-yl-9-oxo-9H-xanthen-1-yl ester as a light yellow solid. $^1$H NMR (D$_2$O, 400 MHz) δ: 8.10 (m, 1H), 7.17 (s, 1H), 7.08 (m, 2H), 6.52 (s, 1H), 3.81 (m, 4H), 3.38 (m, 4H).

EXAMPLE 39

Phosphoric acid disodium salt 8-hydroxy-6-morpholin-4-yl-9-oxo-9H-xanthen-4-yl-ester

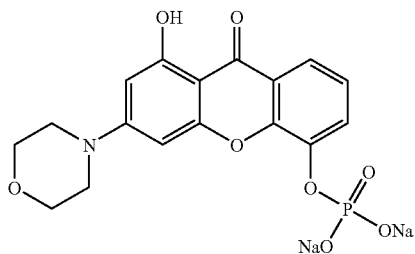

The reaction yielded 53 mg (95%) of phosphoric acid disodium salt ester 8-hydroxy-6-morpholin-4-yl-9-oxo-9H- xanthen-4-yl ester as a light yellow solid. ¹H NMR (CD₃OD, 400 MHz) δ: 8.13 (d, 1H), 7.63 (d, 1H), 7.22 (t, 1H), 6.58 (s, 1H), 6.29 (s, 1H), 3.82 (m, 4H), 3.41 (m, 4H).

EXAMPLE 40

Phosphoric acid disodium salt 3-morpholin-4-yl-9-oxo-9,10-dihydro-acridin-1-yl ester

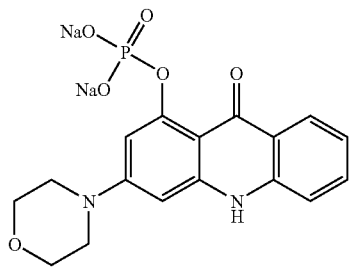

¹H NMR (CD₃OD, 400 MHz) δ: 8.26 (d, 1H), 7.54 (m, 1H), 7.31 (d, 1H), 7.20 (m, 1H), 7.11 (m, 1H), 6.29 (m, 1H), 3.80-3.76 (m, 4H), 3.35-31 (m, 4H).

EXAMPLE 41

1-Hydroxy-3-morpholin-4-yl-6-(pyridin-2-yl-methoxy)-xanthen-9-one

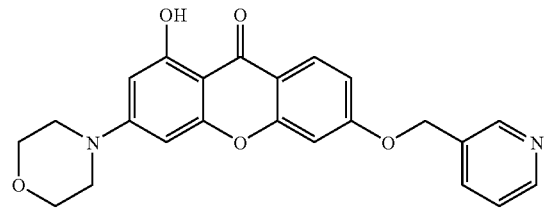 [SMILES: O=c1c2ccc(OCc3cccnc3)cc2oc2cc(N3CCOCC3)cc(O)c12]

6-Fluoro-1-hydroxy-3-morpholin-4-yl-xanthen-9-one (15 mg, 0.05 mmol) and 2-pyridylmethanol (8 mg, 0.07 mmol) were dissolved in DMSO (0.25 mL) and KHMDS (0.5 M in toluene, 0.24 mL) was added. The reaction mixture was heated to 80° C. for 16 hours. The reaction was quenched with sat. NH₄Cl/water (1:1, 2 mL) and the solids were filtered. The crude solid was purified via flash chromatography eluting with CH₂Cl₂/MeOH (98:2) to produce 4.9 mg (25%). ¹H NMR (CDCl₃, 400 MHz) δ: 12.80 (s, 1H), 8.63 (d, 1H), 8.13 (d, 1H), 7.76 (dd, 1H), 7.52 (d, 1H), 7.27-7.24 (m, 1H), 7.02 (d, 1H), 6.88 (s, 1H), 6.27 (s, 1H), 6.23 (s, 1H), 5.31 (s, 2H), 3.86-3.83 (m, 4H), 3.37-3.35 (m, 4H). LRMS (APCI, positive): Da/e 405.1 (m+1).

EXAMPLE 42

1-Hydroxy-3-morpholin-4-yl-6-(pyridin-3-yl-methoxy)-xanthen-9-one

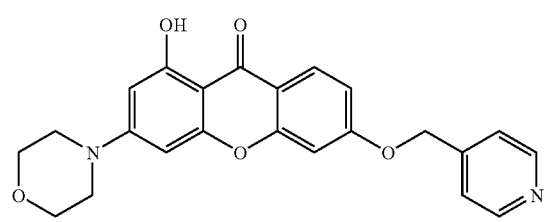 [SMILES: O=c1c2ccc(OCc3ccncc3)cc2oc2cc(N3CCOCC3)cc(O)c12]

6-Fluoro-1-hydroxy-3-morpholin-4-yl-xanthen-9-one (16 mg. 0.05 mmol) and 3-pyridylmethanol (8 mg, 0.07 mmol) were dissolved in DMSO (0.25 mL), and KHMDS (0.5 M in toluene, 0.24 mL) was added. The reaction mixture was heated to 80° C. for 16 hours, then stirred at room temperature for 60 hours. The reaction was quenched with sat. NH₄Cl/water (1:1, 2 mL) and the solids were filtered. The crude solid was purified via flash chromatography eluting with CH₂Cl₂/MeOH (98:2) to yield 6.8 mg (34%) of product. ¹H NMR (CDCl₃, 400 MHz) δ: 12.80 (s, 1H), 8.73 (s, 1H), 8.64 (d, 1H), 8.15 (d, 1H), 7.80 (d, 1H), 7.36 (dd, 1H), 6.97 (dd, 1H) 6.85 (s, 1H), 6.27 (s, 1H), 6.24 (s, 1H), 5.19 (s, 2H), 3.86-3.83 (m, 4H), 3.37-3.35 (m, 4H). LRMS (APCI, positive): Da/e 405.1 (m+1).

EXAMPLE 43

1-Hydroxy-3-morpholin-4-yl-6-(pyridin-4-yl-methoxy)-xanthen-9-one

6-Fluoro-1-hydroxy-3-morpholin-4-yl-xanthen-9-one (16 mg, 0.05 mmol) and 4-pyridylmethanol (8 mg, 0.07 mmol) were dissolved in DMSO (0.25 mL) and KHMDS (0.5 M in toluene, 0.24 mL) was added. The reaction mixture was heated at 80° C. for 16 hours. The reaction mixture wad quenched with sat. NH₄Cl/water (1:1, 2 mL) and the solids were filtered. The solid was purified via flash chromatography eluting with CH₂Cl₂/MeOH (98:2) to produce 3.9 mg (20%). ¹H NMR (CDCl₃, 400 MHz) δ: 12.80 (s, 1H), 8.66 (s, 2H), 8.16 (d, 1H), 7.38 (d, 2H), 7.00 (d, 1H), 6.80 (s, 1H), 6.27 (dd, 1H), 6.25 (s, 1H), 5.21 (s, 2H), 3.86-3.83 (m, 4H), 3.37-3.35 (m, 4H). LRMS (APCI, positive): Da/e 405.1 (m+1).

EXAMPLE 44

6-Hydroxy-8-morpholin-4-yl-10H-benzo[b][1,8]naphthyridin-5-one

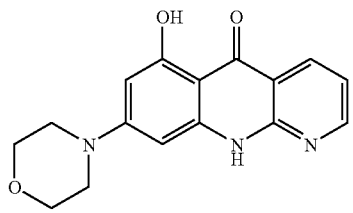 [SMILES: O=c1c2cccnc2[nH]c2cc(N3CCOCC3)cc(O)c12]

5-Morpholin-4-yl-benzene-1,3-diol (345 mg 1.77 mmol), TsOH.H₂O (30 mg, 0.20 mmol), and 2-aminonicotinic acid methyl ester (269 mg, 1.77 mmol) were heated at 160° C. in hexanol (5 mL) for 12 hours. Upon cooling, the mixture was purified via flash chromatography CH$_2$Cl$_2$/MeOH (95:5), followed by a second flash column eluting with Et$_2$OAc/hexanes (7:3) to provide 11 mg (2%) of the product. $^1$H NMR (CDCl$_3$, 400 MHz) δ: 13.5 (s, 1H), 8.80 (br s, 1H), 8.62 (d, 1H), 7.25 (dd, 1H), 6.22 (d, 1H), 6.04 (s, 1H), 5:97 (s, 1H), 3.86-3.83 (m, 4H), 3.40-3.35 (m, 4H). LRMS (APCI, positive): Da/e 296.4 (m−1).

EXAMPLE 45

8-Hydroxy-6-morpholin-4-yl-9-oxo-9,10-dihydro-acridine-3-carboxylic acid hexyl ester

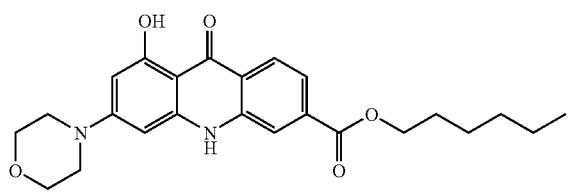 [SMILES: CCCCCCOC(=O)c1ccc2c(=O)c3c(O)cc(N4CCOCC4)cc3[nH]c2c1]

5-Morpholin-4-yl-benzene-1,3-diol (290 mg, 1.50 mmol), TsOH.H₂O (30 mg, 0.20 mmol), and 2-amino-terephthalic acid 1-methyl ester (290 mg, 1.50 mmol) were heated at 160° C. in hexanol (5 mL) for 12 hours. The reaction mixture was cooled to room temperature. A red/orange precipitate was filtered, and the solid washed with EtOAc/hexanes (3:1, 30 mL) to yield 159 mg (31%). $^1$H NMR (CDCl$_3$, 400 MHz) δ: 13.90 (s, 1H), 11.9 (s, 1H), 8.22 (d, 1H), 8.07 (s, 1H), 7.68 (d, 1H), 6.27 (s, 1H), 6.19 (s, 1H), 4.33 (t, 2H), 3.74-3.64 (m, 4H), 3.33-3.22 (m, 4H), 1.76-1.73 (m, 2H), 1.54-1.20 (m, 6H), 0.89 (5, 3H). LRMS (APCI, positive): Da/e 425.2 (m+1).

EXAMPLE 46

8-Hydroxy-6-morpholin-4-yl-9-oxo-9,10-dihydro-acridine-3-carboxylic acid 2-dimethylaminoethyl ester

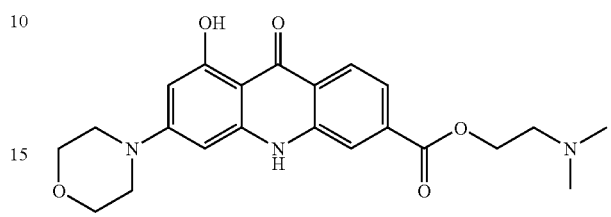

8-Hydroxy-6-morpholin-4-yl-9-oxo-9,10-dihydro-acridine-3-carboxylic acid hexyl ester in. N,N-dimethylethanolamine (2 mL) was heated at 13.0° C. in sealed tube for 12 hours. Hexane (5 mL) was added, and a dark solid formed. The suspension was filtered and the remaining solid triturated with acetone. All residues were dissolved in MeOH and concentrated. The concentrate was purified via flash chromatography (CH$_2$Cl$_2$ to MeOH/CH$_2$Cl$_2$, 5:95) to yield an orange solid (10 mg, 27%). $^1$H NMR (CDCl$_3$, 400 MHz) δ: 13.82 (s, 1H), 11.84 (s, 1H), 8.19 (d, 1H), 8.04 (s, 1H), 7.66 (d, 1H), 6.24 (s, 1H), 6.16 (s, 1H), 4.41 (t, 2H), 3.74-3.64 (m, 4H), 3.33-3.22 (m, 4H), 2.64 (t, 2H), 2.48 (s, 6H) LRMS (APCI, positive): Da/e 412.1 (m+1).

EXAMPLE 47

6-(2-Dimethylaminoethoxy)-1-hydroxy-3-morpholin-4-yl-xanthen-9-one

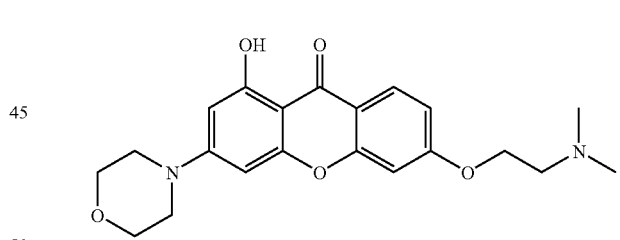

A suspension of KH (about 3 mg, 30-35% by weight in mineral oil) was added to a solution of N,N-dimethylethanolamine (14 mg, 0.16 mmol) and 6-fluoro-1-hydroxy-3-morpholin-4-yl-10H-acridin-9-one (25 mg, 0.08 mmol) in DMSO (1.0 mL), and the reaction mixture was heated at reflux for 4 hours. After cooling, the mixture was diluted with EtOAc and sat. NH$_4$Cl. The organic layer was washed six times with water. The organics were dried (Na$_2$SO$_4$), then concentrated. The concentrate was purified via flash chromatography to yield 4 mg (13%). $^1$H NMR (CDCl$_3$, 400 MHz) δ: 12.94 (s, 1H), 8.11 (d, 1H), 6.93 (d, 1H), 6.81 (s, 1H), 6.25 (d, 1H), 4.17 (t, 3H), 3.86-3.84 (m, 4H), 3.37-3.35 (m, 4H), 2.80 (t, 2H), 2.39 (s, 6H). LRMS (APCI, positive): Da/e 384.5 (m+1).

EXAMPLE 48

1-Hydroxy-6-(2-hydroxyethyl)-3-morpholin-4-yl-xanthen-9-one

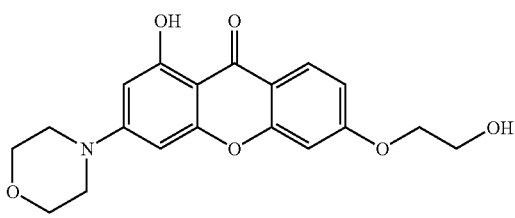 [SMILES: O=c1c2ccc(OCCO)cc2oc2cc(N3CCOCC3)cc(O)c12]

A solution of 6-fluoro-1-hydroxy-3-morpholin-4-yl-xanthen-9-one (30.0 mg, 0.095 mmol) and ethylene glycol (59.1 mg, 0.951 mmol) in anhydrous DMF (1 mL) was treated with NaH (40.0 mg, 0.951 mmol). The bubbling reaction was stirred for 15 minutes at room temperature, then heated at 80° C. for 1 hour. The reaction mixture was quenched with water and extracted with EtOAc (3×50 mL). The combined organics were washed with water (3×15 mL), dried (MgSO$_4$), and concentrated to produce an oil. The oil was purified via Biotage chromatography using a gradient of 2.5%-5% MeOH/CH$_2$Cl$_2$ as eluent to yield 12 mg (35%) of 1-hydroxy-6-(2-hydroxyethoxy)-3-morpholin-4-yl-xanthen-9-one as a white powder. R$_f$=0.55 (5% MeOH/CH$_2$Cl$_2$). $^1$H NMR (DMSO-d$_6$, 400 MHz) δ: 12.91 (s, 1H), 8.05 (d, 1H), 7.10 (m, 2H), 6.48 (s, 1H), 6.34 (s, 1H), 4.98 (m, 1H), 4.18 (t, 2H), 3.78 (t, 2H), 3.70 (m, 4H), 3.38 (m, 4H). LRMS (APCI, positive): Da/e 358.4 (m+1).

EXAMPLE 49 (INTERMEDIATE)

Phosphoric acid dibenzyl ester 2-bromoethyl ester

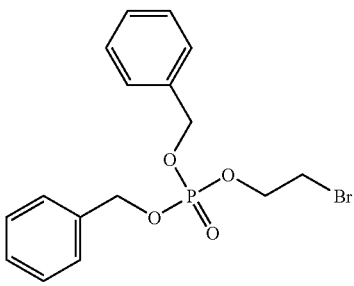 [SMILES: O=P(OCCBr)(OCc1ccccc1)OCc1ccccc1]

To a solution of phosphorous oxychloride (1.5 g, 9.783 mmol) in CH$_2$Cl$_2$ (30 mL) at 0° C. was added NEt$_3$ (11 mL, 78.26 mmol). 2-Bromoethanol (1.22 g, 9.78 mmol) was added, and the resulting solution was stirred at room temperature for hour. Benzyl alcohol (4.232 g, 39.13 mmol) was added, then the reaction mixture was stirred at room temperature 1.5 for 76 hours. The reaction mixture was diluted with water/CH$_2$Cl$_2$ (1:2, 450 mL), and the phases were separated. The organic layer was washed with water (2×50 mL), saturated NH$_4$Cl (2×50 mL), saturated NH$_4$Cl at pH 2 via 10% citric acid (1×50 mL), 6% NaHCO$_3$ (2×50 mL), then dried (Na$_2$SO$_4$) and filtered. The filtrate was concentrated to an oil and purified via Biotage chromatography using 30% EtOAc in hexanes as eluent to yield 520 mg (14%) of phosphoric acid dibenzyl ester 2-bromoethyl ester as a colorless oil. $^1$H NMR (CDCl$_3$, 400 MHz) δ: 7.36 (m, 10H), 5.05 (m, 4H), 4.21 (m, 2H), 3.40 (m, 2H). LRMS (APCI, positive): Da/e 386.3 (m+1).

EXAMPLE 50

Phosphoric acid dibenzyl ester 2-(8-hydroxy-6-morpholin-4-yl-9-oxo-9H-xanthen-3-yloxy)ethyl ester

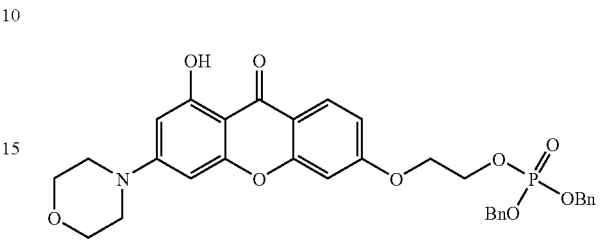

A solution of 1,6-dihydroxy-3-morpholin-4-yl-xanthen-9-one in anhydrous DMF (2.0 mL) was treated with sodium hydride (27.7 mg, 0.693 mmol). After 15 minutes, a solution of phosphoric acid dibenzyl ester 2-bromoethyl ester (267.0 mg, 0.693 mmol) in DMF (1.0 mL), was added, and reaction mixture was stirred overnight at room temperature. The reaction mixture then was dissolved in EtOAc (250 mL) and washed with water (6×50 mL) and brine (1×50 mL). The organics were dried. (Na$_2$SO$_4$) and concentrated. The residue then was purified via Biotage chromatography using 80% EtOAc in hexanes as, eluent to yield 132 mg (31%) of phosphoric acid dibenzyl ester 2-(8-hydroxy-6-morpholin-4-yl-9-oxo-9H-xanthen-3-yloxy)-ethyl ester as a white solid. $^1$H NMR (CDCl$_3$, 400 MHz) δ: 12.82 (s, 1H), 8.12 (d, 1H), 7.34 (m, 10H), 6.82 (d, 1H), 6.73 (s, 1H), 6.24 (s, 1H), 6.22 (s, 1H), 5.04 (m, 4H), 4.38 (m, 2H), 4.18 (m, 2H), 3.83 (m, 4H), 3.38 (m, 4H).

EXAMPLE 51

Phosphoric acid disodium salt (2-(8-hydroxy-6-morpholin-4-yl-9-oxo-9H-xanthen-3-yloxy)ethyl) ester

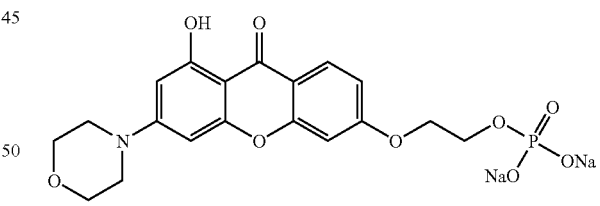

A mixture of the phosphoric acid dibenzyl ester 2-(8-hydroxy-6-morpholin-4-yl-9-oxo-9H-xanthen-3-yloxy)ethyl ester (132.0 mg, 0.2137 mmol), NaHCO$_3$ (35.91 mg, 0.42-75 mmol), and 10% Pd/C (20 mg) in a 1:1:1 solution of EtOAc/MeOH/H$_2$O was stirred under a hydrogen gas atmosphere (balloon) for 3 hours. The mixture then was filtered through a pad of celite on a nylon filter. The filter cake was washed with water (1×10 mL). The volatile solvents were evaporated, and the water was lyophilized to yield 108 mg (99%) of an off-white colored fluffy solid. $^1$H NMR (D$_2$O, 400 MHz) δ: 7.41 (d, 1H), 6.59 (d, 1H), 6.32 (s, 1H), 5.69 (s, 1H), 5.63 (s, 1H), 44.08 (m, 2H), 4.01 (m, 2H), 3.62 (m, 4H), 3.01 (m, 4H).

Obviously, many modifications and variations of the invention as hereinbefore set forth can be made without departing from the spirit and scope thereof, and, therefore, only such limitations should be imposed as are indicated by the appended claims.

The entire contents of the Sequence Listing, .txt file, are incorporated herein by reference.

What is claimed is:

1. A compound having a formula

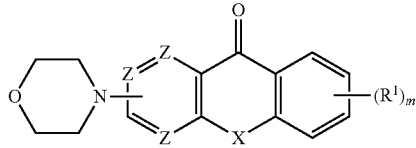

or a pharmaceutically acceptable salt thereof, wherein m is an integer 0 through 3;

X is O, $S(O)_{0-2}$, or $NR^a$;

Z, independently, is $CR^b$ or N;

$R^1$, independently, is selected from the group consisting of halo, alkyl, substituted alkyl, cycloalkyl, substituted cycloalkyl, heterocycloalkyl, substituted heterocycloalkyl, $N(R^d)_2$, $OR^d$, carboxy, wherein the carboxy is not carboxyl, nitro, $OC_{1-3}$alkyleneN$(R^d)_2$, $N(R^d)$—$C_{1-3}$alkyleneN$(R^d)_2$, $OC_{1-3}$alkyleneC(=O)OR$^d$, $O(C_{1-3}$alkylene)OP(=O)(OR$^d)_2$, $O(C_{1-3}$alkylene)OP(=O)(ONa)$_2$, OP(=O)—(OR$^d)_2$, OP(=O)(ONa)$_2$, cyano, aldehyde, carboxamide, thiocarboxamide, acyl, mercapto, sulfonyl, trifluoromethyl, aryl, substituted aryl, heteroaryl, and substituted heteroaryl; or two $R^1$ groups are taken together with the atoms to which each is attached to form a 5-, 6-, or 7-membered ring, wherein 1 or 2 carbon atoms of $R^1$ optionally is a heteroatom selected from the group consisting of O, N, and S, said ring optionally substituted with one or more =O, =S, =NH, $OR^d$, $N(R^d)_2$, carboxyl, carboxy, alkyl, aryl, substituted aryl, heteroaryl, or substituted hetercaryl, said heteroatom optionally substituted with a group selected from the group consisting of aryl, substituted aryl, alkyl, substituted alkyl, and acyl;

$R^a$ is selected from the group consisting of hydro, $C_{1-4}$alkyl, aryl, heteroaryl, cycloalkyl, heterocycloalkyl, $C_{1-3}$alkylenearyl, $C_{1-3}$alkyleneheteroaryl, $C_{1-3}$alkyleneheterocycloalkyl, $C_{1-4}$alkylene-N$(R^d)_2$, $C_{1-4}$alkylene-OR$^d$, $C_{1-4}$alkyleneC(=O)OR$^d$, C(=O)R$^d$, C(=O)N$(R^d)_2$, C(=O)OR$^d$, C(=O)SR$^d$, C(=S)N$(R^d)_2$, SO$_2$R$^d$, SO$_2$N$(R^d)_2$, C(=O)NR$^d$C$_{1-4}$alkyleneOR$^d$, C(=O)NR$^d$C$_{1-4}$alkyleneheterocycloalkyl, C(=O)C$_{1-4}$alkylenearyl, C(=O)C$_{1-4}$alkyleneheteroaryl, $C_{1-4}$alkyleneC(=O)C$_{1-4}$alkylenearyl, $C_{1-4}$alkyleneC(=O)C$_{1-4}$alkyleneheteroaryl, $C_{1-4}$alkylene-C(=O) heterocycloalkyl, $C_{1-4}$alkyleneNR$^d$C(=O)R$^d$, $C_{1-4}$alkyleneOC$_{1-4}$alkyleneOR$^d$, $C_{1-4}$alkyleneOC$_{1-4}$alkyleneC(=O)OR$^d$, and $C_{1-4}$alkyleneC(=O)N$(R^d)_2$;

$R^b$, independently, is selected from the group consisting of hydro, alkyl, halo, aldehyde, $OR^d$, $O(C_{1-3}$alkylene)OP(=O)(OR$^d)_2$, $O(C_{1-3}$alkylene)OP(=O)(ONa)$_2$, OP(=O)(OR$^d)_2$, OP(=O)(ONa)$_2$, nitro, $N(R^d)_2$, carboxyl, carboxy, sulfonamido, sulfamyl, and sulfo; and $R^d$, independently, is selected from the group consisting of hydro, alkyl, substituted alkyl, cycloalkyl, substituted cycloalkyl, heterocycloalkyl, substituted heterocycloalkyl, aryl, $C_{1-3}$alkylenearyl, substituted aryl, heteroaryl, and substituted heteroaryl.

2. The compound of claim 1 having a structure

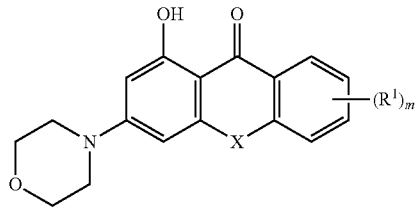

or a pharmaceutically acceptable salt thereof.

3. The compound of claim 1 selected from the group consisting of:
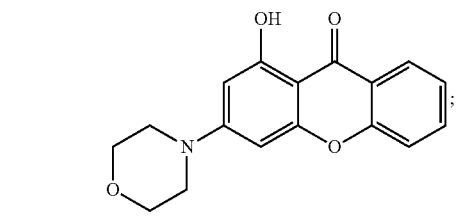
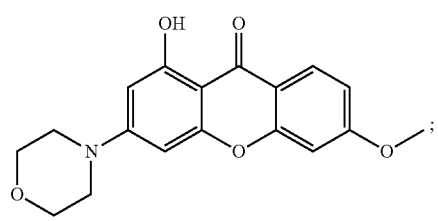
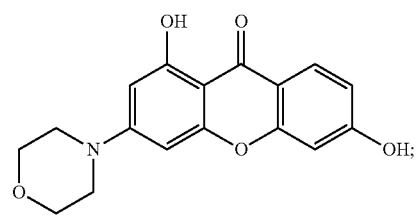
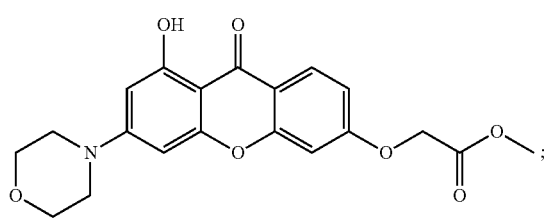
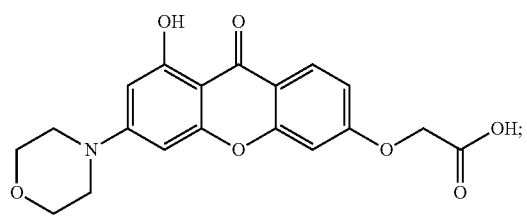
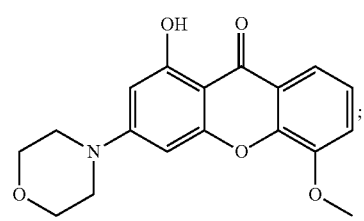
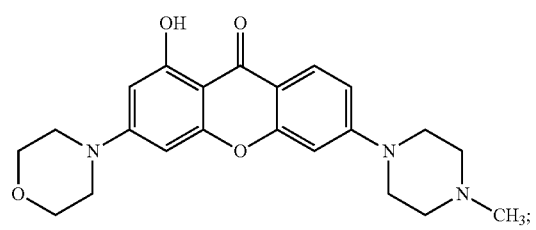
-continued
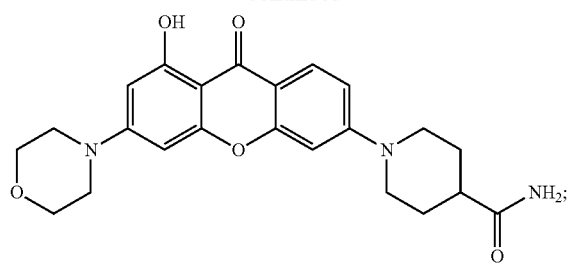
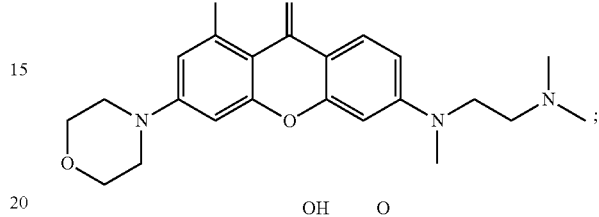
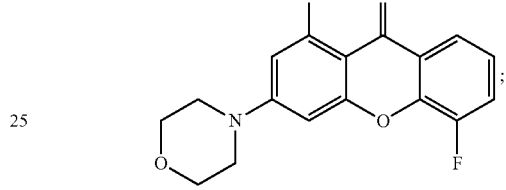
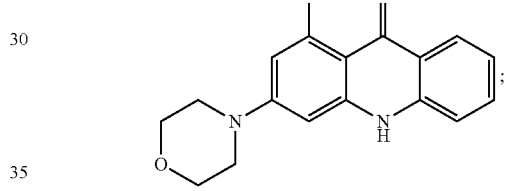
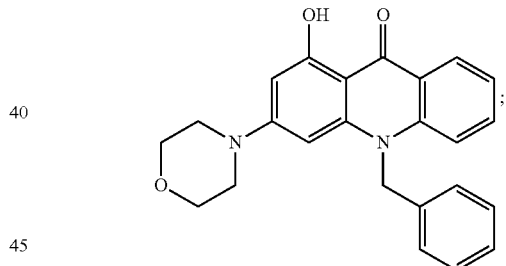
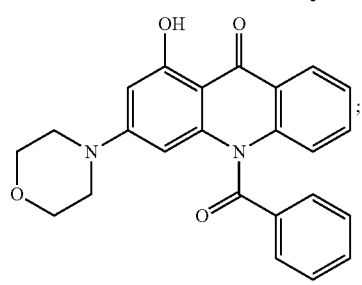
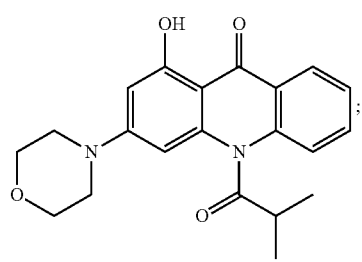

-continued
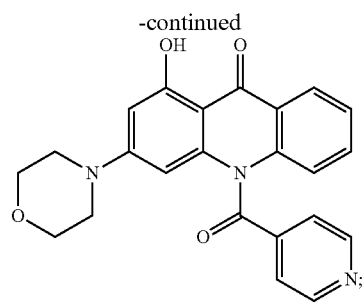
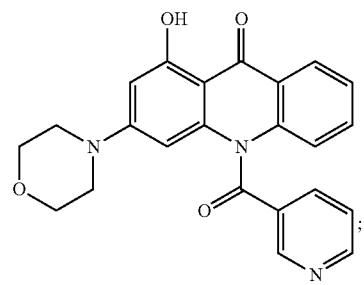
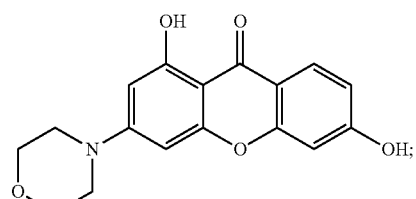
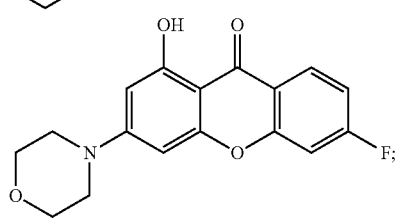
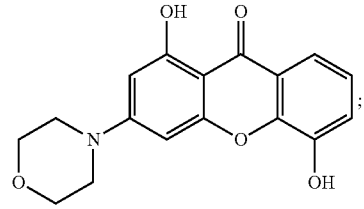
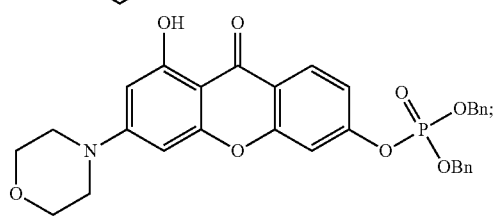
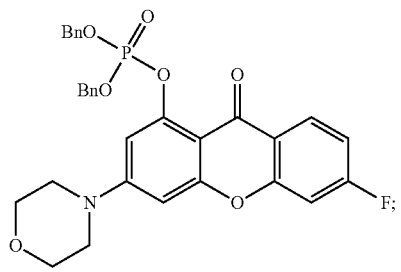
-continued
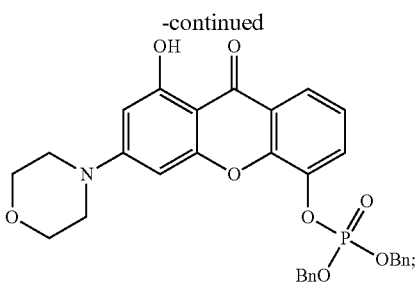
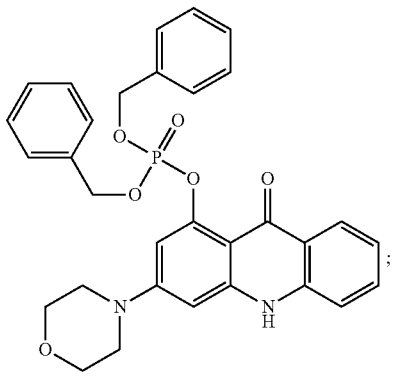
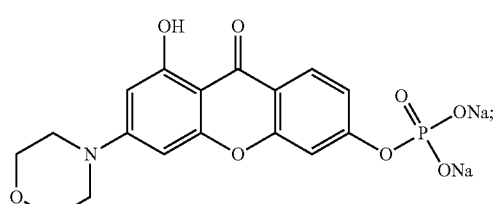
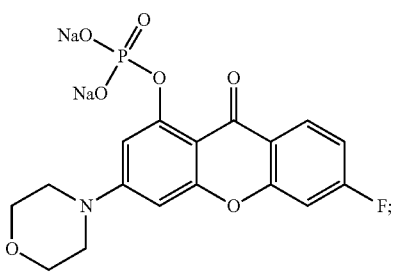 [SMILES: O=c1c2ccc(F)cc2oc2cc(N3CCOCC3)cc(OP(=O)(OCc3ccccc3)OCc3ccccc3)c12]
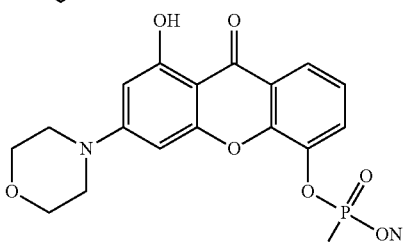
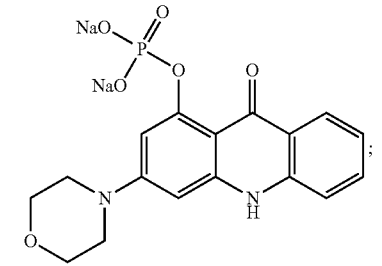

-continued

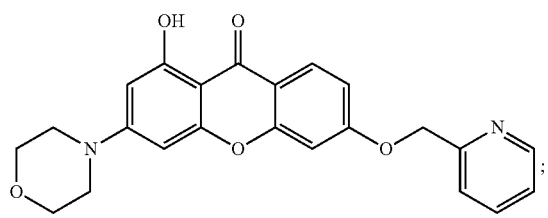

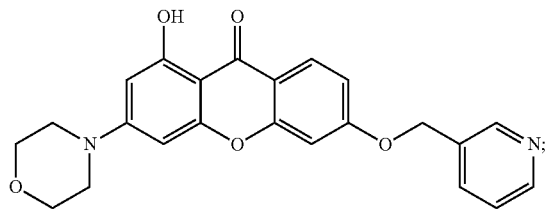

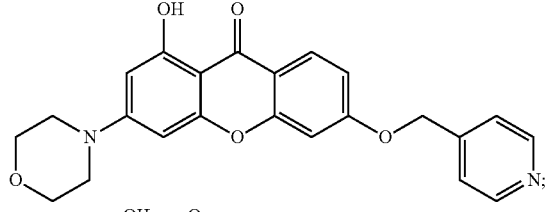

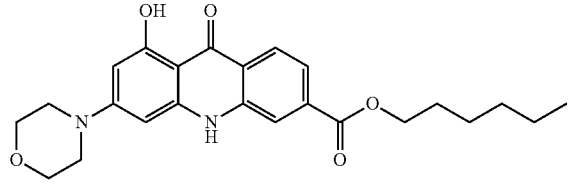

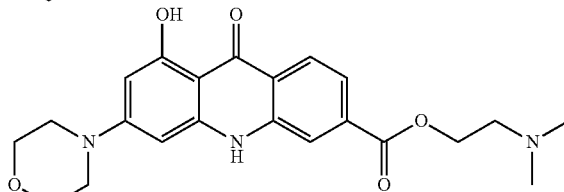

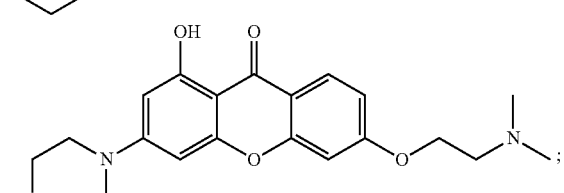

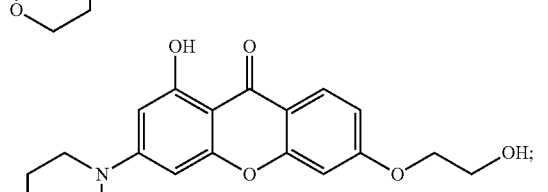

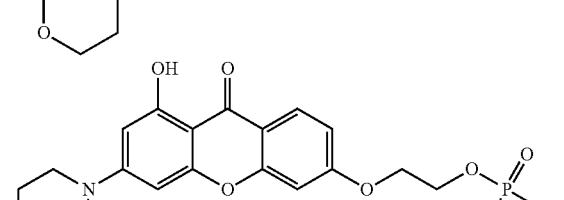

and

-continued

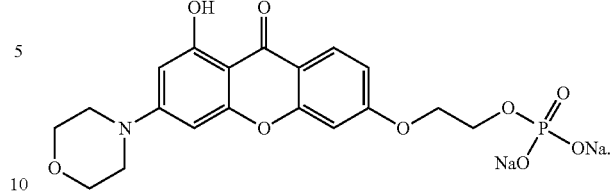

4. The compound of claim 1 having a structure

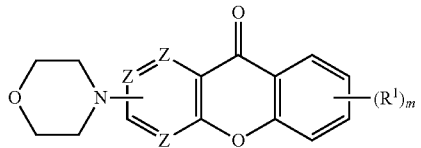

or a pharmaceutically acceptable salt thereof.

5. The compound of claim 1 having a structure

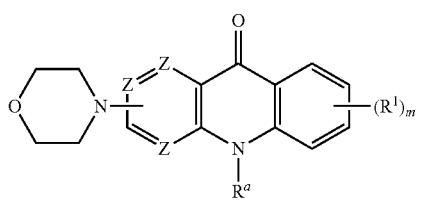

or a pharmaceutically acceptable salt thereof.

6. The compound of claim 1 having a structure

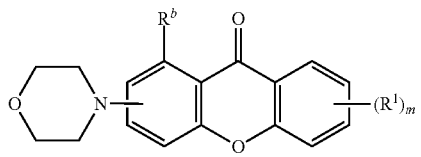

or a pharmaceutically acceptable salt thereof.

7. The compound of claim 1 having a structure

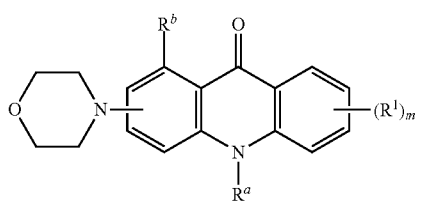

or a pharmaceutically acceptable salt thereof.

8. The compound of claim 1 having a structure

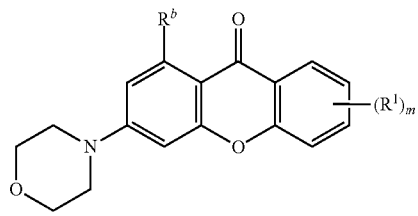

or a pharmaceutically acceptable salt thereof.

9. The compound of claim 1 having a structure

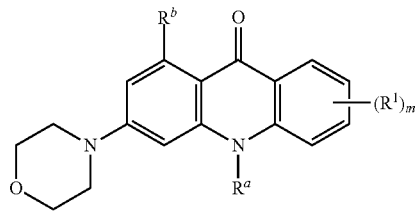

or a pharmaceutically acceptable salt thereof.

10. The compound of claim 1 having a structure

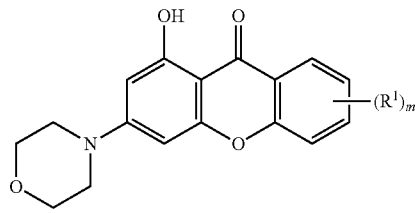

or a pharmaceutically acceptable salt thereof.

11. The compound of claim 1 having a structure

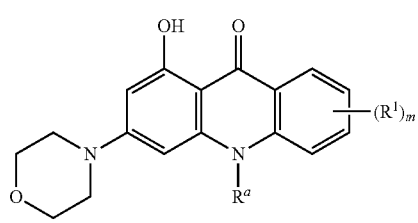

or a pharmaceutically acceptable salt thereof.

12. The compound of any one of claims 1, 2, and 4-11, wherein m is 0; or a pharmaceutically acceptable salt thereof.

13. The compound of any one of claims 1, 2, and 4-11, wherein m is 1; or a pharmaceutically acceptable salt thereof.

14. The compound of any one of claims 1, 2, and 4-11, wherein m is 2; or a pharmaceutically acceptable salt thereof.

15. The compound of claim 3, wherein the formula is

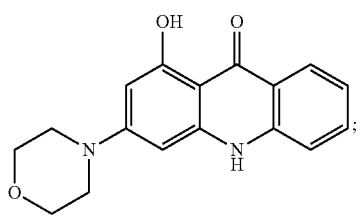

or a pharmaceutically acceptable salt thereof.

16. The compound of claim 3, wherein the formula is

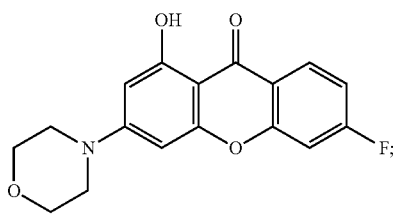 [SMILES: O=c1c2ccc(F)cc2oc2cc(N3CCOCC3)cc(O)c12]

or a pharmaceutically acceptable salt thereof.

17. A pharmaceutical composition comprising (a) a compound of any one of claims 1, 2, 3, and 4-11, 15, and 16 and (b) a pharmaceutically acceptable carrier or diluent.

18. A pharmaceutical composition comprising (a) a compound of any one of claims 1, 2, 3, and 4-11, 15, and 16 and (b) an antineoplastic agent.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: p53 peptide substrate

<400> SEQUENCE: 1

Glu Pro Pro Leu Ser Gln Glu Ala Phe Ala Asp Leu Trp Lys Lys Arg
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Cdc25C peptide

<400> SEQUENCE: 2

Leu Tyr Arg Ser Pro Ser Met Pro Glu Asn Leu Asn Arg Arg Arg Arg
1               5                   10                  15
```